(12) United States Patent
Lindstrom et al.

(10) Patent No.: US 8,241,853 B2
(45) Date of Patent: Aug. 14, 2012

(54) PRIMERS AND PROBES FOR DETECTION AND DISCRIMINATION OF TYPES AND SUBTYPES OF INFLUENZA VIRUSES

(75) Inventors: Stephen Lindstrom, Doraville, GA (US); Alexander Klimov, Atlanta, GA (US); Nancy Cox, Atlanta, GA (US); Lamorris Loftin, Philadelphia, PA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 566 days.

(21) Appl. No.: 12/191,186

(22) Filed: Aug. 13, 2008

(65) Prior Publication Data

US 2009/0111089 A1  Apr. 30, 2009

Related U.S. Application Data

(63) Continuation of application No. PCT/US2007/003646, filed on Feb. 12, 2007.

(60) Provisional application No. 60/772,806, filed on Feb. 13, 2006.

(51) Int. Cl.
*C12Q 1/68* (2006.01)
*C12M 1/34* (2006.01)
*C07H 21/04* (2006.01)

(52) U.S. Cl. ............ 435/6.11; 435/5; 435/6.1; 435/6.12; 435/287.2; 435/810; 536/24.32; 536/24.33

(58) Field of Classification Search .................. None
See application file for complete search history.

(56) References Cited

U.S. PATENT DOCUMENTS 6,544,752 B1  4/2003  Rovinski et al.
7,504,109 B2 *  3/2009  Yang et al. ............... 424/206.1

FOREIGN PATENT DOCUMENTS

WO       02/29118 A1   4/2002
WO    2005/100611 A2  10/2005
WO  WO 2006/121773 A2  11/2006

OTHER PUBLICATIONS

Tyagi, S. et al. Nature Biotechnology 14:303-308 (Mar. 1996).*
Donofrio et al., "Detection of Influenza A and B in Respiratory Secretions with the Polymerase Chain Reaction," *PCR Methods and Applications*, 1(4):263-268 (1992).
Munch et al., "Detection and subtyping (H5 and H7) of avian type A influenza virus by reverse transcription-PCT and PCT-ELISA," *Archives of Virology*, 156(1):87-97 (2001).
Ng et al., "Influenza A H5N1 Detection," *Emerging Infectious Diseases*, 11(8):1303-1305 (2005).
Poddar, Saibal K., "Influenza virus types and subtypes detections by single step single tube multiplex reverse transcription-polymerase chain reaction (RT-PCT) and agarose gel electrophoresis," *Journal of Virological Methods*, 99(1-2):63-70 (2002).
Spackman et al., "Development of a Real-Time Reverse Transcriptase PCR Assay for Type A Influenza Virus and the Avian H5 and H7 Hemagglutinin Subtypes," *Journal of Clinical Microbiology*, 40(9):3256-3260 (2002).
Stone et al., "Rapid detection and simulation subtype differentiation of influenza A viruses by real time PCT," *Journal of Virological Methods*, 117(2):103-112 (2004).
Taubenberger et al., "Initial Genetic Characterization of the 1918 'Spanish' Influenza Virus," *Science, American Association for the Advancement of Science*, 275:1793-1796 (1997).
Ward et al., "Design and performance of quantitative real time PCT assays for influenza A and B viral load measurement," *Journal of Clinical Virology*, 29(3):179-188 (2004).
World Health Organization, "Recommended laboratory tests to identify avian influenza A virus in specimens form humans," pp. 1-7 <http://www.who.int/scr/disease/avian_influenza/guidelines/avian_labtests2.pdf>, Jun. 2005.
Yuen et al., "Clinical features and rapid viral diagnosis of human disease associated with avian influenza A H5N1 virus," *The Lancet*, 351(9101):467-471 (1998).
Li et al., "Typing and Subtyping Influenza Virus Using DNA Microarrays and Multiplex Reverse Transcriptase PCR," *Journal of Clinical Microbiology*, 39(2):696-704 (2001).

* cited by examiner

*Primary Examiner* — Diana Johannsen
(74) *Attorney, Agent, or Firm* — Klarquist Sparkman, LLP

(57) ABSTRACT

Methods of detecting influenza, including differentiating between type and subtype are disclosed, for example to detect, type, and/or subtype an influenza infection. A sample suspected of containing a nucleic acid of an influenza virus, is screened for the presence or absence of that nucleic acid. The presence of the influenza virus nucleic acid indicates the presence of influenza virus. Determining whether the influenza virus nucleic acid is present in the sample can be accomplished by detecting hybridization between an influenza specific probe, influenza type specific probe, and/or subtype specific probe and an influenza nucleic acid. Probes and primers for the detection, typing and/or subtyping of influenza virus are also disclosed. Kits and arrays that contain the disclosed probes and/or primers also are disclosed.

34 Claims, 70 Drawing Sheets

Influenza Nucleic Acid

Sequence Specific Probe

Hybridize and Detect

Influenza Nucleic Acid

Sequence Specific Probe

Melt

Hybridize and Detect

Polymerization

Strand displacement

Reporter Cleavage and Fluorescence

Polymerization Complete

= Reporter
= Quencher

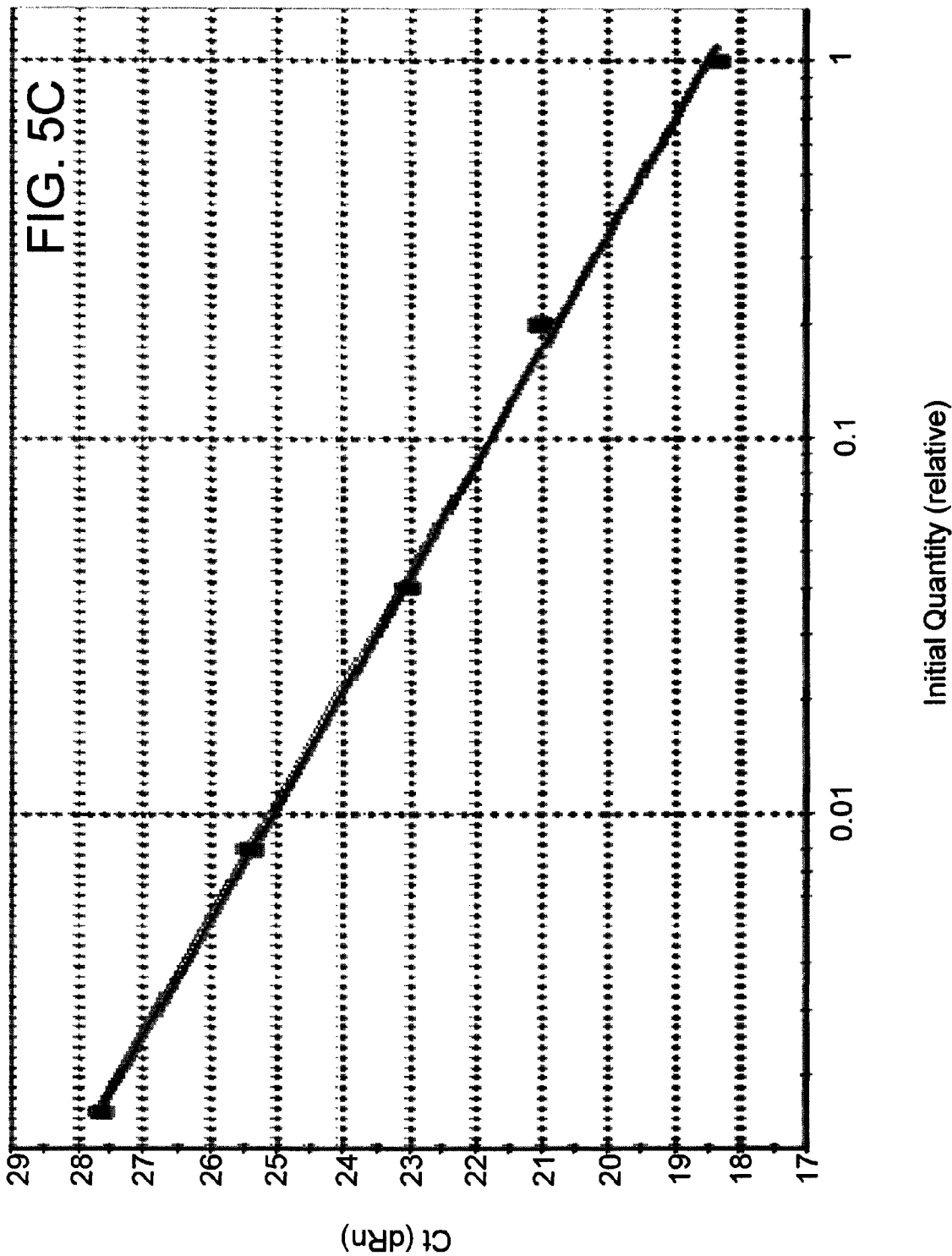

FIG. 9B

| | | | | | | | |
|---|---|---|---|---|---|---|---|
| A/duck/Hubei/W1/2004 | . | . | . | . | . | . | . |
| A/mallard/Xuyi/8/2004 | . | . | A | . | . | . | A |
| A/shorebird/Delaware/10/2004 | A..T | . | A | . | . | . | A..A |
| A/shorebird/Delaware/12/2004 | A..T | . | A | . | . | A | A..A |
| A/shorebird/Delaware/68/2004 | .G | . | A | . | . | . | A |
| A/shorebird/Delaware/75/2004 | .A | . | A | . | C | A | A..A |
| A/swine/Korea/S452/2004 | . | . | . | . | . | . | . |
| A/tern/Australia/91/2004 | .A | . | A | . | . | . | A..T |
| A/avian/Netherlands/219/03 | . | . | . | . | . | . | T |
| A/equine/Massachussetts/213/20 | .A | . | A | . | . | A | A..A |
| A/equine/Ohio/1/2003 | .C | . | A | . | . | . | A..A |
| A/laughing gull/Delaware/5/200 | .A | . | A | . | . | . | A..A |
| A/mallard/Alberta/209/2003 | .A | . | A | . | . | . | A..A |
| A/mallard/Alberta/245/2003 | .A | . | A | . | . | . | A..A |
| A/mallard/Alberta/254/2003 | .A | . | A | . | . | . | A..A |
| A/mallard/Alberta/79/2003 | .A | . | A | . | . | . | A..A |
| A/pintail/Alberta/49/2003 | .A | . | A | . | . | A | A..A |
| A/shorebird/Delaware/236/2003 | . | . | A | . | . | . | A..A |
| A/swine/Shandong/na/2003 | .A | . | A | . | . | . | A..A |
| A/chicken/Chile/184240-4322/20 | .A | G | A | . | C | . | A..A |
| A/mallard/Alberta/149/2002 | .A | . | T.A | . | . | A | A |
| A/turkey/Italy/214845/2002 | .A | . | A | . | . | . | A..A |
| A/turkey/Italy/220158/2002 | .A | . | A | . | . | . | A..A |
| A/duck/Hokkaido/107/01 | . | . | . | T | . | . | . |
| A/green-winged teal/TX/7/01 | .A | . | A | . | . | . | A..A |
| A/mallard/Alberta/24/01 | .A | . | A | . | . | . | A..C |
| A/pintail/Alberta/269/2001 | .A | . | A | . | . | . | A..A |
| A/black-headed gull/Netherland | . | . | .A | . | C | . | A..A |
| A/Duck/Nanchang/2-0492/2000 | .A | . | A | . | . | . | A..T |
| A/pheasant/Hong Kong/NT261/00 | . | . | A | . | . | . | A |
| A/ruddy turnstone/Delaware/97/ | A. | . | A | . | C | G | A..A |
| A/Chicken/Pakistan/2/99 | . | . | A | . | . | . | A |
| A/shoveler/Netherlands/19/1999 | . | . | A | . | . | . | A |

FIG. 9C

| Strain | | | |
|---|---|---|---|
| A/Swine/Ontario/1911-2/99 | .G...... | ........ | ........ |
| A/chicken/Taiwan/na3/98 | ........ | ........ | .A...A.. |
| A/duck/Siberia/272PF/98 | .A...... | ...T.... | .A...... |
| A/mallard/Alberta/205/1998 | .A...A.. | ........ | .A...A.. |
| A/blue-winged teal/Alberta/16/ | .A...A.. | ........ | .A...... |
| A/mallard/Alberta/202/1996 | .A...A.. | ........ | .A...A.. |
| A/pintail/Alberta/275/1996 | .A...A.. | ........ | .A...A.. |
| A/chicken/New York/13828-3/199 | .A...A.. | ........ | .A...A.. |
| A/ruddy turnstone/Delaware/34/ | ........ | ........ | ....T... |
| A/duck/Nanchang/1749/1992 | .A...A.. | ........ | .A...A.. |
| A/mallard/Alberta/194/1992 | .A...A.. | ........ | .A...... |
| A/duck/Alaska/658/1991 | .A...A.. | ........ | ..T..A.T |
| A/mallard/Alberta/17/1991 | .A...A.. | ........ | .A...... |
| A/herring gull/Delaware/670/19 | ........ | ........ | ..T.C.A. |
| A/herring gull/Delaware/692/19 | .A...A.. | .T...... | .A...A.. |
| A/herring gull/Delaware/712/19 | .A...A.. | ........ | .A...... |
| A/mallard duck/Alberta/353/198 | .A...A.. | ........ | .A...... |
| A/chicken/Taiwan/G2/87 | .A...A.. | ........ | .A...... |
| A/coot/Alberta/134/1987 | ........ | .A...... | .A...A.. |
| A/laughing gull/New Jersey/798 | .A...A.. | ........ | ....C.A.. |
| A/sanderling/Delaware/1258/198 | .A...A.. | ........ | .A...... |
| A/sooty tern/Western Australia | ........ | ........ | ........ |
| A/mallard duck/Astrakhan/263/1 | .A...A.. | ........ | ..C..A.A. |
| A/pintail duck/New York/155/19 | .A...A.. | ........ | .A...A.. |
| A/wood duck/New York/60/1982 | .A...A.. | .A...... | ..A..A.. |
| A/red-necked stint/Australia/5 | ........ | ........ | .C.A.A.. |
| A/red-necked stint/Australia/4 | .A...A.. | ........ | .C.A.A.. |
| A/seal/Mass/1/80 (MA) | .A...A.. | ........ | ...A.A.. |
| A/Equine/Newmarket/1/77 | .A...A.. | ........ | ....C.A.. |
| A/gull/Maryland/19/1977 | ........ | ........ | .A...A.. |
| A/pintail/Alberta/293/1977 | .A...A.. | ........ | .A...... |
| A/mallard duck/Alberta/57/1976 | .A...A.. | ........ | CC.A.A.. |
| A/black-legged kittywake/Alask | .A...A.. | .T...... | .A...A.. |

B/Hong Kong/70/1996
B/Houston/B15/1999
B/Houston/B56/1997
B/Houston/B65/1998
B/Houston/B66/2000
B/Houston/B69/2002
B/Houston/B71/2002
B/Houston/B720/2004
B/Houston/B745/2005
B/Houston/B756/2005
B/Houston/B787/2005
B/Houston/B81/2003
B/Houston/B846/2005
B/Illinois/47/2005
B/Kouchi/193/1999
B/Memphis/12/97
B/Mexico/84/2000
B/Michigan/04/2006
B/Mie/01/1993
B/Moscow/16/2002
B/Nepal/1331/2005
B/Oita/15/1992
B/Osaka/547/1997
B/Paraguay/636/2003
B/Paris/549/1999
B/Romania/217/1999
B/Russia/22/1995
B/Shangdong/7/97
B/Shizuoka/480/2000
B/Singapore/22/1998

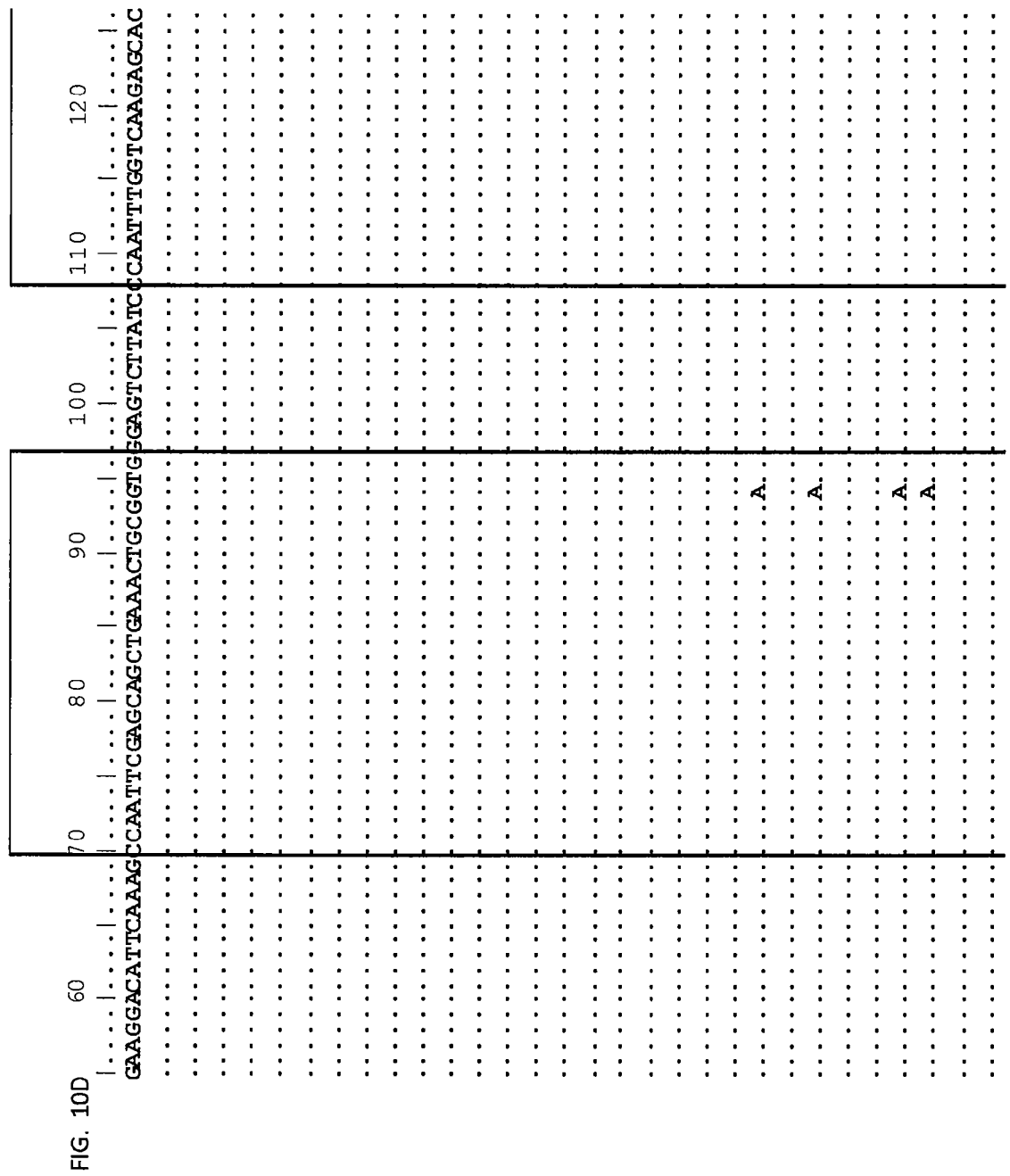

FIG. 13B

| | | | | | |
|---|---|---|---|---|---|
| Asia2005_16 | C.G. | . | . | . | . |
| Asia2005_17 | C.G. | . | . | . | . |
| Asia2005_18 | C.G. | . | . | . | . |
| Asia2005_19 | C.G. | . | . | . | . |
| Asia2005_20 | .G | . | . | . | . |
| Asia2005_21 | . | . | . | . | . |
| Asia2005_22 | . | . | . | . | . |
| Asia2005_23 | C | .G | . | . | . |
| Asia2005_24 | C | C | .G | . | . |
| Asia2005_25 | . | C | . | . | . |
| Asia2005_26 | C | . | . | . | . |
| Asia2006_1 | C | . | . | . | CA. |
| Asia2006_2 | C | . | . | . | CA. |
| Asia2006_3 | C | . | . | . | CA. |
| Asia2006_4 | C | . | . | . | CA. |
| Asia2006_5 | . | . | . | . | CA. |
| Asia2006_6 | C | . | . | . | CA. |
| Asia2006_7 | C | . | . | . | A. |
| Asia2006_8 | C | . | . | . | A. |
| Asia2006_9 | C | . | . | . | . |
| Asia2006_10 | C | . | . | . | . |
| Asia2006_11 | C | . | . | . | . |
| Africa2006_1 | C.G | . | . | . | . |
| Africa2006_2 | C.G | . | . | . | . |

| Strain | | | | |
|---|---|---|---|---|
| A/guineafowl/Hong Kong/NT184/0 | | | | |
| A/duck/Xuzhou/07/2003 | .G | | | |
| A/chicken/Hong Kong/FY23/03 | | .A | .C | .A |
| A/chicken/Hong Kong/TP38/03 | | | | .T |
| A/swine/ShanDong/1/2003 | .G | | .C | |
| A/Chicken/ShangHai/1/02 | | | .C | |
| A/Chicken/Liaoning/1/00 | .G | | .A | .T |
| A/Chicken/Yunnan/2/00 | | | | |
| A/Chicken/Shanghai/3/00 | .G | | | |
| A/Duck/Shantou/1796/00 | | | | |
| A/Chicken/Hebei/2/00 | | .A | | .G .T |
| A/Hokkaido/9/99 | .G | .A | | |
| A/chicken/Gansu/2/99 | | | | |
| A/chicken/Shandong/2/99 | | | .T | .T |
| A/Chicken/Guangxi/KMI/99 | | | | |
| A/Chicken/Henan/1/99 | | | | |
| A/Chicken/Jiangsu/1/99 | | | | |
| A/chicken/Hong Kong/WF2/99 | .G | | | .T |
| A/Chicken/Henan/2/98 | | | | |
| A/Chicken/Shandong/1/98 | .G | | | |
| A/Chicken/Jiangsu/2/98 | | | | |
| A/parakeet/Narita/92A/98 | | | | |
| A/Chicken/Beijing/1/97 | .G | | .A | .T |
| A/parakeet/Chiba/1/97 | | | | |
| A/Chicken/Tianjing/1/96 | .G | .A | .G .A | .G .T |
| A/Chicken/Korea/ms96/96(ECE3) | .G | .A | | .G |
| A/Chicken/Guangdong/SS/94 | | | | |
| A/quail/Hong Kong/A28945/88 | .G | .A .A | .A | .T .A |
| A/duck/Hong Kong/702/79 | .G | | | .T |

FIG. 17C

A/duck/Hong Kong/448/78
A/duck/Hong Kong/147/1977
A/duck/Hong Kong/644/79
A/Chicken/Hong Kong/739/94
A/Quail/Hong Kong/AF157/92
A/Duck/Hong Kong/168/77
A/Chicken/Beijing/1/94
A/Duck/Viet Nam/340/2001
A/Duck/Viet Nam/68/2001
A/swine/Hong Kong/10/98
A/swine/Hong Kong/9/98
A/Chicken/Henan/62/00
A/Chicken/Guangdong/11/97
A/chicken/Henan/ni/2001
A/chicken/Korea/164/04

PRIMERS AND PROBES FOR DETECTION AND DISCRIMINATION OF TYPES AND SUBTYPES OF INFLUENZA VIRUSES

CROSS REFERENCE TO RELATED APPLICATION

This application is a continuing application of International Application No. PCT/US2007/003646, filed Feb. 12, 2007, published under PCT Article 21(2) in English, and claims the benefit of U.S. Provisional Application No. 60/772,806, filed Feb. 13, 2006, both of which applications are incorporated by reference herein in their entirety.

FIELD

This disclosure relates to primers and probes for detecting one or more types or subtypes of influenza virus, as well as kits including the probes and primers and methods of using the probes and primers.

BACKGROUND

Influenza virus types A and B are members of the orthomyxoviridae family of viruses that cause influenza infection. The infective potential of influenza is frequently underestimated and can result in high morbidity and mortality rates, especially in elderly persons and in high-risk patients, such as the very young and immuno-compromised. Influenza A and B viruses primarily infect the nasopharyngeal and oropharyngeal cavities and produce highly contagious, acute respiratory disease that results in significant morbidity and economic costs. Typical influenza viral infections in humans have a relatively short incubation period of 1 to 2 days, with symptoms that last about a week including an abrupt onset of fever, sore throat, cough, headache, myalgia, and malaise. When a subject is infected with a highly virulent strain of influenza these symptoms can progress rapidly to pneumonia and in some circumstances death. Pandemic outbreaks of highly virulent influenza present a serious risk to human and animal health worldwide.

The immunodominant antigens present on the surface of influenza viruses are hemagglutinin (HA or H) and neuraminidase (N). Genetic reassortment between human and avian influenza viruses can result in a virus with a novel hemagglutinin of avian origin, against which humans lack immunity. In the $20^{th}$ century, the pandemics of 1918, 1957, and 1968 were the result of such antigenic shifts. The avian influenza outbreaks of the early $21^{st}$ century caused by H5N1, H7N7, and H9N2 subtype influenza viruses, and their infection of humans have created a new awareness of the pandemic potential of influenza viruses that circulate in domestic poultry. The economic impact of a major influenza pandemic has been estimated to be up to $165 billion in the United States alone, with as many as 200,000 deaths, 730,000 hospitalizations, 42 million outpatient visits, and 50 million additional illnesses.

To combat influenza infection, neuraminidase inhibitors have recently been developed. Clinical studies carried out for the Food and Drug Administration's (FDA) approval of neuraminidase inhibitors in the United States showed that successful treatment primarily depends on prompt treatment after the first clinical symptoms occur. Unfortunately, it is generally not possible for even experienced medical professionals to reliably diagnose influenza solely on the basis of the patient's clinical symptoms because other viruses which infect the nasal or pharyngeal cavity, such as adenoviruses, parainfluenza viruses, or respiratory syncitial viruses (RS viruses), cause similar symptoms. To effectively treat influenza infection it is necessary to begin treatment as early as possible in the development of the infection, ideally upon the onset of non-virally specific clinical symptoms.

A variety of methods have been used to detect influenza viruses clinically. In one example, influenza viruses are detected by culturing samples obtained from a subject on mammalian cells such as Madine-Darby Canine Kidney cells (MDCK). Culturing mammalian cells is costly and time consuming (taking up to 14 days) and is thus not of immediate relevance for the diagnosis of the individual patient. Other methods of detection that have been developed include immunofluorescence assays (IFA), enzyme immunoassays (EIA), and enzyme-linked immunosorbent assays (ELISA) that use antibodies specific to influenza virus antigens. Culture and serological tests require long completion times (5 days to 2 weeks) with potentially greater exposure of technical personnel to infectious agents. Immunoassays are generally faster (30 minutes to 4 hours) but often require substantial sample handling and rely on subjective determination of results by technical personnel. Furthermore, these tests typically are not capable of rapidly differentiating between the influenza types and subtypes, some of which have pandemic potential.

Hence the need remains for a test that provides sensitive, specific detection of influenza virus types and subtypes in a relatively short time, so that diagnosis is completed in sufficient time to permit effective treatment of an infected person.

SUMMARY

The present disclosure relates to methods of detecting the presence of an influenza virus in a sample, such as a biological sample obtained from a subject. The disclosed methods can be used for diagnosing an influenza infection in a subject suspected of having an influenza infection by analyzing a biological specimen from a subject to detect a broad variety of influenza types and subtypes. Alternatively, the method can be used to quickly identify particular types and subtypes of influenza virus, particularly viruses that may be involved in pandemics. In addition, panels of probes are provided that permit the rapid evaluation of a subject with an apparent viral illness by quickly determining whether the illness is caused by a virulent pandemic virus (such as an H5 virus, for example H5N1). This rapid evaluation involves ruling out the presence of the pandemic virus (for example by positively identifying a non-pandemic pathogen such as influenza type B), ruling in the presence of the pandemic virus (for example by identifying a pandemic viral pathogen such as an H5 virus, for example H5N1), or a combination of both.

In some embodiments, the method involves hybridizing an influenza nucleic acid to an influenza specific probe between 20 and 40 nucleotides in length, and detecting hybridization between influenza nucleic acid and the probe. In some embodiments, the probe is detectably labeled. In some embodiments, the probe is capable of hybridizing under conditions of very high stringency to an influenza nucleic acid sequence set forth as SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50. In specific embodiments, the probe includes a nucleic acid sequence that is at least 95% identical to a nucleic acid sequence set forth as SEQ ID NO:8, SEQ ID NO: 11, SEQ ID NO:14, SEQ ID NO:19, SEQ ID NO:24, SEQ ID NO:29, SEQ ID NO:32, SEQ ID NO:35, or SEQ ID NO:38.

The present disclosure also relates to methods of detecting and/or discriminating between influenza viral types and/or subtypes. These methods include contacting a sample with a probe that is specific for an influenza type and/or subtype and detecting the hybridization between the influenza type and/or subtype specific probe. Detection of hybridization between an influenza type and/or subtype specific probe and an influenza nucleic acid indicates that the influenza type and/or subtype is present in the sample. In some embodiments, the methods include detecting an influenza viral type and/or subtype. In one example, detecting hybridization to a nucleic acid sequence at least 95% identical to SEQ ID NO:8 indicates the presence of influenza type A. In another example, detecting hybridization to a nucleic acid sequence at least 95% identical to SEQ ID NO: 11 indicates the presence of influenza subtype H1. In another example, detecting hybridization to a nucleic acid sequence at least 95% identical to SEQ ID NO: 14 indicates the presence of influenza subtype H3. In another example, detecting hybridization to a nucleic acid sequence at least 95% identical to SEQ ID NO: 19 indicates the presence of influenza subtype H5. In another example, detecting hybridization to a nucleic acid sequence at least 95% identical to SEQ ID NO:24 indicates the presence of influenza subtype H5. In another example, detecting hybridization to a nucleic acid sequence at least 95% identical to SEQ ID NO:29 indicates the presence of influenza type B. In another example, detecting hybridization to a nucleic acid sequence at least 95% identical to SEQ ID NO:32 indicates the presence of influenza subtype North American H7. In another example, detecting hybridization to a nucleic acid sequence at least 95% identical to SEQ ID NO:35 indicates the presence of influenza subtype European H7. In yet another example, detecting hybridization to a nucleic acid sequence at least 95% identical to SEQ ID NO:38 indicates the presence of subtype Asian H9 in the sample.

In some embodiments, the methods disclosed herein include amplifying the influenza nucleic acids with at least one primer specific for an influenza nucleic acid. In some embodiments, the primer specific for an influenza nucleic acid is 15 to 40 nucleotides in length and is capable of hybridizing under very high stringency conditions to an influenza virus nucleic acid sequence set forth as SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50. In some embodiments, the primer specific for an influenza nucleic acid is 15 to 40 nucleotides in length and includes a nucleic acid sequence at least 95% identical to the nucleotide sequence set forth as SEQ ID NO:3, SEQ ID NO:4, SEQ ID NO:9, SEQ ID NO:10, SEQ ID NO:12, SEQ ID NO:13, SEQ ID NO:17, SEQ ID NO: 18, SEQ ID NO: 22, SEQ ID NO:23, SEQ ID NO:26, SEQ ID NO:28, SEQ ID NO:30, SEQ ID NO:31, SEQ ID NO:33, SEQ ID NO:34, SEQ ID NO:36, or SEQ ID NO:37.

In some embodiments, the influenza nucleic acid is amplified using at least one primer, such as a pair of primers, specific for an influenza type and/or subtype. In some examples, a primer specific for influenza type A includes a nucleic acid sequence at least 95% identical to the nucleic acid sequence set forth as one of SEQ ID NO:3 or SEQ ID NO:4. In other examples, a primer specific for influenza subtype H1 includes a nucleic acid sequence at least 95% identical to the nucleic acid sequence set forth as one of SEQ ID NO:9 or SEQ ID NO:10. In other examples, a primer specific for influenza subtype H3 includes a nucleic acid sequence at least 95% identical to the nucleic acid sequence set forth as one of SEQ ID NO:12 or SEQ ID NO: 13. In other examples, a primer specific for influenza subtype H5 includes a nucleic acid sequence at least 95% identical to the nucleic acid sequence set forth as one of SEQ ID NO: 17 or SEQ ID NO: 18. In other examples, a primer specific for influenza subtype H5 includes a nucleic acid sequence at least 95% identical to the nucleic acid sequence set forth as one of SEQ ID NO:22 or SEQ ID NO:23. In other examples, a primer specific for influenza type B includes a nucleic acid sequence at least 95% identical to the nucleic acid sequence set forth as one of SEQ ID NO:26 or SEQ ID NO:28. In other examples, a primer specific for influenza subtype North American H7 includes a nucleic acid sequence at least 95% identical to the nucleic acid sequence set forth as one of SEQ ID NO:30 or SEQ ID NO:31. In other examples, a primer specific for influenza subtype European H7 includes a nucleic acid sequence at least 95% identical to the nucleic acid sequence set forth as one of SEQ ID NO:33 or SEQ ID NO:34. In other examples, a primer specific for influenza subtype Asian H9 includes a nucleic acid sequence at least 95% identical to the nucleic acid sequence set forth as one of SEQ ID NO:36 or SEQ ID NO:37.

Additional methods for detecting, typing, and/or subtyping an influenza virus in a sample include hybridizing nucleic acids in the sample to at least one influenza type and/or subtype specific probe arrayed in a predetermined array with an addressable location.

This disclosure also relates to probes capable of hybridizing to and discriminating between influenza nucleic acids from specific types and/or subtypes. In some embodiments, these probes are between 20 and 40 nucleotides in length and capable of hybridizing under very high stringency conditions to an influenza nucleic acid sequence set forth as SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50. In several examples, these probes are between 20 and 40 nucleotides in length and include a nucleic acid sequence set forth as SEQ ID NO:8, SEQ ID NO:11, SEQ ID NO:14, SEQ ID NO:19, SEQ ID NO:24, SEQ ID NO:29, SEQ ID NO:32, SEQ ID NO:35, or SEQ ID NO:38.

This disclosure also relates to primers capable of hybridizing to and amplifying an influenza nucleic acid, such as an influenza nucleic acid specific to an influenza type and/or subtype. In some embodiments, these primers are between 20 and 40 nucleotides in length and capable of hybridizing under very high stringency conditions to an influenza nucleic acid sequence set forth as SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50. In several examples, these primers are 15 to 40 nucleotides in length and include a nucleic acid sequence at least 95% identical to a nucleic acid sequence set forth as SEQ ID NO:3, SEQ ID NO:4, SEQ ID NO:9, SEQ ID NO:10, SEQ ID NO:12, SEQ ID NO:13, SEQ ID NO:17, SEQ ID NO: 18, SEQ ID NO: 22, SEQ ID NO:23, SEQ ID NO:26, SEQ ID NO:28, SEQ ID NO:30, SEQ ID NO:31, SEQ ID NO:33, SEQ ID NO:34, SEQ ID NO:36, or SEQ ID NO:37.

The disclosure also provides devices, such as arrays, as well as kits for detecting, typing, and/or subtyping an influenza virus in a sample suspected of containing an influenza virus.

The foregoing and other objects, features, and advantages of the invention will become more apparent from the following detailed description, which proceeds with reference to the accompanying figures.

BRIEF DESCRIPTION OF THE DRAWINGS

FIG. 5C is a plot of the Ct values extracted from the graphs shown in FIG. 5A, as a function of concentration of template nucleic acid concentration.

Figure 9E:
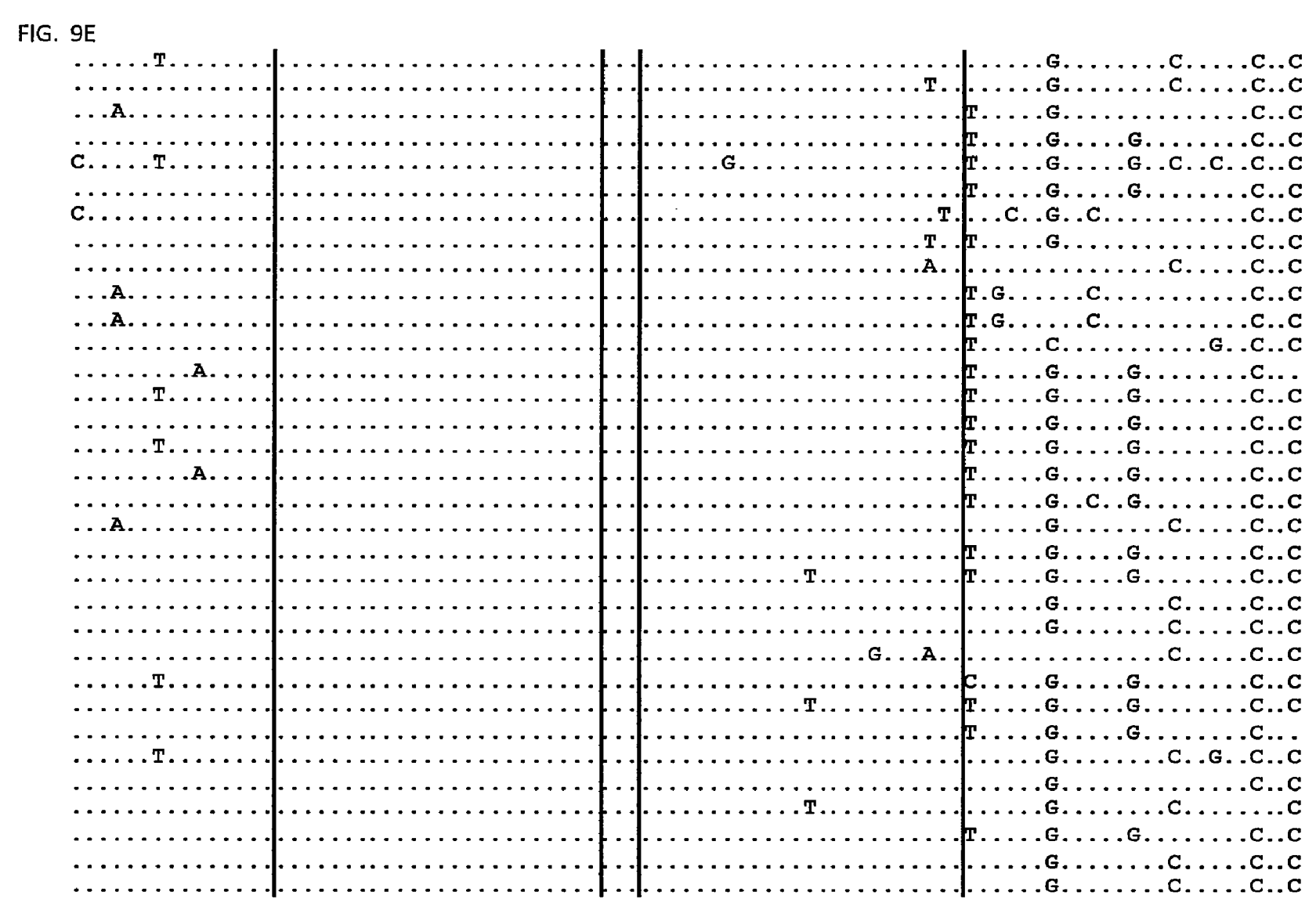
Figure 9F:
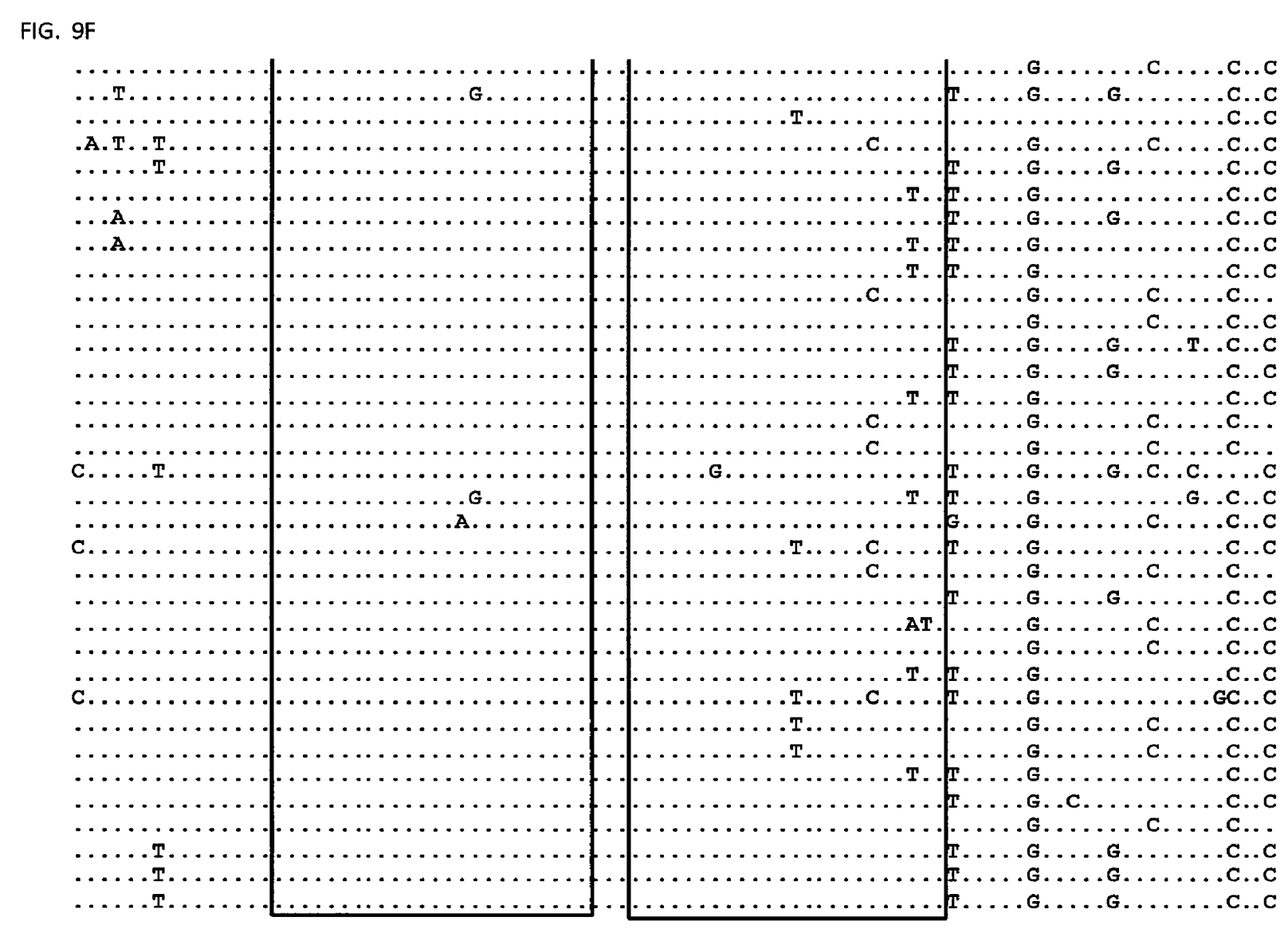

FIG. 9A-9F is a table showing the consensus sequence and variations present in the specified influenza isolates for the region of the influenza type A M gene (SEQ ID NO: 42) used to design the disclosed influenza type A specific probes and primers.

FIG. 10A-10I is a table showing the consensus sequence and variations present in the specified influenza isolates for the region of the influenza type B NS gene (SEQ ID NO: 43) used to design the disclosed influenza type B specific probes and primers.

Figure 13G:
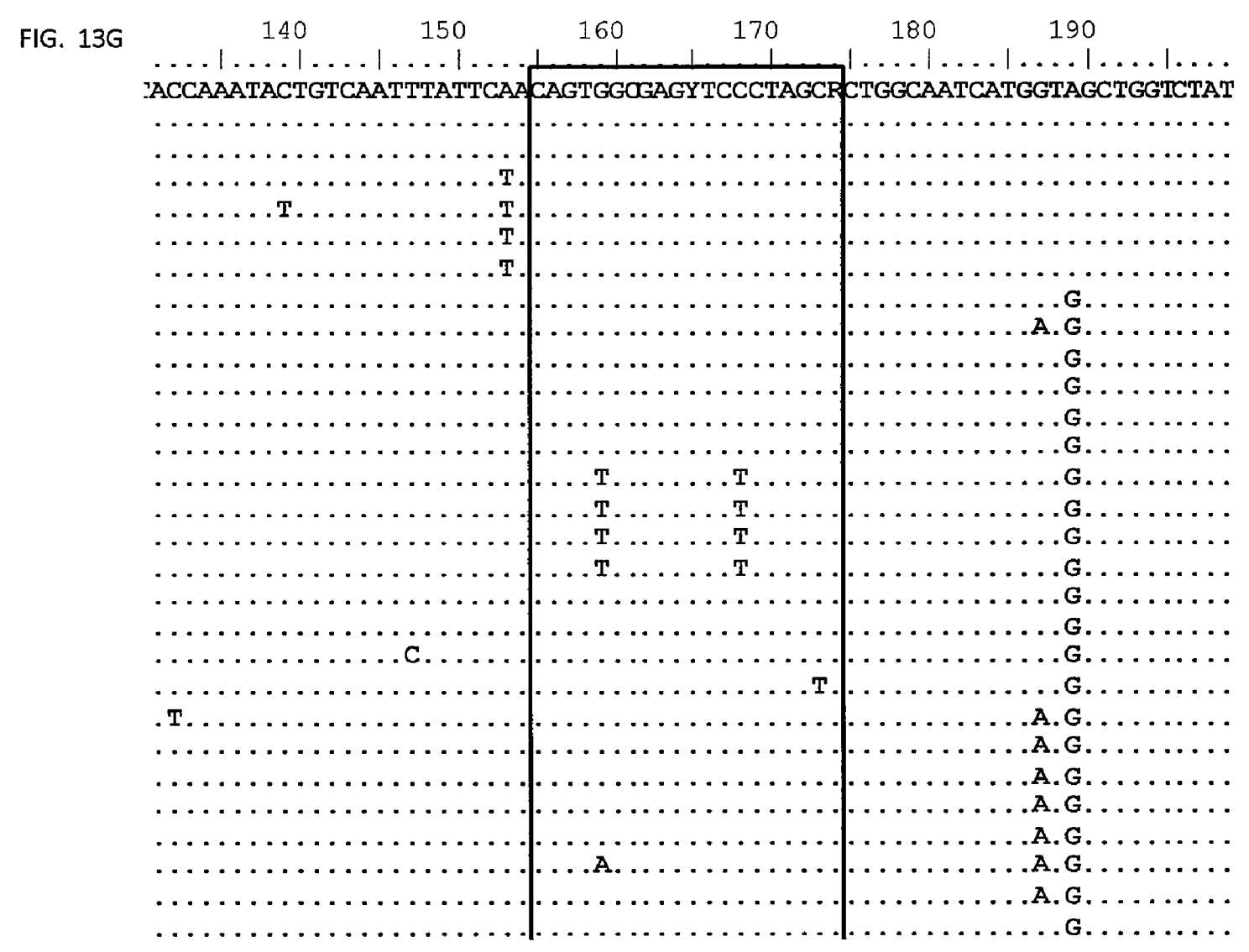
Figure 13H:
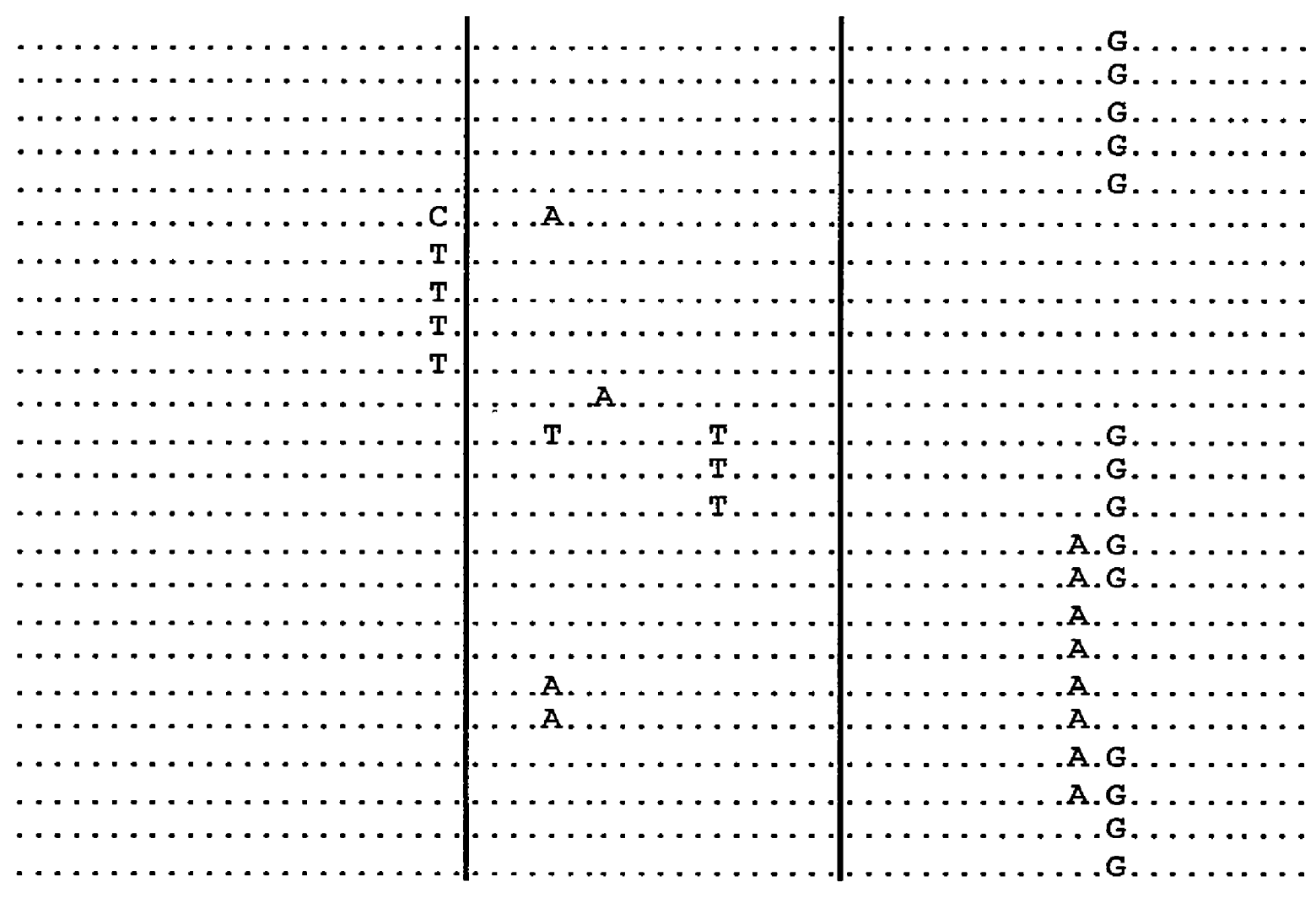

FIG. 13A-13I is a table showing the consensus sequence and variations present in the specified influenza isolates for a region of the influenza subtype H5 HA gene (SEQ ID NO: 46) used to design the disclosed influenza subtype H5 specific probes and primers that.

Figure 14D:
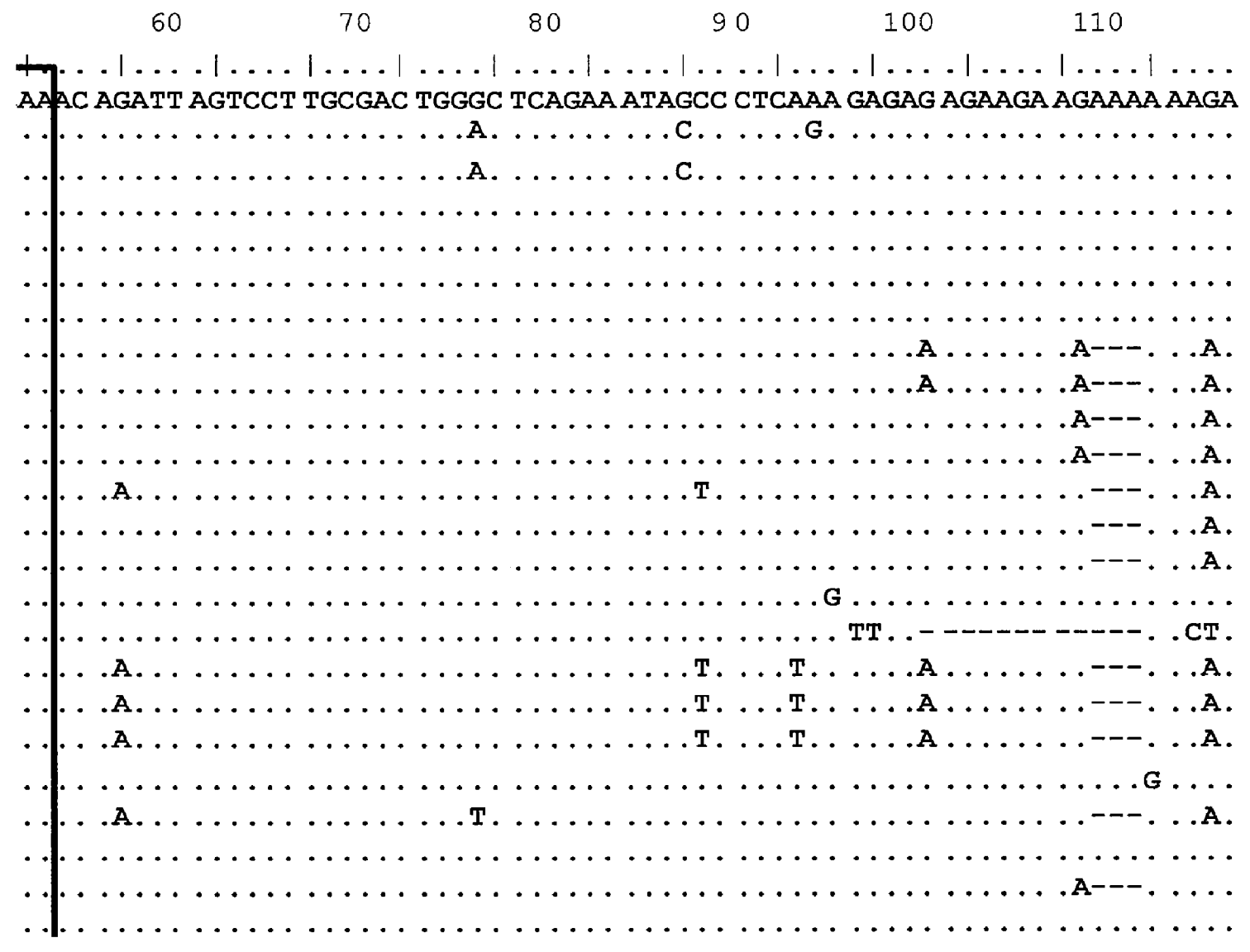
Figure 14E:
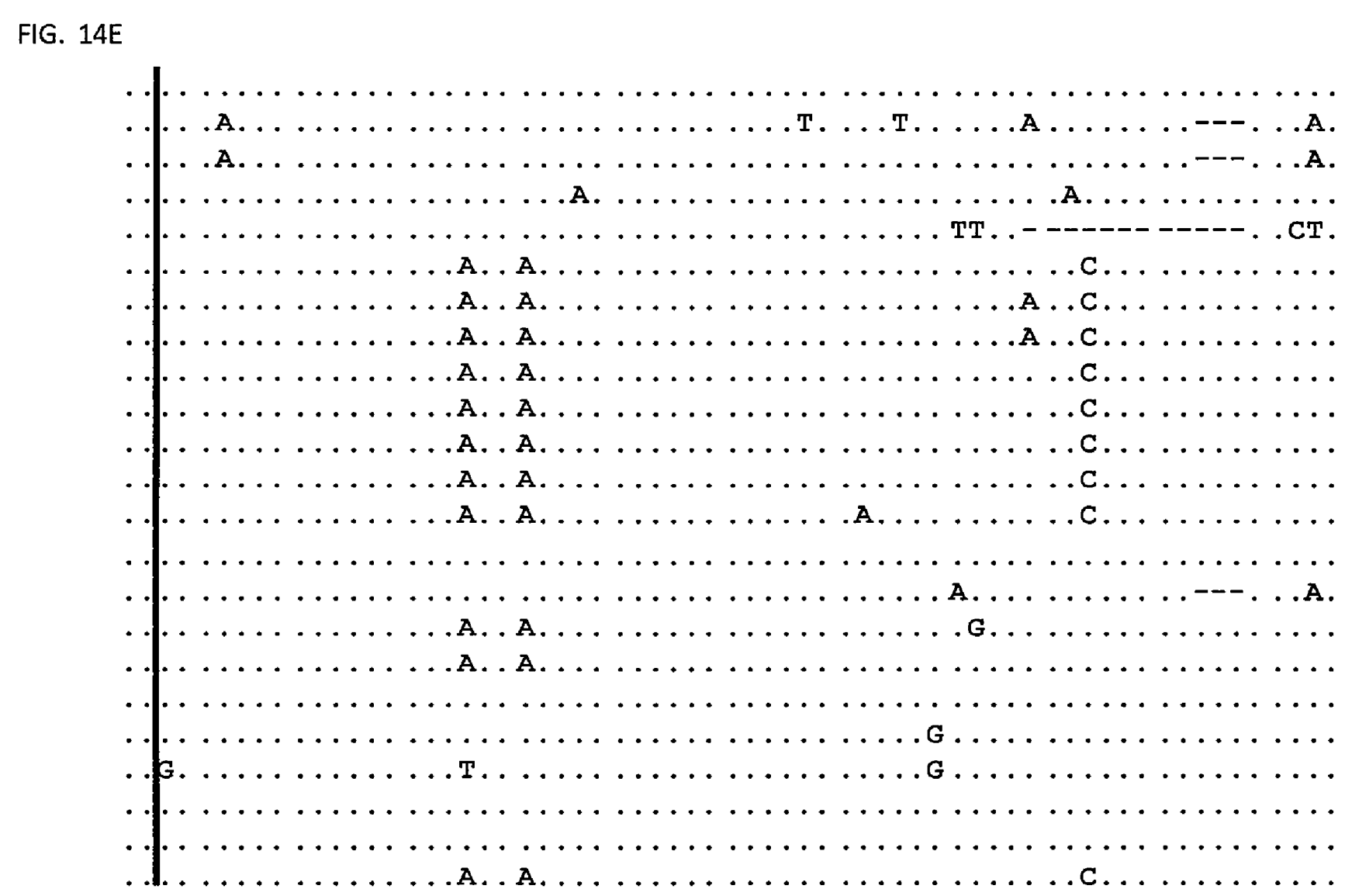
Figure 14F:
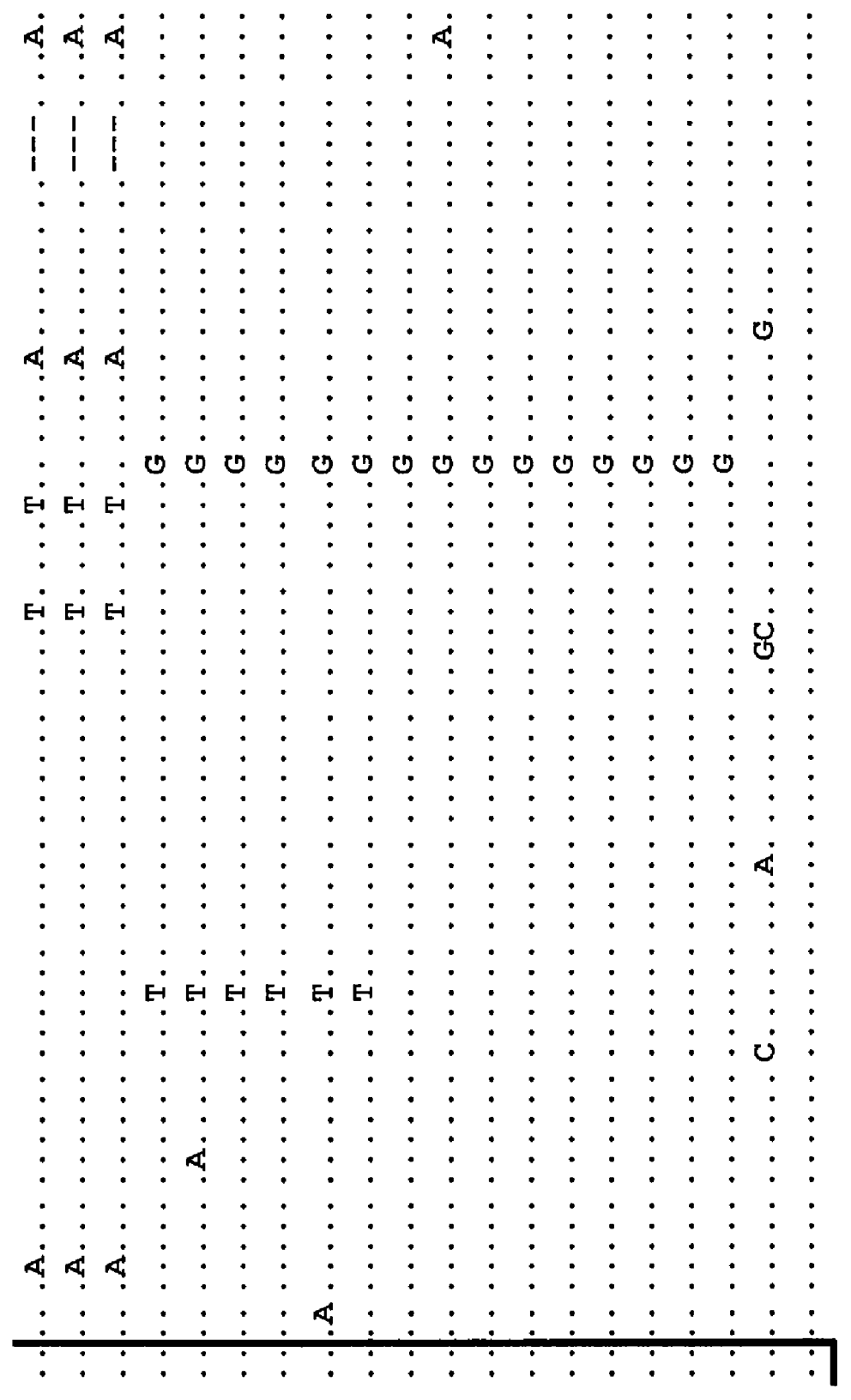

FIG. 14A-14L is a table showing the consensus sequence and variations present in the specified influenza isolates for a region of the influenza subtype H5 HA gene (SEQ ID NO: 47) used to design the disclosed influenza subtype H5 specific probes and primers.

Figure 15B:
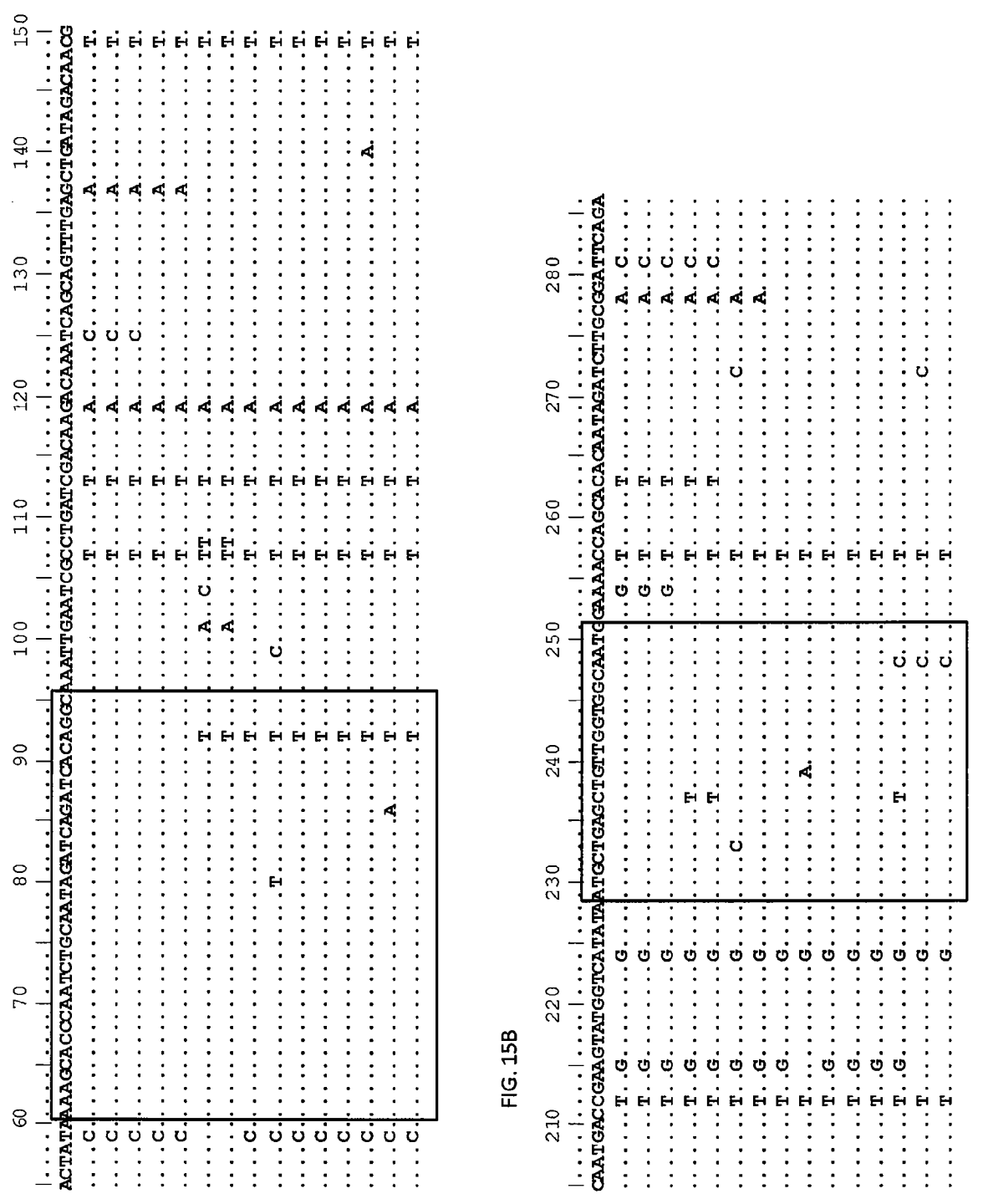

FIG. 15A-15B is a table showing the consensus sequence and variations present in the specified influenza isolates for the region of the influenza subtype North American H7 HA gene (SEQ ID NO: 48) used to design the disclosed influenza subtype North American H7 specific probes and primers.

Figure 16B:
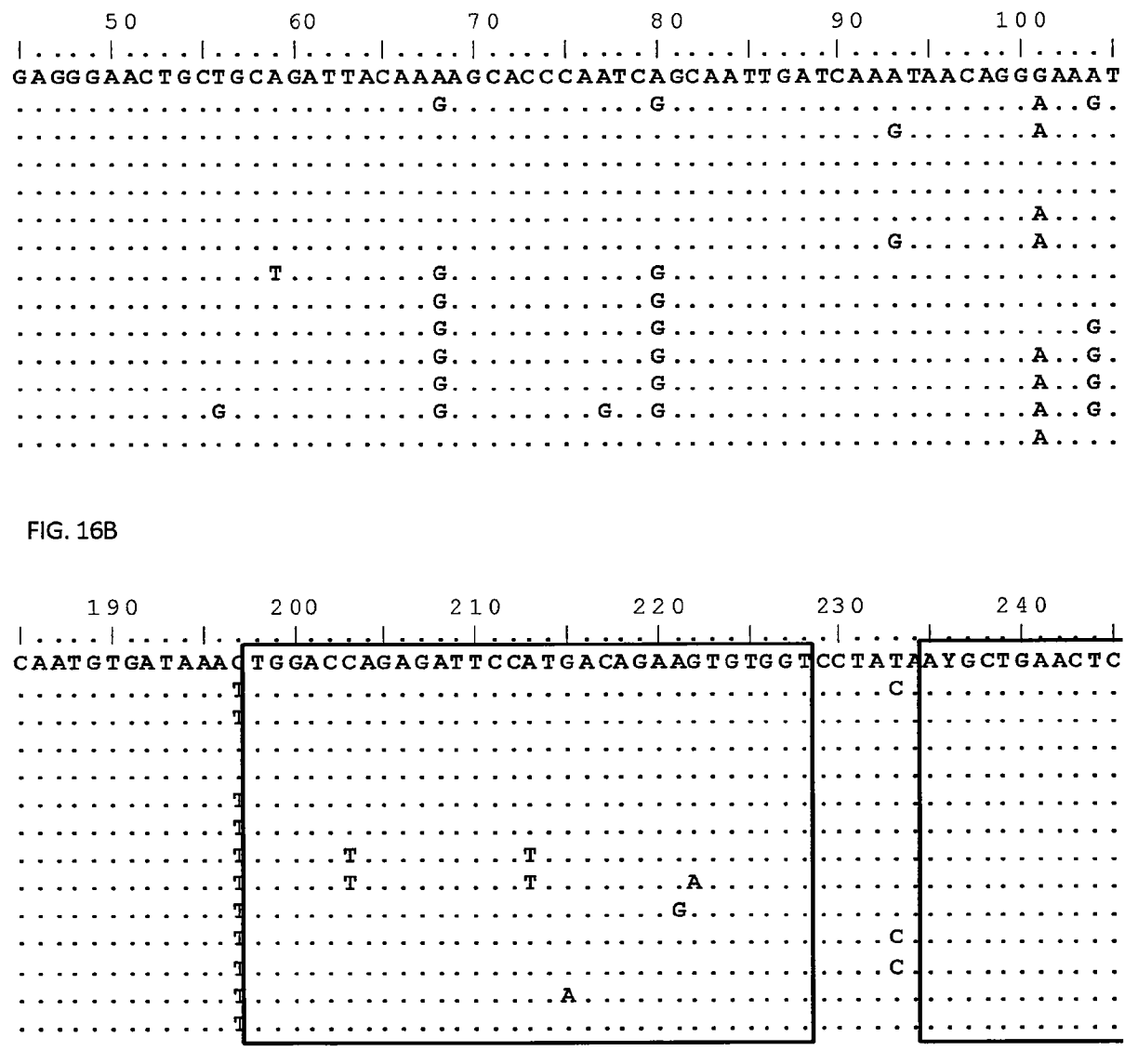
Figure 16C:
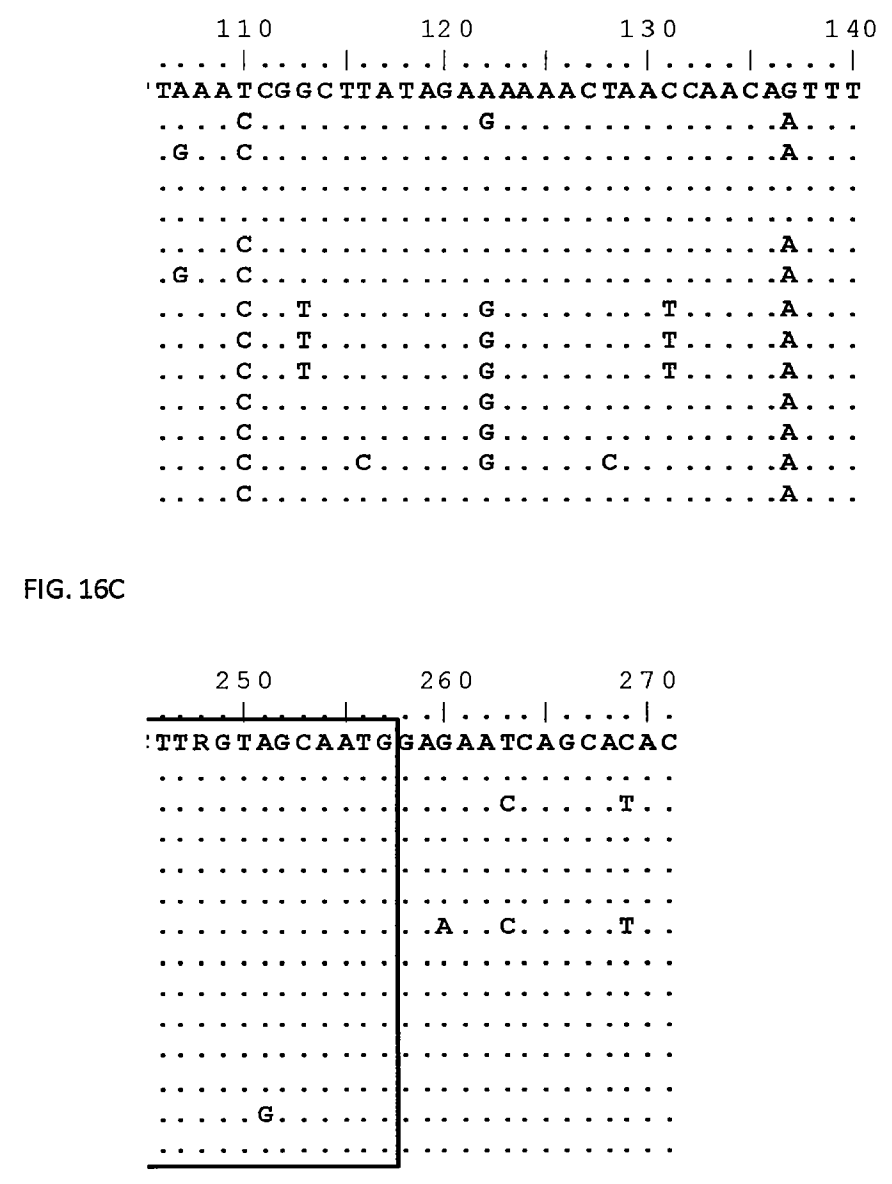

FIG. 16A-16C is a table showing the consensus sequence and variations present in the specified influenza isolates for the region of the influenza subtype European H7 HA gene (SEQ ID NO: 49) used to design the disclosed influenza subtype European H7 specific probes and primers.

FIG. 17A-17I is a table showing the consensus sequence and variations present in the specified influenza isolates for the region of the influenza subtype Asian H9 HA gene (SEQ ID NO: 50) used to design the disclosed influenza subtype Asian H9 specific probes and primers.

DETAILED DESCRIPTION

I. Explanation of Terms

Figure 1:
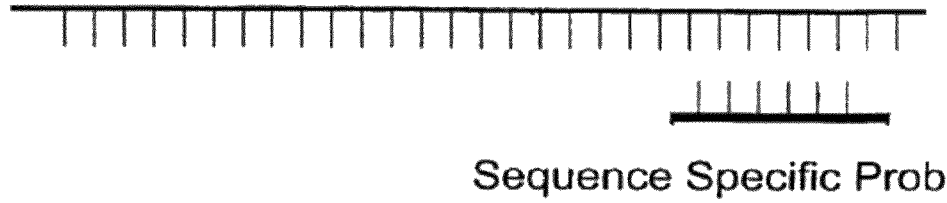
FIG. 1 is a schematic representation of a generalized procedure for hybridizing an influenza specific probe to an influenza nucleic acid.
Figure 1:

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a probe" means "including a probe" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: A living multi-cellular vertebrate or invertebrate organism, a category that includes, for example, mammals and birds. The term mammal includes both human and non-human mammals. Similarly, the term "subject" includes both human and veterinary subjects, such as birds.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR; real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA.

Change: To become different in some way, for example to be altered, such as increased or decreased. A detectable change is one that can be detected, such as a change in the intensity, frequency or presence of an electromagnetic signal, such as fluorescence. In some examples, the detectable change is a reduction in fluorescence intensity. In some examples, the detectable change is an increase in fluorescence intensity.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Detect: To determine if an agent (such as a signal or particular nucleotide or amino acid) is present or absent. In some examples, this can further include quantification. For example, use of the disclosed probes in particular examples permits detection of a fluorophore, for example detection of a signal from an acceptor fluorophore, which can be used to determine if a nucleic acid corresponding to nucleic acid of an influenza virus is present.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite a donor but not an acceptor fluorophore.

Emission or emission signal: The light of a particular wavelength generated from a fluorophore after the fluorophore absorbs light at its excitation wavelengths.

Excitation or excitation signal: The light of a particular wavelength necessary to excite a fluorophore to a state such that the fluorophore will emit a different (such as a longer) wavelength of light.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes disclosed herein are known to those of skill in the art and include those provided in U.S. Pat. No. 5,866,366 to Nazarenko et al., such as 4-acetamido-4'-isothiocyanatostilbene-2,2' disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl) maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; 6-carboxy-X-rhodamine (ROX); Texas Red; Cy3; Cy5, VIC® (Applied Biosystems); LC Red 640; LC Red 705; and Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes, such as Hyb-Probes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers.

Figure 2:
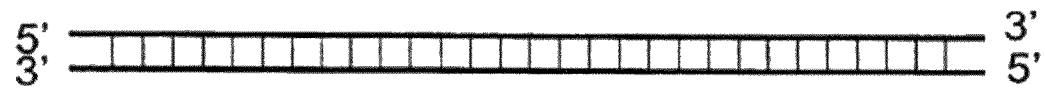
FIG. 2 is a schematic representation of a generalized procedure for hybridizing an influenza specific probe to an influenza nucleic acid, wherein the influenza nucleic acid is initially a double stranded nucleic acid.
Figure 2:
Figure 2:
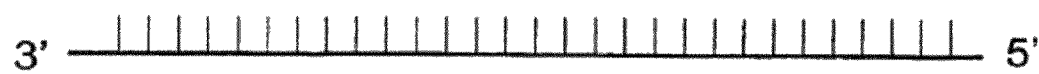
Figure 2:
Figure 2:

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as an influenza nucleic acid. For example, a probe or primer (such as any of SEQ ID NOS:3-38) having some homology to an influenza nucleic acid molecule will form a hybridization complex with an influenza nucleic acid molecule (such as any of SEQ ID NOS:42-50). Hybridization occurs between a single stranded probe and a single stranded target nucleic acid (such as an influenza nucleic acid), as illustrated in FIG. 1. When the target nucleic acid is initially one strand of a duplex nucleic acid the duplex must be melted (at least partially) for the probe to hybridize. This situation is illustrated in FIG. 2.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

| Very High Stringency (detects sequences that share at least 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share at least 80% identity) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share at least 50% identity) | |
|---|---|
| Hybridization: | 6x SSC at RT to 55° C. for 16-20 hours |
| Wash at least twice: | 2x-3x SSC at RT to 55° C. for 20-30 minutes each. |

The probes and primers disclosed herein can hybridize to influenza nucleic acids under low stringency, high stringency, and very high stringency conditions.

Influenza Virus: Influenza viruses are enveloped negative-sense viruses belonging to the orthomyxoviridae family. Influenza viruses are classified on the basis of their core proteins into three distinct types: A, B, and C. Within these broad classifications, subtypes are further divided based on the characterization of two antigenic surface proteins hemagglutinin (HA or H) and neuraminidase (NA or N). While B and C type influenza viruses are largely restricted to humans, influenza A viruses are pathogens of a wide variety of species including humans, non-human mammals, and birds. Periodically, non-human strains, particularly of avian influenza, have infected human populations, in some cases causing severe disease with high mortality. Recombination between such avian strains and human strains in coinfected individuals has given rise to recombinant influenza viruses to which immunity is lacking in the human population, resulting in influenza pandemics. Three such pandemics occurred during the twentieth century (pandemics of 1918, 1957, and 1968) and resulted in numerous deaths world-wide.

Influenza viruses have a segmented single-stranded (negative or antisense) genome. The influenza virion consists of an internal ribonucleoprotein core containing the single-stranded RNA genome and an outer lipoprotein envelope lined by a matrix protein. The segmented genome of influenza consists of eight linear RNA molecules that encode ten polypeptides. Two of the polypeptides, HA and NA include the primary antigenic determinants or epitopes required for a protective immune response against influenza. Based on the antigenic characteristics of the HA and NA proteins, influenza strains are classified into subtypes. For example, recent outbreaks of avian influenza in Asia have been categorized as H5N1, H7N7, and H9N2 based on their HA and NA phenotypes.

HA is a surface glycoprotein which projects from the lipoprotein envelope and mediates attachment to and entry into cells. The HA protein is approximately 566 amino acids in length, and is encoded by an approximately 1780 base polynucleotide sequence of segment 4 of the genome. Polynucleotide and amino acid sequences of HA (and other influenza antigens) isolated from recent, as well as historic, avian influenza strains can be found, for example in the GENBANK® database (available on the world wide web at ncbi.nlm.nih.gov/entrez) or the Influenza Sequence Database of Los Alamos National Laboratories (LANL) (available on the world wide web at http://www.flu.lanl.gov). For example, recent avian H1 subtype HA sequences include: AY038014, and J02144; recent avian H3 subtype HA sequences include: AY531037, M29257, and U97740; H5 subtype HA sequences include: AY075033, AY075030, AY818135, AF046097, AF046096, and AF046088; recent H7 subtype HA sequences include: AJ704813, AJ704812, and Z47199; and, recent avian H9 subtype HA sequences include: AY862606, AY743216, and AY664675.

In addition to the HA antigen, which is the predominant target of neutralizing antibodies against influenza, the neuraminidase (NA) envelope glycoprotein is also a target of the protective immune response against influenza. NA is an approximately 450 amino acid protein encoded by an approximately 1410 nucleotide sequence of influenza genome segment 6. Recent pathogenic avian strains of influenza have belonged to the N1, N7 and N2 subtypes. Exemplary NA polynucleotide and amino acid sequences include for example, N1: AY651442, AY651447, and AY651483; N7: AY340077, AY340078 and AY340079; and, N2: AY664713, AF508892, and AF508588.

The remaining segments of the influenza genome encode the internal proteins. PB2 is a 759 amino acid polypeptide which is one of the three proteins which comprise the RNA-dependent RNA polymerase complex. PB2 is encoded by approximately 2340 nucleotides of the influenza genome segment 1. The remaining two polymerase proteins, PB1, a 757 amino acid polypeptide, and PA, a 716 amino acid polypeptide, are encoded by a 2341 nucleotide sequence and a 2233 nucleotide sequence (segments 2 and 3), respectively.

Segment 5 consists of about 1565 nucleotides encoding an about 498 amino acid nucleoprotein (NP) protein that forms the nucleocapsid. Segment 7 consists of an about 1027 nucleotide sequence of the M gene, which encodes the two matrix proteins; an about 252 amino acid M1 protein, and an about 96 amino acid M2 protein, which is translated from a spliced variant of the M RNA. Segment 8 consists of the NS gene, which encodes two different non-structural proteins, NS1 and NS2.

Isolated: An "isolated" biological component (such as a nucleic acid) has been substantially separated or purified away from other biological components in which the component naturally occurs, such as other chromosomal and extra-chromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acids, such as probes and primers. Isolated does not require absolute purity, and can include nucleic acid molecules that are at least 50% isolated, such as at least 75%, 80%, 90%, 95%, 98%, 99% or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Nucleic acid (molecule or sequence): A deoxyribonucleotide or ribonucleotide polymer including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can also include analogs of natural nucleotides, such as labeled nucleotides. In one example, a nucleic acid is an influenza nucleic acid, which can include nucleic acids purified from influenza viruses as well as the amplification products of such nucleic acids.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine amongst others.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of an influenza nucleic acid), wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of an influenza nucleic acid) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence (such as the influenza nucleic acid sequences set forth as SEQ ID NOS: 42-50), for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: A probe comprises an isolated nucleic acid capable of hybridizing to a target nucleic acid (such as an influenza nucleic acid). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al, *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 20 nucleotides in length, such as at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 20-50 nucleotides, 20-40 nucleotides, or 20-30 nucleotides.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the *E. Coli* DNA polymerase I, specifically the Klenow fragment which has 3' to 5' exonuclease activity, Taq polymerase, reverse transcriptase (such as HIV-1 RT), *E. Coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Quantitating a nucleic acid molecule: Determining or measuring a quantity (such as a relative quantity) of nucleic acid molecules present, such as the number of amplicons or the number of nucleic acid molecules present in a sample. In particular examples, it is determining the relative amount or actual number of nucleic acid molecules present in a sample.

Quenching of fluorescence: A reduction of fluorescence. For example, quenching of a fluorophore's fluorescence occurs when a quencher molecule (such as the fluorescence quenchers listed above) is present in sufficient proximity to the fluorophore that it reduces the fluorescence signal (for example, prior to the binding of a probe to an influenza nucleic acid sequence, when the probe contains a fluorophore and a quencher).

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as an influenza nucleic acid) and/or quantitate the initial amounts of a target nucleic acid sequence. In some examples, real time PCR is real time reverse transcriptase PCR (rt RT-PCR).

Figure 4:
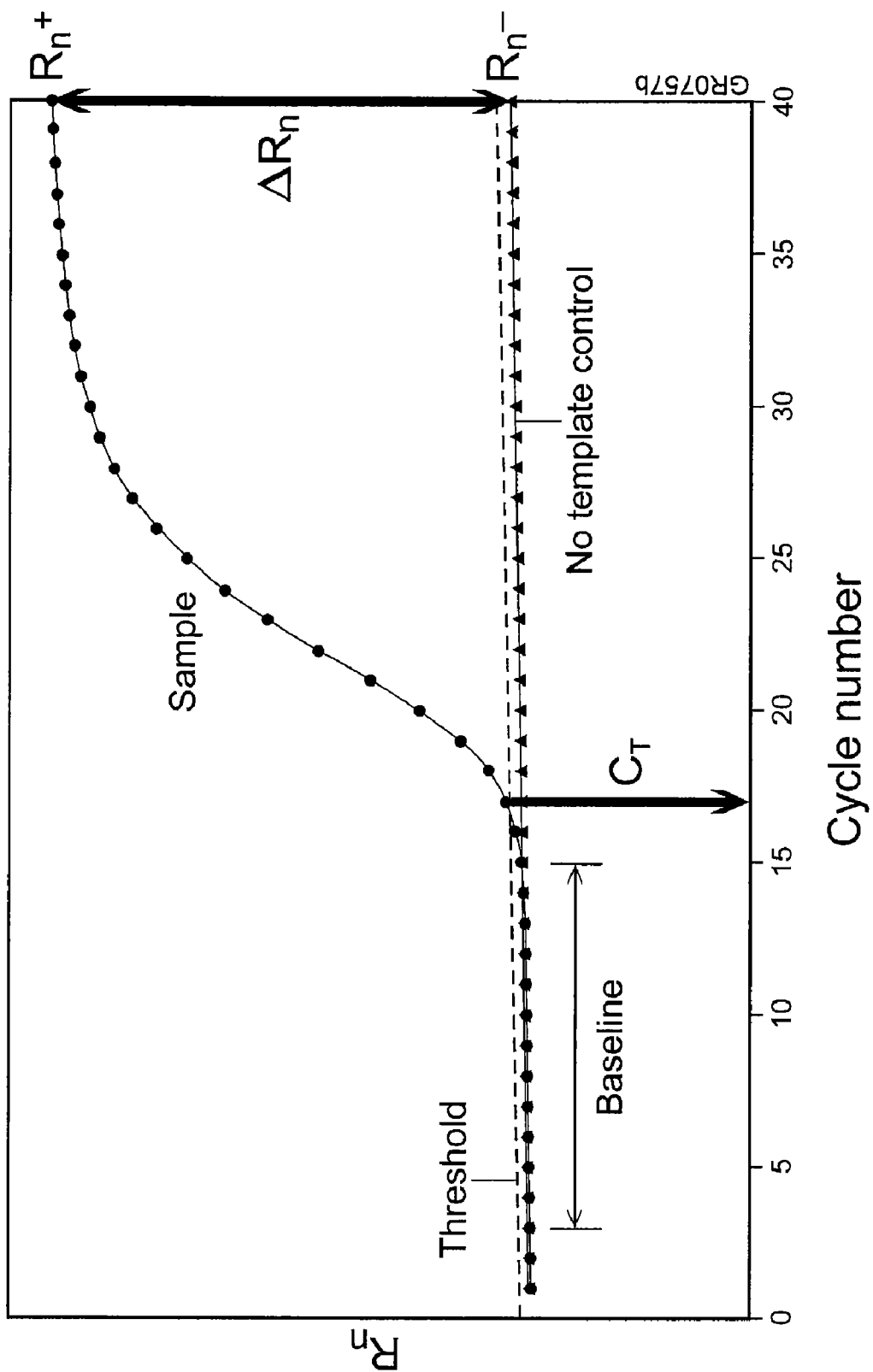
FIG. 4 is a graph of theoretical data generated from real-time reverse transcriptase polymerase chain reaction (rt RT-PCR) using TAQMAN® probes.

In some examples, the amount of amplified target nucleic acid (such as an influenza nucleic acid) is detected using a labeled probe, such as a probe labeled with a fluorophore, for example a TAQMAN® probe. In this example, the increase in fluorescence emission is measured in real time, during the course of the RT-PCR. This increase in fluorescence emission is directly related to the increase in target nucleic acid amplification (such as influenza nucleic acid amplification). In some examples, the change in fluorescence (dRn) is calculated using the equation $dRn=Rn^+ - Rn^-$, with $Rn^+$ being the fluorescence emission of the product at each time point and $Rn^-$ being the fluorescence emission of the baseline. The dRn values are plotted against cycle number, resulting in amplification plots for each sample as illustrated in FIG. 4. With reference to FIG. 4, the threshold value (Ct) is the PCR cycle number at which the fluorescence emission (dRn) exceeds a chosen threshold, which is typically 10 times the standard deviation of the baseline (this threshold level can, however, be changed if desired).

Sample: A sample, such as a biological sample, is a sample obtained from a plant or animal subject. As used herein, biological samples include all clinical samples useful for detection influenza infection in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; bronchoalveolar levage; tracheal aspirates; sputum; nasopharyngeal aspirates; oropharyngeal aspirates; and saliva. In particular embodiments, the biological sample is obtained from an animal subject, such as in the form of bronchoalveolar levage, tracheal aspirates, sputum, nasopharyngeal aspirates, oropharyngeal aspirates, and saliva.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl Math.* 2:482, 1981; Needleman & Wunsch, *J. Mol. Biol* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol* 215: 403-10, 1990, presents a detailed consideration of sequence alignment methods and homology calculations.

The NCBI Basic Local Alignment Search Tool (BLAST) (Altschul et al., *J. Mot. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                            1                    20
Target Sequence:     atggtggacccggtgggctt        (SEQ ID NO: 1)
                     | || |||  ||||  |||| |
Identified Sequence: acgggggatccggcgggcct        (SEQ ID NO: 2)
```

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99% sequence identity to any of SEQ ID NOS: 3-38 are provided herein. One of skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Figure 3:
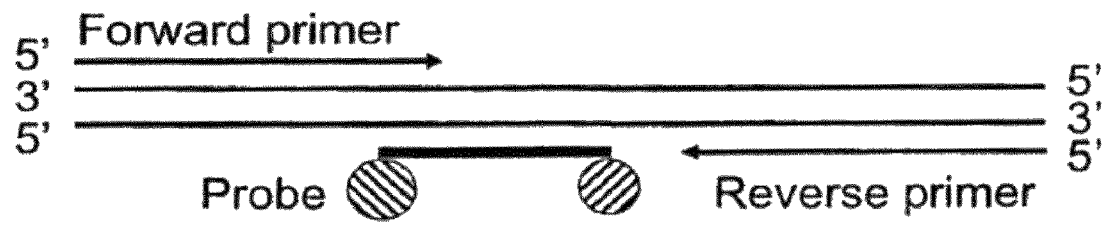
FIG. 3 is a schematic representation of a generalized procedure for hybridizing and detecting influenza using an influenza specific TAQMAN® probe.
Figure 3:
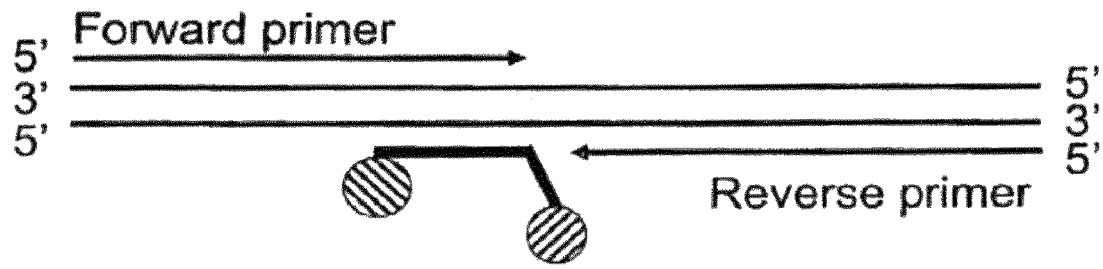
Figure 3:
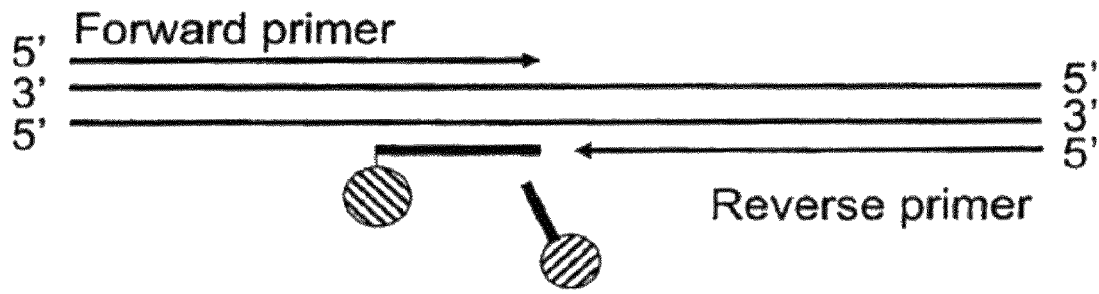
Figure 3:
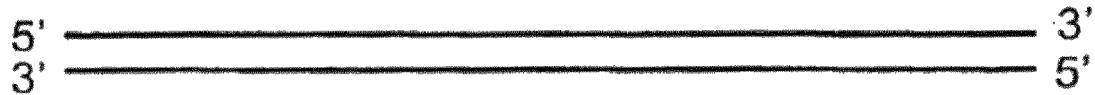

TAQMAN® probes: As illustrated in FIG. 3, a linear oligonucleotide probe with a 5' reporter fluorophore such as 6-carboxyfluorescein (FAM) and a 3' quencher fluorophore, such as BLACKHOLE QUENCHER™ 1 (BHQ™1). In the intact TAQMAN® probe, energy is transferred (via FRET) from the short-wavelength fluorophore to the long-wavelength fluorophore on the other end, quenching the short-wavelength fluorescence. After hybridization, the probe is susceptible to degradation by the endonuclease activity of a processing Taq polymerase. Upon degradation, FRET is interrupted, increasing the fluorescence from the short-wavelength fluorophore and decreasing fluorescence from the long-wavelength fluorophore.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA such as viral RNA), the amplification of which is intended. Purification or isolation of the target nucleic acid molecule, if needed, can be conducted by methods known to those in the art, such as by using a commercially available purification kit or the like. In one example, a target nucleic molecule is an influenza nucleic acid sequence.

II. Overview of Several Embodiments

Recent increased circulation of highly pathogenic avian influenza, such as H5N1, in avian populations together with sporadic human infections of highly pathogenic avian influenza has raised serious concerns about the pandemic threat of these viruses. The need exists for methods to rapidly detect and identify influenza viruses, for example to rapidly diagnose or determine the pandemic potential of viral samples, such as those obtained from a subject infected or believed to be infected with an influenza virus.

Disclosed herein are methods for the universal detection of all influenza type A and type B viruses as well as for the identification of the HA genes of influenza A viruses of human health significance including contemporary human H1 and H3, as well as Asian avian H5, Eurasian H7, North American H7, and Asian H9 viruses. The methods have been developed in one embodiment with a unique set of nucleic acid probes and/or primers that are surprisingly effective at detecting and discriminating between influenza type A, and type B and subtypes H1, H3, Asian avian H5, North American avian H7, European avian H7, and Asian avian H9 using a variety of conditions. This ability to rapidly screen and identify a virus from among these diverse groups is a significant public health advantage.

As disclosed herein, using sequence alignments of all known influenza viral sequences available, previously unknown regions of high sequence homology were discovered amongst the individual influenza viral types and subtypes. These regions were used to create the consensus sequences shown in FIGS. 9-17. Using these highly homologous regions as a starting point the disclosed probes and primers were designed such that they were surprisingly effective at recognizing genetically diverse influenza isolates within distinct viral types and/or subtypes. Because of the pandemic potential of influenza subtype Asian avian H5, two regions of the H5 HA gene regions of high sequence homology used to design redundant primers and probes.

Probes and Primers

Probes capable of hybridizing to and detecting the presence of influenza nucleic acids are disclosed. The disclosed probes are between 20 and 40 nucleotides in length, such as 20, 21, 22, 23, 24, 25, 26, 27, 28 29, 30, 31, 32, 32, 34, 35, 36, 37, 38, 39, or 40 nucleotides in length and are capable of hybridizing to the influenza virus nucleic acid. In several embodiments, a probe is capable of hybridizing under very high stringency conditions to an influenza virus nucleic acid sequence set forth as SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50.

In several embodiments, a probe capable of hybridizing to an influenza nucleic acid contains a nucleic acid sequence that is at least 95% identical, such as at least 96%, at least 97%, at least 98%, at least 99%, or even 100% identical to the nucleotide sequence set forth as SEQ ID NO:8, SEQ ID NO:11, SEQ ID NO:14, SEQ ID NO: 19, SEQ ID NO:24, SEQ ID NO:29, SEQ ID NO:32, SEQ ID NO:35, or SEQ ID NO:38. In several embodiments, a probe capable of hybridizing to an influenza nucleic acid consists essentially of a nucleic acid sequence set forth as SEQ ID NO:8, SEQ ID NO:11, SEQ ID NO: 14, SEQ ID NO: 19, SEQ ID NO:24, SEQ ID NO:29, SEQ ID NO:32, SEQ ID NO:35, or SEQ ID NO:38.

In several embodiments, the probe is influenza type specific. An influenza type specific probe is capable of hybridizing under stringent conditions (such as high stringency, or very high stringency conditions) to an influenza virus nucleic acid from a specific influenza type, such as influenza type A or type B. For example, a probe that is type specific for influenza type A (such as specific for an influenza type A M gene sequence, for example the nucleic acid sequence set forth as SEQ ID NO:42) is not type specific for influenza type B. Likewise, a probe that is type specific for influenza type B (such as specific for an influenza type B NS gene sequence, for example the nucleic acid sequence set forth as SEQ ID NO:43) is not type specific for influenza type A. In other words a nucleic acid probe that specifically hybridizes to an influenza type A nucleic acid (such as a nucleic acid that is at least a portion of the M gene from influenza type A) does not hybridize to an influenza type B nucleic acid; such nucleic acids would be type specific probes for influenza type A. Conversely, a nucleic acid probe that specifically hybridizes to an influenza type B nucleic acid (such as a nucleic acid that is at least a portion of the NS gene from influenza type B) does not hybridize to an influenza type A nucleic acid; such nucleic acids would be type specific probes for influenza type B. Thus, type specific probes can be used to discriminate the presence of influenza type A from influenza type B, or the converse. In some embodiments, the probe is capable of hybridizing under very high stringency conditions to a nucleic acid from influenza A, for example to an influenza type A nucleic acid from the M gene of influenza type A set forth as SEQ ID NO:42. In some embodiments, the probe is capable of hybridizing under very high stringency conditions to a nucleic acid from influenza B, for example to an influenza type B nucleic acid from the NS gene of influenza type B set forth as SEQ ID NO:43.

In some embodiments, the probe is specific for an influenza type A sequence. In a specific example, a probe specific for an influenza type A nucleic acid includes a nucleic acid sequence at least 95% identical to SEQ ID NO:8. In some embodiments, the probe is specific for an influenza type B sequence. In a specific example, a probe specific for an influenza type B nucleic acid includes a nucleic acid sequence at least 95% identical to SEQ ID NO:29.

In several embodiments, the probe is influenza subtype specific. An influenza subtype specific probe is capable of hybridizing under stringent conditions (such as high stringency, or very high stringency conditions) to an influenza virus nucleic acid from a specific influenza subtype, such as influenza subtype H1, H3, H5, North American H7, European H7, or Asian H9. Subtype specific probes can be used to detect the presence of and differentiate between the various influenza subtypes. Such probes are specific for one influenza subtype, for example specific for an influenza HA sequence that is subtype specific, such as an H1, H3, H5, North American H7, European H7, or Asian H9 sequence. In some examples, a probe that is subtype specific for influenza subtype H1 is not subtype specific for influenza subtype H3, H5, H7 (North American or European), or Asian H9. In another example, a probe that is subtype specific for influenza subtype H3 is not subtype specific for influenza subtype H1, H5, H7 (North American or European), or Asian H9. In another example, a probe that is subtype specific for influenza subtype H5 is not subtype specific for influenza subtype H1, H3, H7 (North American or European), or Asian H9. In another example, a probe that is subtype specific for influenza subtype North American H7 is not subtype specific for influenza subtype H1, H3, H5, European H7, or Asian H9. In another example, a probe that is subtype specific for influenza subtype European H7 is not subtype specific for influenza subtype H1, H3, H5, North American H7, or Asian H9. In yet another example, a probe that is subtype specific for influenza subtype Asian H9 is not subtype specific for influenza subtype H1, H3, H5, or H7 (North American or European). To put it another way a nucleic acid probe that specifically hybridizes to an influenza subtype H1 nucleic acid does not hybridize to an influenza subtype H3 or any other subtype nucleic acid, such nucleic acids would be type specific probes for influenza type H1. One of skill in the art would understand that the same trend would hold for the other subtype specific probes.

In some embodiments, the probe is specific for an influenza subtype H1 sequence, such as the nucleic acid sequence set forth as SEQ ID NO:44. In a specific example, a probe specific for an influenza subtype H1 nucleic acid includes a nucleic acid sequence at least 95% identical to SEQ ID NO:11. In some embodiments, the probe is specific for an influenza subtype H3 sequence, such as the nucleic acid sequence set forth as SEQ ID NO:45. In a specific example, a probe specific for an influenza subtype H3 nucleic acid includes a nucleic acid sequence at least 95% identical to SEQ ID NO:14. In some embodiments, the probe is specific for an influenza subtype H5 sequence, such as the nucleic acid sequence set forth as SEQ ID NO:46. In a specific example, a probe specific for an influenza subtype H5 nucleic acid includes a nucleic acid sequence at least 95% identical to SEQ ID NO:19. In another specific example, a probe specific for an influenza subtype H5 nucleic acid includes a nucleic acid sequence at least 95% identical to SEQ ID NO:24. In some embodiments, the probe is specific for an influenza subtype North American H7 sequence, such as the nucleic acid sequence set forth as SEQ ID NO:48. In a specific example, a probe specific for an influenza subtype North American H7 nucleic acid includes a nucleic acid sequence at least 95% identical to SEQ ID NO:32. In some embodiments, the probe is specific for an influenza subtype European H7 sequence, such as the nucleic acid sequence set forth as SEQ ID NO:49. In a specific example, a probe specific for an influenza subtype European H7 nucleic acid includes a nucleic acid sequence at least 95% identical to SEQ ID NO:32. In some embodiments, the probe is specific for an influenza subtype Asian H9 sequence, such as the nucleic acid sequence set forth as SEQ ID NO:50. In a specific example, a probe specific for an influenza subtype Asian H9 nucleic acid includes a nucleic acid sequence at least 95% identical to SEQ ID NO:38.

In some embodiments, the probe is detectably labeled, either with an isotopic or non-isotopic label, alternatively the target nucleic acid (such as an influenza nucleic acid) is labeled. Non-isotopic labels can, for instance, comprise a fluorescent or luminescent molecule, biotin, an enzyme or enzyme substrate or a chemical. Such labels are preferentially chosen such that the hybridization of the probe with target nucleic acid (such as an influenza nucleic acid) can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase.

In particular examples, the acceptor fluorophore (such as a fluorescence quencher) is attached to the 3' end of the probe and the donor fluorophore is attached to a 5' end of the probe. In another particular example, the acceptor fluorophore (such as a fluorescence quencher) is attached to a modified nucleotide (such as a T) and the donor fluorophore is attached to a 5' end of the probe.

Primers capable of hybridizing to and directing the amplification of influenza nucleic acids are disclosed. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or even 40 nucleotides in length. In several embodiments, a primer is capable of hybridizing under very high stringency conditions to an influenza virus nucleic acid sequence set forth as SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50, and directing the amplification of the influenza nucleic acid.

In several embodiments, a primer capable of hybridizing to and directing the amplification of an influenza nucleic acid contains a nucleic acid sequence that is at least 95% identical such as at least 96%, at least 97%, at least 98%, at least 99%, or even 100% identical to the nucleic acid sequence set forth as SEQ ID NO:3, SEQ ID NO:4, SEQ ID NO:9, SEQ ID NO:10, SEQ ID NO:12, SEQ ID NO:13, SEQ ID NO:17, SEQ ID NO: 18, SEQ ID NO: 22, SEQ ID NO:23, SEQ ID NO:26, SEQ ID NO:28, SEQ ID NO:30, SEQ ID NO:31, SEQ ID NO:33, SEQ ID NO:34, SEQ ID NO:36, or SEQ ID NO:37. In several embodiments, a primer capable of hybridizing to an influenza nucleic acid consists essentially of a nucleic acid sequence set forth as SEQ ID NO:3, SEQ ID NO:4, SEQ ID NO:9, SEQ ID NO:10, SEQ ID NO:12, SEQ ID NO:13, SEQ ID NO:17, SEQ ID NO: 18, SEQ ID NO: 22, SEQ ID NO:23, SEQ ID NO:26, SEQ ID NO:28, SEQ ID NO:30, SEQ ID NO:31, SEQ ID NO:33, SEQ ID NO:34, SEQ ID NO:36, or SEQ ID NO:37.

In several embodiments, the primer is influenza type specific. An influenza type specific primer is capable of hybridizing under stringent conditions (such as high stringency, or very high stringency conditions) to an influenza virus nucleic acid from a specific influenza type, such as influenza type A or type B. For example, a primer that is type specific for influenza type A is not type specific for influenza type B. Likewise, a primer that is type specific for influenza type B is not type specific for influenza type A. In other words a nucleic acid primer that specifically hybridizes to an influenza type A nucleic acid (such as a nucleic acid that is at least a portion of the M gene from influenza type A, for example the nucleic acid sequence set forth as SEQ ID NO:42) does not hybridize to an influenza type B nucleic acid, such nucleic acids would be type specific primers for influenza type A. Conversely, a nucleic acid primer that specifically hybridizes to an influenza type B nucleic acid (such as a nucleic acid that is at least a portion of the NS gene from influenza type B, for example the nucleic acid sequence set forth as SEQ ID NO:43) does not hybridize to an influenza type A nucleic acid, such nucleic acids would be type specific primers for influenza type A. Thus, type specific primers can be used to specifically amplify a nucleic acid from influenza type A or from influenza type B, but not both. In some embodiments, the primer is capable of hybridizing under very high stringency conditions to a nucleic acid from influenza A, for example to an influenza type A nucleic acid from the M gene of influenza type A set forth as SEQ ID NO:42. In some embodiments, the primer is capable of hybridizing under very high stringency conditions to a nucleic acid from influenza B, for example to an influenza type B nucleic acid from the NS gene of influenza type B set forth as SEQ ID NO:43.

In some embodiments, the primer is specific for an influenza type A sequence, such as an influenza type A M gene sequence. In a specific example, a primer specific for an influenza type A nucleic acid includes a nucleic acid sequence at least 95% identical to SEQ ID NO:3 or SEQ ID NO:4. In some embodiments, the primer is specific for an influenza type B sequence, such as an influenza type B NS gene sequence. In a specific example, a primer specific for an influenza type B nucleic acid includes a nucleic acid sequence at least 95% identical to SEQ ID NO:26 or SEQ ID NO:28.

In several embodiments, the primer is influenza subtype specific. An influenza subtype specific primer is capable of hybridizing under stringent conditions (such as high stringency, or very high stringency conditions) to an influenza virus nucleic acid from a specific influenza subtype, such as influenza subtype H1, H3, H5, North American H7, European H7 or Asian H9. Such primers are specific for one influenza subtype, for example specific for an influenza HA sequence that is subtype specific, such as an H1, H3, H5, North American H7, European H7 or Asian H9 HA nucleic acid sequence. Subtype specific primers can be used to amplify sequences specific to the various influenza subtypes. In one example, a primer that is subtype specific for influenza subtype H1 is not subtype specific for influenza subtype H3, H5, H7 (North American or European), or Asian H9. A primer that is subtype specific for influenza subtype H3 is not subtype specific for influenza subtype H1, H5, H7 (North American or European), or Asian H9. A primer that is subtype specific for influenza subtype H5 is not subtype specific for influenza subtype H1, H3, H7 (North American or European), or Asian H9. A primer that is subtype specific for influenza subtype North American H7 is not subtype specific for influenza subtype H1, H3, H5, European H7, or Asian H9. A primer that is subtype specific for influenza subtype European H7 is not subtype specific for influenza subtype H1, H3, H5, North American H7, or Asian H9. A primer that is subtype specific for influenza subtype Asian H9 is not subtype specific for influenza subtype H1, H3, H5, or H7 (North American or European). To put it another way a nucleic acid primer that specifically hybridizes to an influenza subtype H1 nucleic acid does not hybridize to an influenza subtype H3 or any other subtype nucleic acid, such nucleic acids would be type specific primers for influenza type H1. One of skill in the art would understand that this trend holds for the other subtype specific primers.

In some embodiments, the primer is specific for an influenza subtype H1 sequence, such as the nucleic acid sequence set forth as SEQ ID NO:44. In a specific example, a primer specific for an influenza subtype H1 nucleic acid includes a nucleic acid sequence at least 95% identical to SEQ ID NO:9 or SEQ ID NO:10. In some examples, the primer is specific for an influenza subtype H3 sequence, such as the nucleic acid sequence set forth as SEQ ID NO:45. In a specific example, a primer specific for an influenza subtype H3 nucleic acid includes a nucleic acid sequence at least 95% identical to SEQ ID NO:12 or SEQ ID NO:13. In some examples, the primer is specific for an influenza subtype H5 sequence, such as the nucleic acid sequence set forth as SEQ ID NO:46. In a specific example, a primer specific for an influenza subtype H5 nucleic acid includes a nucleic acid sequence at least 95% identical to SEQ ID NO: 17 or SEQ ID NO: 18. In a specific example, a primer specific for an influenza subtype H5 nucleic acid includes a nucleic acid sequence at least 95% identical to SEQ ID NO:22 or SEQ ID NO:23. In some examples, the primer is specific for an influenza subtype North American H7 sequence, such as the nucleic acid sequence set forth as SEQ ID NO:48. In a specific example, a primer specific for an influenza subtype North American H7 nucleic acid includes a nucleic acid sequence at least 95% identical to SEQ ID NO:30 or SEQ ID NO:31. In some examples, the primer is specific for an influenza subtype European H7 sequence, such as the nucleic acid sequence set forth as SEQ ID NO:49. In a specific example, a primer specific for an influenza subtype European H7 nucleic acid includes a nucleic acid sequence at least 95% identical to SEQ ID NO:33 or SEQ ID NO:34. In some examples, the primer is specific for an influenza subtype Asian H9 sequence, such as the nucleic acid sequence set forth as SEQ ID NO:50. In a specific example, a primer specific for an influenza subtype Asian H9 nucleic acid includes a nucleic acid sequence at least 95% identical to SEQ ID NO:36 or SEQ ID NO:38.

In certain embodiments the primers are a set of primers, such as a pair of primers, capable of hybridizing to and amplifying an influenza nucleic acid. Such a set primers comprises at least one forward primer and a least one reverse primer, where the primers are specific for the amplification of an influenza type or subtype nucleic acid. In some examples, the set of primers includes a pair of primers that is specific for the amplification of influenza type A, type B, subtype H1, subtype H3, subtype H5, subtype North American H7, subtype European H7, or subtype Asian H9.

In certain examples, the pair of primers is specific for the amplification of an influenza type A nucleic acid and includes a forward primer at least 95% identical to SEQ ID NO:3 and a reverse primer at least 95% identical to SEQ ID NO:4. In other examples, the pair of primers is specific for the amplification of an influenza subtype H1 and includes a forward primer at least 95% identical to SEQ ID NO:9 and a reverse primer at least 95% identical to SEQ ID NO: 10. In other examples, the pair of primers is specific for the amplification of an influenza subtype H3 and includes a forward primer at least 95% identical to SEQ ID NO: 12 and a reverse primer at least 95% identical to SEQ ID NO:13. In other examples, the pair of primers is specific for the amplification of an influenza subtype H5 and includes a forward primer at least 95% identical to SEQ ID NO: 17 and a reverse primer at least 95% identical to SEQ ID NO: 18. In other examples, the pair of primers is specific for the amplification of an influenza subtype H5 and includes a forward primer at least 95% identical to SEQ ID NO:22 and a reverse primer at least 95% identical to SEQ ID NO:23. In other examples, the pair of primers is specific for the amplification of an influenza subtype type B and includes a forward primer at least 95% identical to SEQ ID NO:26 and a reverse primer at least 95% identical to SEQ ID NO:28. In other examples, the pair of primers is specific for the amplification of an influenza subtype North American H7 and includes a forward primer at least 95% identical to SEQ ID NO:30 and a reverse primer at least 95% identical to SEQ ID NO: 31. In other examples, the pair of primers is specific for the amplification of an influenza subtype European H7 and includes a forward primer at least 95% identical to SEQ ID NO:33 and a reverse primer at least 95% identical to SEQ ID NO:34. In other examples, the pair of primers is specific for the amplification of an influenza subtype Asian H9 and includes a forward primer at least 95% identical to 95% identical to SEQ ID NO:36 and a reverse primer at least 95% identical to SEQ ID NO:38.

Although exemplary probes and primers are provided in SEQ ID NOS:3-38, one skilled in the art will appreciate that the primer and/or probe sequence can be varied slightly by moving the probes a few nucleotides upstream or downstream from the nucleotide positions that they hybridize to on the influenza nucleic acid, provided that the probe and or primer is still specific for the influenza sequence, such as specific for the type or subtype of the influenza sequence, for example specific for SEQ ID NO:42, SEQ ID NO:43, SEQ ID NO:44, SEQ ID NO:45, SEQ ID NO:46, SEQ ID NO:47, SEQ ID NO:48, SEQ ID NO:49, or SEQ ID NO:50. For example, one of skill in the art will appreciate that by analyzing the consensus sequences shown in FIGS. 9-17 that variations of the probes and primers disclosed as SEQ ID NOS:3-38 can by made by "sliding" the probes and/or primers a few nucleotides 5' or 3' from their positions, and that such variation will still be specific for the influenza viral type and/or subtype.

Also provided by the present application are probes and primers that include variations to the nucleotide sequences shown in any of SEQ ID NOS:3-38, as long as such variations permit detection of the influenza nucleic acid, such as an influenza type or subtype. For example, a probe or primer can have at least 95% sequence identity such as at least 96%, at least 97%, at least 98%, at least 99% to a nucleic acid consisting of the sequence shown in any of SEQ ID NOS:3-38. In such examples, the number of nucleotides does not change, but the nucleic acid sequence shown in any of SEQ ID NOS: 3-38 can vary at a few nucleotides, such as changes at 1, 2, 3, or 4 nucleotides, for example by changing the nucleotides as shown in the tables presented in FIGS. 9-17.

The present application also provides probes and primers that are slightly longer or shorter than the nucleotide sequences shown in any of SEQ ID NOS:3-38, as long as such deletions or additions permit detection of the desired influenza nucleic acid, such as an influenza type or subtype. For example, a probe can include a few nucleotide deletions or additions at the 5'- or 3'-end of the probe shown in any of SEQ ID NOS:3-38, such as addition or deletion of 1, 2, 3, or 4 nucleotides from the 5'- or 3'-end, or combinations thereof (such as a deletion from one end and an addition to the other end). In such examples, the number of nucleotides changes. One of skill in the art will appreciate that the consensus sequences shown in FIGS. 9-17 (SEQ ID NOS:42-50) provide sufficient guidance as to what additions and/or subtractions can be made, while still maintaining specificity for the influenza viral type and/or subtype.

Detection and Identification of Influenza

A major application of the influenza virus specific primers and probes disclosed herein is for the detection, typing and subtyping of influenza viruses in a sample, such as a biological sample obtained from a subject that has or is suspected of having an influenza infection. Thus, the disclosed methods can be used to diagnose if a subject has an influenza infection and/or discriminate between the viral type and/or subtype the subject is infected with.

Methods for the detection of influenza nucleic acids are disclosed, for example to determine if a subject is infected with an influenza virus. Methods also are provided for determining the type and/or subtype of the influenza viral nucleic acid, for example to determine the type and/or subtype of influenza virus a subject is infected with.

The methods described herein may be used for any purpose for which detection of influenza is desirable, including diagnostic and prognostic applications, such as in laboratory and clinical settings. Appropriate samples include any conventional environmental or biological samples, including clinical samples obtained from a human or veterinary subject, such as a bird. Suitable samples include all biological samples useful for detection of viral infection in subjects, including, but not limited to, cells, tissues (for example, lung, liver and kidney), bone marrow aspirates, bodily fluids (for example, blood, serum, urine, cerebrospinal fluid, bronchoalveolar levage, tracheal aspirates, sputum, nasopharyngeal aspirates, oropharyngeal aspirates, saliva), eye swabs, cervical swabs, vaginal swabs, rectal swabs, stool, and stool suspensions. Particularly suitable samples include samples obtained from bronchoalveolar levage, tracheal aspirates, sputum, nasopharyngeal aspirates, oropharyngeal aspirates, or saliva. Standard techniques for acquisition of such samples are available. See for example, Schluger et al, *J. Exp. Med.* 176:1327-33 (1992); Bigby et al., *Am. Rev. Respir. Dis.* 133:515-18 (1986); Kovacs et al, *NEJM* 318:589-93 (1988); and Ognibene et al, *Am. Rev. Respir. Dis.* 129:929-32 (1984).

Detecting an influenza nucleic acid in a sample involves contacting the sample with at least one of the influenza specific probes disclosed herein that is capable of hybridizing to an influenza virus nucleic acid under conditions of very high stringency (such as a nucleic acid probe capable of hybridizing under very high stringency conditions to an influenza nucleic acid sequence set forth as SEQ ID NOS:42-50, for example a nucleic acid sequence at least 95% identical to the nucleotide sequence set forth as one of SEQ ID NO: 8, SEQ ID NO:11, SEQ ID NO:14, SEQ ID NO:19, SEQ ID NO:24, SEQ ID NO:29, SEQ ID NO:32, SEQ ID NO:35, and SEQ ID NO:38), and detecting hybridization between the influenza virus nucleic acid and the probe. Detection of hybridization between the probe influenza nucleic acid indicates the presence of the influenza nucleic acid in the sample.

By using influenza type specific probes, the disclosed methods can be used to detect the presence of influenza types in the sample. For example, by contacting the sample with an influenza type A specific probe, such as a probe capable of hybridizing under very high stringency conditions to an influenza nucleic acid sequence set forth as SEQ ID NO:42, for example a nucleic acid sequence of at least 95% identical to SEQ ID NO:8, and detecting the hybridization of the influenza type A specific probe to the influenza nucleic acid, the presence of influenza type A is detected. Alternatively, contacting the sample with a probe specific for an influenza type B nucleic acid, such as a probe capable of hybridizing under very high stringency conditions to an influenza nucleic acid sequence set forth as SEQ ID NO:43, for example a nucleic acid sequence of at least 95% identical to SEQ ID NO:29, and detecting the hybridization between the probe and the influenza nucleic acid indicates influenza type B is present. Thus, these disclosed methods can be used discriminate between the presence of influenza type A or type B in a sample.

The influenza subtype specific probes disclosed herein can be used to detect the presence of and discriminate between influenza subtypes in a sample. For example, contacting a sample with a probe specific for influenza subtype H1, such as a probe capable of hybridizing under very high stringency conditions to an influenza nucleic acid sequence set forth as SEQ ID NO:44, for example a nucleic acid at least 95% identical to the nucleotide sequence set forth as SEQ ID NO: 11, and detecting the hybridization between the probe and the influenza nucleic acid indicates that influenza subtype H1 is present. In another example, contacting a sample with a probe specific for influenza subtype H3, such as a probe capable of hybridizing under very high stringency conditions to an influenza nucleic acid sequence set forth as SEQ ID NO:45, for example a nucleic acid at least 95% identical to the nucleotide sequence set forth as SEQ ID NO: 14, and detecting the hybridization between the probe and the influenza nucleic acid indicates the presence of influenza subtype H3. In another example, contacting a sample with a probe specific for influenza subtype H5, such as a probe capable of hybridizing under very high stringency conditions to an influenza nucleic acid sequence set forth as SEQ ID NO:46, for example a nucleic acid at least 95% identical to the nucleotide sequence set forth as SEQ ID NO: 19, and detecting the hybridization between the probe and the influenza nucleic acid indicates the presence of influenza subtype H5. In another example, contacting a sample with a probe specific for influenza subtype H5, such as a probe capable of hybridizing under very high stringency conditions to an influenza nucleic acid sequence set forth as SEQ ID NO:47, for example a nucleic acid at least 95% identical to the nucleotide sequence set forth as SEQ ID NO:24, and detecting the hybridization between the probe and the influenza nucleic acid indicates the presence of influenza subtype H5. In another example, contacting a sample with a probe specific for influenza subtype North American H7, such as a probe capable of hybridizing under very high stringency conditions to an influenza nucleic acid sequence set forth as SEQ ID NO:48, for example a nucleic acid at least 95% identical to the nucleotide sequence set forth as SEQ ID NO:32, and detecting the hybridization between the probe and the influenza nucleic acid indicates the presence of influenza subtype North American H7. In yet another example, contacting a sample with a probe specific for influenza subtype European H7, such as a probe capable of hybridizing under very high stringency conditions to an influenza nucleic acid sequence set forth as SEQ ID NO:49, for example a nucleic acid at least 95% identical to the nucleotide sequence set forth as SEQ ID NO:35, and detecting the hybridization between the probe and the influenza nucleic acid indicates the presence of influenza subtype European H7. In still another example, contacting a sample with a probe specific for influenza subtype Asian H9, such as a probe capable of hybridizing under very high stringency conditions to an influenza nucleic acid sequence set forth as SEQ ID NO:50, for example a nucleic acid at least 95% identical to the nucleotide sequence set forth as SEQ ID NO:38, and detecting the hybridization between the probe and the influenza nucleic acid indicates the presence of influenza subtype Asian H9.

In some embodiments, detecting the presence of an influenza nucleic acid sequence in a sample includes the extraction of influenza RNA. RNA extraction relates to releasing RNA from a latent or inaccessible form in a virion, cell or sample and allowing the RNA to become freely available. In such a state, it is suitable for effective detection and/or amplification of the influenza nucleic acid. Releasing RNA may include steps that achieve the disruption of virions containing viral RNA, as well as disruption of cells that may harbor such virions. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular or viral components, wherein such components may be either particulate or dissolved.

One of ordinary skill in the art will know suitable methods for extracting RNA from a sample; such methods will depend upon, for example, the type of sample in which the influenza RNA is found. For example, the RNA may be extracted using guanidinium isothiocyanate, such as the single-step isolation by acid guanidinium isothiocyanate-phenol-chloroform extraction of Chomczynski et al. (*Anal Biochem*. 162:156-59, 1987). The sample can be used directly or can be processed, such as by adding solvents, preservatives, buffers, or other compounds or substances. Viral RNA can be extracted using standard methods. For instance, rapid RNA preparation can be performed using a commercially available kit (such as the Roche MagNA Pure Compact Nucleic Acid Isolation Kit I, QIAAMP® Viral RNA Mini Kit, QIAAMP® MinElute Virus Spin Kit or RNEASY® Mini Kit (QIAGEN); NUCLISENS® NASBA Diagnostics (bioMérieux); MASTERPURE™ Complete DNA and RNA Purification Kit (EPICENTRE). Alternatively, an influenza virion may be disrupted by a suitable detergent in the presence of proteases and/or inhibitors of ribonuclease activity. Additional exemplary methods for extracting RNA are found, for example, in World Health Organization, *Manual for the virological investigation of polio*, World Health Organization, Geneva, 2001.

In some embodiments, the probe is detectably labeled, either with an isotopic or non-isotopic label; in alternative embodiments, the influenza nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some embodiments, influenza nucleic acids present in a sample are amplified prior to using a hybridization probe for detection. For instance, it can be advantageous to amplify a portion of the influenza nucleic acid, then detect the presence of the amplified influenza nucleic acid. For example, to increase the number of nucleic acids that can be detected, thereby increasing the signal obtained. Influenza specific nucleic acid primers can be used to amplify a region that is at least about 50, at least about 60, at least about 70, at least about 80 at least about 90, at least about 100, at least about 200, or more base pairs in length to produce amplified influenza specific nucleic acids. Any nucleic acid amplification method can be used to detect the presence of influenza in a sample. In one specific, non-limiting example, polymerase chain reaction (PCR) is used to amplify the influenza nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the influenza nucleic acid. In a specific example, the influenza virus nucleic acid is amplified by rt RT-PCR. Techniques for nucleic acid amplification are well-known to those of skill in the art.

Typically, at least two primers are utilized in the amplification reaction, however it is envisioned that one primer can be utilized, for example to reverse transcribe a single stranded nucleic acid such as a single-stranded influenza RNA. Amplification of the influenza nucleic acid involves contacting the influenza nucleic acid with one or more primers that are capable of hybridizing to and directing the amplification of an influenza nucleic acid (such as a nucleic acid capable of hybridizing under very high stringency conditions to an influenza nucleic acid set forth as SEQ NO:42-50, for example a primer that is least 95% identical to the nucleotide sequence set forth as one of SEQ ID NO:8, SEQ ID NO:11, SEQ ID NO: 14, SEQ ID NO: 19, SEQ ID NO:24, SEQ ID NO:29, SEQ ID NO:32, SEQ ID NO:35, and SEQ ID NO:38). In some embodiments, the sample is contacted with at least one primer that is specific for an influenza type or subtype, such as those disclosed herein.

In some embodiments, the sample is contacted with at least one pair of primers that include a forward and reverse primer that both hybridize to an influenza nucleic acid specific for an influenza viral type and or subtype, such as influenza type A, type B, subtype H3, H5, H7 (North American or European), or Asian H9. Examples of suitable primer pairs for the amplification of influenza type and/or subtype specific nucleic acids are described above.

Any type of thermal cycler apparatus can be used for the amplification of the influenza nucleic acids and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENE-AMP® PCR System 9700 (Applied Biosystems; Foster City, Calif.). For real-time PCR, any type of real-time thermocycler apparatus can be used. For example, a BioRad icycler iQ™, LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), or an MX4000™, MX3000™ or MX3005(™) (Stratagene; La Jolla, Calif.), and Cepheid SMARTCYCLER™ can by used to amplify nucleic acid sequences in real-time.

The amplified influenza nucleic acid, for example an influenza type or subtype specific nucleic acid, can be detected in real-time, for example by real-time PCR such as real-time RT-PCR, in order to determine the presence, the identity, and/or the amount of an influenza type or subtype specific nucleic acid in a sample. In this manner, an amplified nucleic acid sequence, such as an amplified influenza nucleic acid sequence, can be detected using a probe specific for the product amplified from the influenza sequence of interest, such as an influenza sequence that is specific for influenza type A, type B, subtype H1, H3, H5, North America H7, European H7, and Asian H9. Detecting the amplified product includes the use of labeled probes that are sufficiently complementary and hybridize to the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest includes the combined use of PCR amplification and a labeled probe such that the product is measured using real-time RT-PCR. In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes disclosed herein that are an arrayed in a predetermined array with an addressable location and that are complementary to the amplified target nucleic acid.

In one embodiment, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the DNA sequence of interest and in this way, using Influenza type and/or subtype specific probes, can detect the presence, identity, and/or amount of an influenza type and/or subtype in a sample. In one embodiment, the fluorescently-labeled DNA probes used to identify amplification products have spectrally distinct emission wavelengths, thus allowing them to be distinguished within the same reaction tube.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid.

Influenza Profiling Arrays

An array containing a plurality of heterogeneous probes for the detection, typing, and/or subtyping of influenza viruses are disclosed. Such arrays may be used to rapidly detect and/or identify the type and/or subtype of an influenza virus in a sample. For example the arrays can be used to determine the presence of influenza A or influenza B in a sample and to determine if the influenza virus is of subtype H1, H3, H5, H7 (North American or European), or Asian H9.

Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, an influenza profiling array is a collection of separate probes at the array addresses. The influenza profiling array is then contacted with a sample suspected of containing influenza nucleic acids under conditions allowing hybridization between the probe and nucleic acids in the sample to occur. Any sample potentially containing, or even suspected of containing, influenza nucleic acids may be used, including nucleic acid extracts, such as amplified or non-amplified DNA or RNA preparations. A hybridization signal from an individual address on the array indicates that the probe hybridizes to a nucleotide within the sample. This system permits the simultaneous analysis of a sample by plural probes and yields information identifying the influenza nucleic acids contained within the sample. In alternative embodiments, the array contains influenza nucleic acids and the array is contacted with a sample containing a probe. In any such embodiment, either the probe or the influenza nucleic acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

Influenza profiling arrays may vary in structure, composition, and intended functionality, and may be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+96-well plate, or the 384 Microlite+384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses may be found on smaller arrays). Such a correlation is not necessary, however.

The arrays herein may be described by their densities (the number of addresses in a certain specified surface area). For macroarrays, array density may be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

Kits

The nucleic acid primers and probes disclosed herein can be supplied in the form of a kit for use in the detection, typing, and/or subtyping of influenza, including kits for any of the arrays described above. In such a kit, an appropriate amount of one or more of the nucleic acid probes and or primers is provided in one or more containers or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection, typing, and subtyping of influenza nucleotide sequences.

In some applications, one or more primers (as described above), such as pairs of primers, may be provided in pre-measured single use amounts in individual, typically disposable, tubes or equivalent containers. With such an arrangement, the sample to be tested for the presence of influenza nucleic acids can be added to the individual tubes and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al, Sambrook et al, and Ausubel et al A kit may include more than two primers in order to facilitate the PCR amplification of a larger number of influenza nucleotide sequences.

In some embodiments, kits also may include the reagents necessary to carry out PCR amplification reactions, including DNA sample preparation reagents, appropriate buffers (such as polymerase buffer), salts (for example, magnesium chloride), and deoxyribonucleotides (dNTPs).

One or more control sequences for use in the PCR reactions also may be supplied in the kit (for example, for the detection of human RNAse P).

Particular embodiments include a kit for detecting and typing and/or subtyping an influenza nucleic acid based on the arrays described above. Such a kit includes at least one probe specific for an influenza nucleic acid (as described above) and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In other particular embodiments, the kit includes equipment, reagents, and instructions for extracting and/or purifying nucleotides from a sample.

Synthesis of Oligonucleotide Primers and Probes

In vitro methods for the synthesis of oligonucleotides are well known to those of ordinary skill in the art; such methods can be used to produce primers and probes for the disclosed methods. The most common method for in vitro oligonucleotide synthesis is the phosphoramidite method, formulated by Letsinger and further developed by Caruthers (Caruthers et al., *Chemical synthesis of deoxyoligonucleotides*, in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach*, IRL Press, 1984.

In general, the synthesis reactions proceed as follows: A dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleotide to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for example, U.S. Pat. Nos. 4,415,732, 4,458,066, 4,500,707, 4,973,679, and 5,132,418. Oligonucleotide synthesizers that employ this or similar methods are available commercially (for example, the PolyPlex oligonucleotide synthesizer from Gene Machines, San Carlos, Calif.). In addition, many companies will perform such synthesis (for example, Sigma-Genosys, The Woodlands, Tex.; Qiagen Operon, Alameda, Calif.; Integrated DNA Technologies, Coralville, Iowa; and TriLink Bio-Technologies, San Diego, Calif.).

The following examples are provided to illustrate particular features of certain embodiments. However, the particular features described below should not be construed as limitations on the scope of the invention, but rather as examples from which equivalents will be recognized by those of ordinary skill in the art.

EXAMPLES

Example 1

Sample Collection and Preparation

This example describes exemplary procedures for the collection and preparation of samples for the determination of the presence of influenza nucleic acids.

Samples obtained from the respiratory tract were collected either as broncheoalveolar lavage, tracheal aspirates, sputum, nasopharyngeal or oropharyngeal aspirates or washes, or nasopharyngeal or oropharyngeal swabs. Swabs were collected using swabs with a DACRON® tip and an aluminum or plastic shaft. For specific viral isolates, viruses were propagated in either MDCK cells or embryonated chicken eggs. For validation of the primers and probes disclosed herein the following viral isolates were used: X31 (H3N2)(Aichi/2/68× PR8 reassortant), A/Panama/2007/99 (H3N2), A/New Caledonia/20/99 (H1N1), A/Vietnam/1203/2003 (H5N1), A/HongKong/1203/99 (H9N2), A/Netherlands/219/2003 (H7N7), A/New York/5295/2003 (H7N2) and B/Hong Kong/330/2001. Samples were refrigerated or frozen prior to nucleic acid extraction. Viral RNA was extracted from the samples using the QIAAMP® Viral RNAEASY™ Mini Kit available from QIAGEN® (Valencia, Calif.) according to the manufacturer's recommendations.

Example 2

Selection of Probe/Primer Sets

This example describes the rational and procedures used to design probes and primers for the detection, typing and subtyping of influenza virus.

Oligonucleotide primers and probes for universal detection of influenza type A and influenza type B influenza viruses were selected from highly conserved (consensus) regions of the M and NS genes, respectively, based on nucleotide alignments of all available sequence data from GENBANK® database of National Centers for Biological Information, NIH (NCBI) and the Influenza Sequence Database of Los Alamos National Laboratories (LANL). Similarly, primers and probes specific for the hemagglutinin (HA) gene of modern human H1, H3, Asian avian H5, North American avian H7, European avian H7 and Asian avian H9 viruses were designed. Because of the pandemic potential of influenza subtype Asian avian H5, two redundant primer and probe set were designed to detect this influenza subtype. The consensus sequence for the region of the influenza type A M gene used for the design of probes and primers specific for influenza type A is given in the table shown in FIG. 9. The consensus sequence for the region of the influenza type B NS gene used for the design of probes and primers specific for influenza type B is given in the table shown in FIG. 10. The consensus sequences for the region of the influenza subtype H1 HA gene used for the design of probes and primers specific for influenza subtype H1 is given in the table shown in FIG. 11. The consensus sequences for the region of the influenza subtype H3 HA gene used for the design of probes and primers specific for influenza subtype H3 is given in the table shown in FIG. 12. The consensus sequence for a region of the influenza subtype H5 HA gene used for the design of probes and primers specific for influenza t subtype H5 is given in the table shown in FIG. 13. The consensus sequence for a region of the influenza subtype H5 HA gene used for the design of probes and primers specific for influenza subtype H5 is given in the table shown in FIG. 14. The consensus sequence for the region of the influenza subtype North American H7 HA gene used for the design of probes and primers specific for influenza subtype North American H7 is given in the table shown in FIG. 15. The consensus sequence for the region of the influenza subtype European H7 HA gene used for the design of probes and primers specific for influenza subtype European H7 is given in the table shown in FIG. 16. The consensus sequence for the region of the influenza subtype Asian H9 HA gene used for the design of probes and primers specific for influenza subtype Asian H9 is given in the table shown in FIG. 17. With reference to FIGS. 9-17 the consensus sequence for the influenza viral type or subtype specific nucleic acid is shown at the top of each table. The boxed sequences represent the positions of exemplary probes and primers disclosed herein. Nucleotide variations for the indicated influenza viral isolates are shown in the columns below the consensus sequence, with a dot meaning that the nucleotide present at that position is identical to the consensus sequence. In addition K=G or T; S=G or C; R=A or G; M=A or C; and Y=T or C.

In order to avoid loss of reaction performance due to primer-dimer or hairpin loop formation, primers and probes were evaluated using Software packages PRIMEREXPRESS® (Applied Biosystems) and BEACON DESIGNER 4.0® (PREMIER Biosoft International) to predict secondary structures and self-annealing probabilities.

Each primer and probe sequence was subjected to a nucleotide Blast search (NCBI) against the entire GENBANK® nucleotide database to validate their specificities and avoid non-specific reactivity. The probe and primers listed in Table 1 were selected for validation using TAQMAN® chemistry. Primers and dual-labeled TAQMAN® probes (Table 1) were synthesized by the Biotechnology Core Facility, Centers for Disease Control.

TABLE 1

Probe and Primer Sets

| | Sequence | SEQ ID NO |
|---|---|---|
| Flu A | | |
| Flu A Forward Primer | GAC CRA TCC TGT CAC CTC TGA C | 3 |
| Flu A Consensus Reverse Primer | AGG $X_1$CA TTY TGG ACA AAK CGT CTA $X_2X_3$ | 4 |
| Flu A Reverse Primer No. 1 | AGG GCA TTY TGG ACA AAK CGT CTA | 5 |
| Flu A Reverse Primer No. 2 | AGG CAT TYT GGA CAA AKC GTC TAC G | 6 |
| Flu A Reverse Primer No. 3 | GGG CAT TYT GGA CAA AKC GTC TAC G | 7 |
| Flu A Probe[1] | TGC AGT CCT CGC TCA CTG GGC ACG | 8 |
| H1 | | |
| H1 Forward Primer | AAC TAC TAC TGG ACT CTR CTK GAA | 9 |
| H1 Reverse Primer | CCA TTG GTG CAT TTG AGK TGA TG | 10 |
| H1 Probe[2] | TGA YCC AAA GCC "T"CT ACT CAG TGC GAA AGC | 11 |
| H3 | | |
| H3 Forward Primer | AAG CAT TCC YAA TGA CAA ACC | 12 |
| H3 Reverse Primer | ATT GCR CCR AAT ATG CCT CTA GT | 13 |
| H3 Consensus Probe[1] | CAG SAT CAC ATA TGG GSC CTG TCC CAG | 14 |
| H3 Probe No. 1[1] | CAG GAT CAC ATA TGG GSC CTG TCC CAG | 15 |
| H3 Probe No. 2[1] | CAG CAT CAC ATA TGG GSC CTG TCC CAG | 16 |
| H5 primer and probe set a | | |
| H5 a Consensus Forward Primer | TGG AAA GTR TAA RAA ACG GAA CGT | 17 |
| H5 a Consensus Reverse Primer | YGC TAG GGA RCT CGC CAC TG | 18 |
| H5 a Consensus Probe[2] | YRA CTA YCC GCA G"T"A TTC AGA AGA AGC AAG AYT AA | 19 |
| H5 a Probe1[2] | TGA CTA CCC GCA G"T"A TTC AGA AGA AGC AAG ACT AA | 20 |

TABLE 1-continued Probe and Primer Sets

| | Sequence | SEQ ID NO |
|---|---|---|
| H5 a Probe2[2] | CAA CTA TCC GCA G"T"A TTC AGA AGA AGC AAG ATT AA | 21 |
| H5 primer and probe set b | | |
| H5 b Consensus Forward Primer | GGA ATG YCC CAA ATA YGT GAA RTC AA | 22 |
| H5 b Consensus Reverse Primer | CTC CCC TGC TCR TTG CTA TGG T | 23 |
| H5 b Consensus Probe[2] | TAY CCA TAC CAA CCA "T"CT ACC ATT CCC TGC CAT | 24 |
| H5 b Probe No. 1[2] | TAC CCA TAC CAA CCA "T"CT ACC ATT CCC TGC CAT | 25 |
| Flu B | | |
| Flu B Consensus Forward Primer | TCC TCA AYT CAC TCT TCG AGC G | 26 |
| Flu B Forward Primer No. 1 | TCC TCA ACT CAC TCT TCG AGC G | 27 |
| Flu B Reverse Primer | CGG TGC TCT TGA CCA AAT TGG | 28 |
| Flu B Probe[1] | CCA ATT CGA GCA GCT GAA ACT GCG GTG | 29 |
| H7 | | |
| North America H7 Forward Primer | AAA TGC ACA AGG AGA GGG AAC TG | 30 |
| North America H7 Reverse Primer | CAT TGC YAC YAA SAG YTC AGC RT | 31 |
| North America H7 Probe[2] | AAA GCA CCC ART C"T"G CAA TAG ATC AGA TCA CAG GC | 32 |
| European H7 Forward Primer | GCT TCA GGC ATC AAA ATG CAC AAG G | 33 |
| European H7 Reverse Primer | CAT TGC TAC YAA GAG TTC AGC RT | 34 |
| European H7 Probe[2] | ACC ACA CTT CTG TCA "T"GG AAT CTC TGG TCC A | 35 |
| H9 | | |
| Asian H9 Forward Primer | CAA GCT GGA ATC TGA RGG AAC TTA CA | 36 |
| Asian H9 Reverse Primer | GCA TCT GCA AGA TCC ATT GGA CAT | 37 |
| Asian H9 Probe[1] | CCC AGA ACA RGA AGG CAG CAA ACC CCA TTG | 38 |
| RNP | | |
| RNP Forward Primer | AGA TTT GGA CCT GCG AGC G | 39 |
| RNP Reverse Primer | GAG CGG CTG TCT CCA CAA GT | 40 |
| RNP Probe[1] | TTC TGA CCT GAA GGC TCT GCG CG | 41 |

Where K = G or T; S = G or C; R = A or G; Y = T or C; $X_1$ = G or no nucleotide; $X_2$ = C or no nucleotide; and $X_3$ = G or no nucleotide.
[1]TAQMAN ® probes were labeled at the 5'-end with the reporter molecule 6-carboxyfluorescein (FAM) and with the quencher, BLACKHOLE QUENCHER ™ 1 (BHQ ™1) (Biosearch Technologies, Inc., Novato, CA) at the 3'-end.
[2]TAQMAN ® probes were labeled at the 5'-end with the reporter molecule 6-carboxyfluorescein (FAM) and quenched internally at a modified "T" residue with QSY ® 7 (Molecular Probes, Inc.) or BHQ ™. Internally quenched probes also were modified at the 3'-end to prevent extension of the probe by Taq polymerase.

The reaction efficiency of the primer sets was individually tested in a set of five-fold serial dilutions of viral RNA using SYBER green binding to double stranded nucleic acids as an indicator of amplification. All rt RT-PCR assays for detection and characterization of influenza were designed to achieve reaction efficiencies of approximately 100%. A reaction efficiency of 100% indicates that a primer set is capable of achieving a complete doubling of the nucleic acid target sequence in a single round of amplification.

Figure 5A:
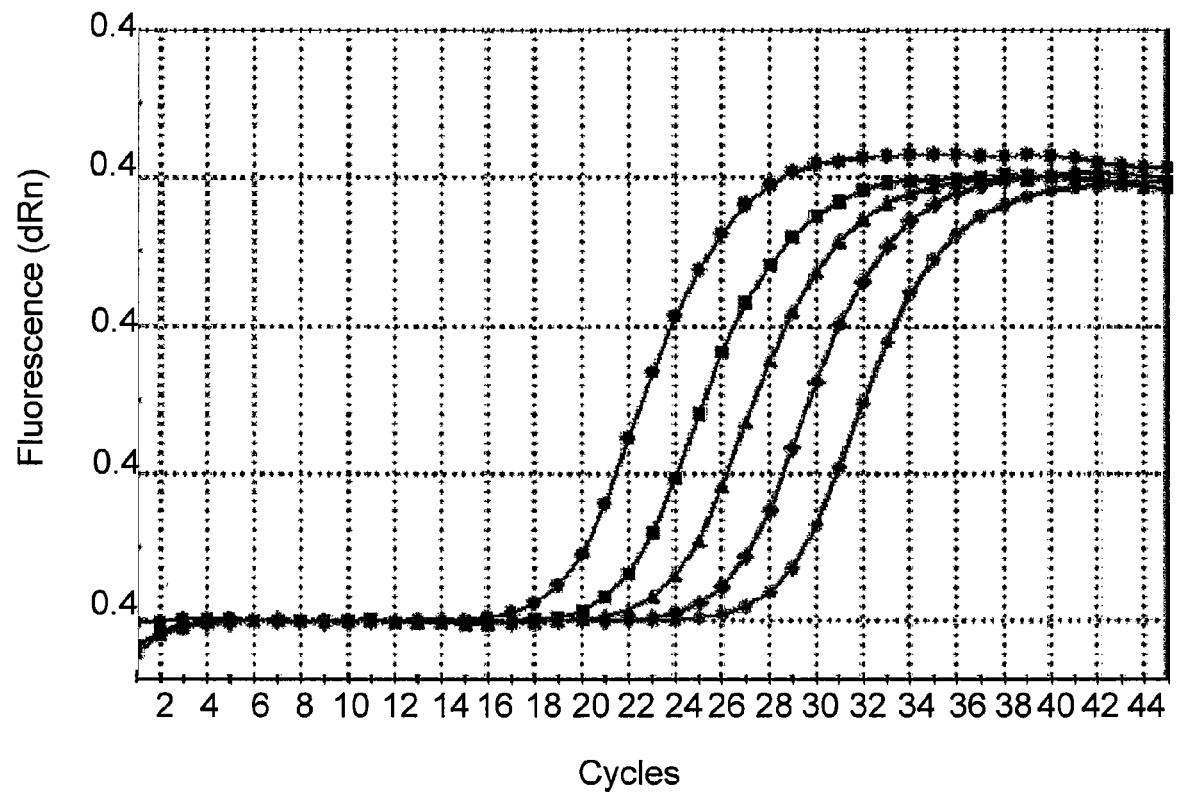
FIG. 5A is a graph of a dilution series of SYBER green binding to influenza nucleic acids amplified with influenza A specific primers.
Figure 5B:
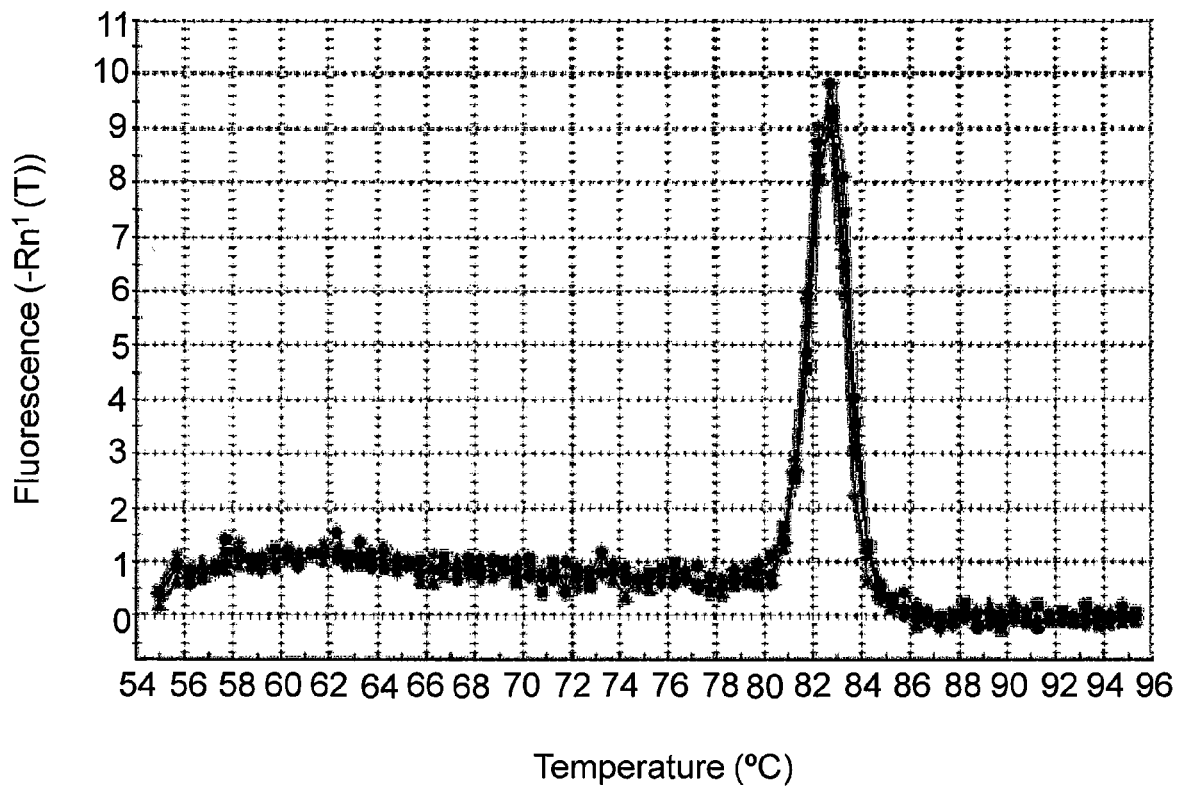
FIG. 5B is a graph of the dissociation curves obtained from the meting of influenza nucleic acids amplified with influenza A specific primers as shown in FIG. 5A.

With reference to FIG. 5A-5C, the reaction efficiency of the primer set for universal detection of influenza type A was determined by testing against a five-fold serial dilution of viral RNA. Identical tests were carried out with the primer sets specific for each viral type and subtype. FIG. 5A shows the relative fluorescence of SYBER green when bound to double stranded nucleic acid versus the number of PCR cycles. The individual rt RT-PCR reactions were subjected to melting curve analysis to confirm that the SYBER green fluorescence was attributable to specific amplification of the influenza A gene target. As shown in FIG. 5B, all reactions showed double stranded nucleic acid melting at the same temperature, indicating specific amplification. Similar melting curve analysis was performed for all primer sets and demonstrated that the primers were specific for their specific target influenza nucleic acid sequence. As shown on FIG. 5C, reaction Ct values for the influenza A specific primers were plotted against their relative RNA concentration and the doubling efficiency (% reaction efficiency) was determined by estimating the slope using regression analysis. A slope of 3.23 indicates a reaction efficiency of approximately 100%. A reaction efficiency of 100.3% percent was obtained for the influenza type A specific primers. All primer sets tested had a reaction efficiency of approximately 100% when subjected to the same analysis.

Following the validation of the reaction specificity and efficiency of the primer sets the reaction efficiency of the primer/probe sets was validated. Using a five-fold viral dilutions series the reaction efficiency of the individual influenza type and subtype primer/probe sets was analyzed. Exemplary data for the analysis of the probe/primer set specific for influenza type A is shown in FIG. 6A and FIG. 6B.

Figure 6A:
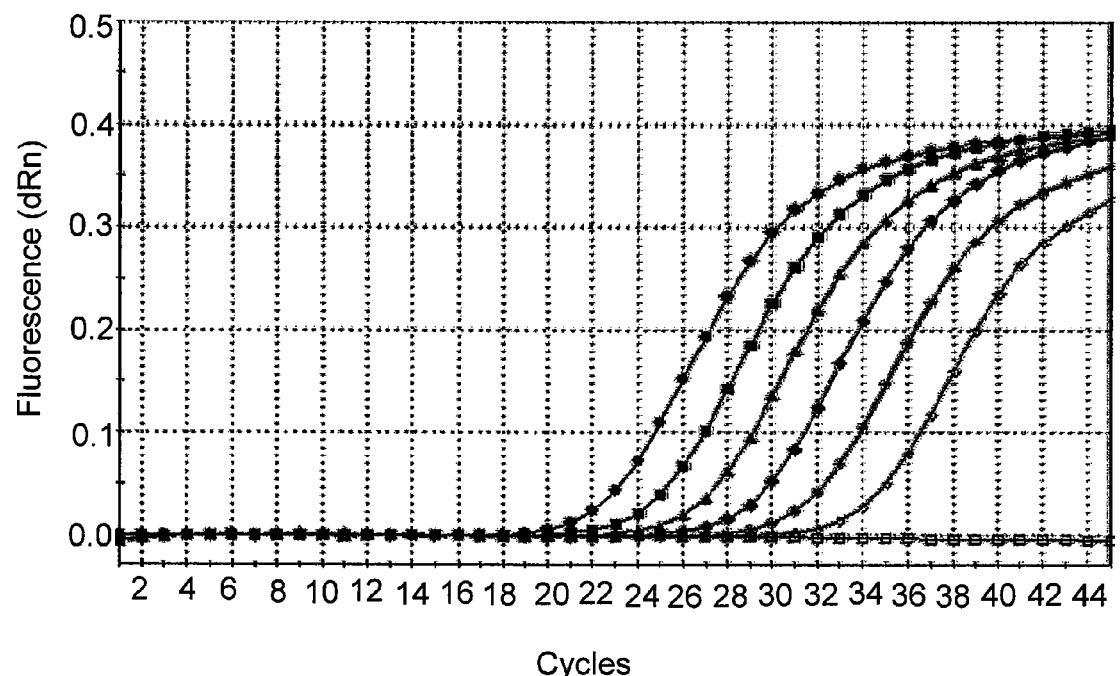
FIG. 6A is a graph of data obtained from rt RT-PCRs run on a dilution series of influenza nucleic acids using an influenza A specific probe/primer set.
Figure 6B:
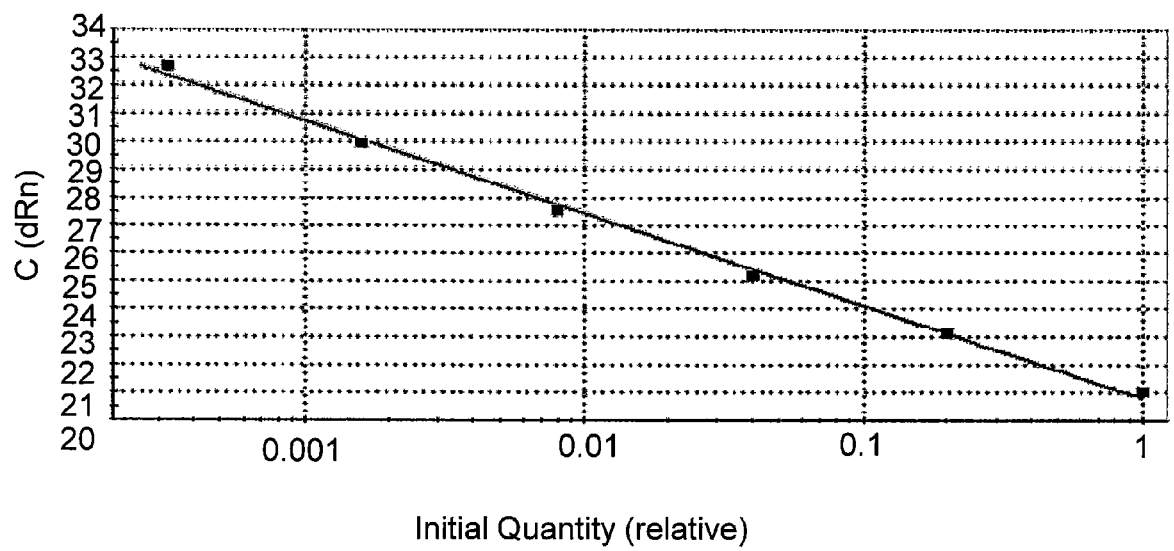
FIG. 6B is a plot of the Ct values obtained from the graphs shown in FIG. 6A, as a function of template nucleic acid concentration.

As shown in FIG. 6A, the reaction efficiency of the primer/probe set for universal detection of type A influenza was determined by testing against a five-fold serial dilution of viral RNA. The reaction Ct values were plotted against their relative RNA concentration to estimate the reaction efficiency using regression analysis (FIG. 6B). Similar test were carried out on all available primer sets. As shown in Table 2, all of the primer/probe sets exhibited reaction efficiencies at or near 100%.

TABLE 2 rt RT-PCT reaction efficiencies.

| | Efficiency | R Squared |
|---|---|---|
| Influenza Typing sets | | |
| Flu A | 100.3% | 1.000 |
| Flu B | 100.7% | 1.000 |
| Influenza Subtyping sets | | |
| Human H1 HA | 100.1% | 0.996 |
| Human H3 HA | 99.8% | 0.998 |
| Eurasian H5 HA (a) | 102.8% | 0.998 |
| Eurasian H5 HA (b) | 100.3% | 0.996 |
| North American Avian H7 HA | 94.2% | 1.000 |
| Eurasian H7 HA | 98.9% | 0.994 |
| Asian Avian H9 HA | 96.4% | 0.995 |

Figure 7:
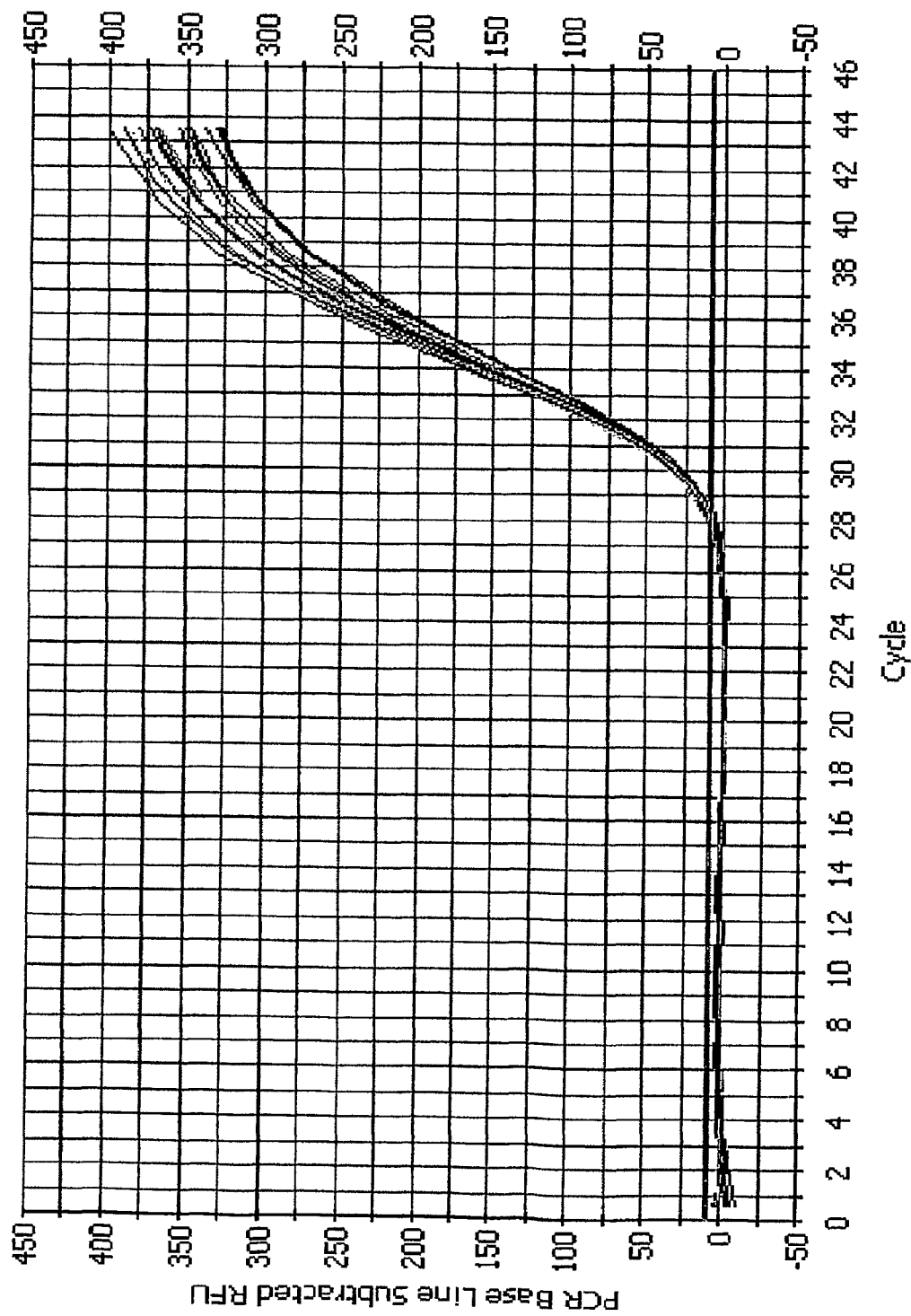
FIG. 7 is a graph of the data obtained from a series of rt RT-PCRs run at annealing temperatures ranging from 50-62.5° C.

One of the design criteria for the disclosed primer and probe sets was that they could be used at a variety of annealing (hybridization) temperatures. Thus, the probe/primer sets were tested for their ability to perform at a range of annealing temperatures from 50-62.5° C. FIG. 7 shows a plot of the real-time RT-PCR reactivity comparison of the influenza A primer/probe set with annealing temperatures ranging from 50-62.5° C. In order to determine the optimal thermocycling conditions, each probe/primer set was similarly tested with annealing temperatures ranging from 50-62.5° C. All primer/probe sets were designed to demonstrate comparable reactivity at annealing temperatures ranging from 50-60° C. and exhibited stable Ct values at all temperatures tested (Table 3 and Table 4).

TABLE 3

Thermal gradient analysis of TAQMAN ® primer/probe sets from 50-62.5 C.

| Tm | Flu A Ct | ΔCt | Flu B Ct | ΔCt | H1 Ct | ΔCt | H3 Ct | ΔCt | AsH5a Ct | ΔCt |
|---|---|---|---|---|---|---|---|---|---|---|
| 50 | 21.6 | 0.2 | 21.6 | −0.1 | 27.1 | 0.1 | 25.6 | 0.0 | 19.3 | −0.1 |
| 50 | 21.4 | 0 | 21.9 | 0.2 | 27.6 | 0.6 | 25.6 | 0.0 | 19.3 | −0.1 |
| 51 | 21.3 | −0.1 | 21.8 | 0.1 | 26.6 | −0.4 | 25.6 | 0.0 | 19.3 | −0.1 |
| 51 | 21.4 | 0 | 21.3 | −0.4 | 27.1 | 0.1 | 25.6 | 0.0 | 19.2 | −0.2 |
| 52.5 | 21.2 | −0.2 | 21.7 | 0.0 | 26.4 | −0.6 | 25.5 | −0.1 | 19.3 | −0.1 |
| 52.5 | 21.5 | 0.1 | 21.5 | −0.2 | 27.1 | 0.1 | 25.5 | −0.1 | 19.2 | −0.2 |
| 54.8 | 21.2 | −0.2 | 21.8 | 0.1 | 27 | 0.0 | 25.6 | 0.0 | 19.2 | −0.2 |
| 54.8 | 21.3 | −0.1 | 21.5 | −0.2 | 26.9 | −0.1 | 25.5 | −0.1 | 19.3 | −0.1 |
| 58 | 21.4 | 0 | 21.9 | 0.2 | 27 | 0.0 | 25.7 | 0.1 | 19.6 | 0.2 |
| 58 | 21.5 | 0.1 | 21.4 | −0.3 | 26.9 | −0.1 | 25.6 | 0.0 | 19.4 | 0.0 |
| 60.3 | 21.4 | 0 | 22.2 | 0.5 | 27.1 | 0.1 | 25.7 | 0.1 | 19.8 | 0.4 |
| 60.3 | 21.6 | 0.2 | 22 | 0.3 | 27.5 | 0.5 | 25.7 | 0.1 | 19.8 | 0.4 |
| 61.7 | 21.4 | 0 | 22.5 | 0.8 | 27.4 | 0.4 | 26.3 | 0.7 | 20.3 | 0.9 |
| 61.7 | 21.7 | 0.3 | 21.9 | 0.2 | 27.9 | 0.9 | 26.2 | 0.6 | 20.3 | 0.9 |
| 62.5 | 21.6 | 0.2 | 22.3 | 0.6 | 28.2 | 1.2 | 26.4 | 0.8 | 20.4 | 1.0 |
| 62.5 | 21.5 | 0.1 | 22.6 | 0.9 | 27.4 | 0.4 | 26.7 | 1.1 | 20.6 | 1.2 |
| | Mean Ct 21.4 | | Mean Ct 21.7 | | Mean Ct 27.0 | | Mean Ct 25.6 | | Mean Ct 19.4 | |

| Tm | NAmH7 Ct | ΔCt | EurH7 Ct | ΔCt | AsH9 Ct | ΔCt | AsH5b Ct | ΔCt |
|---|---|---|---|---|---|---|---|---|
| 50 | 27.3 | 0.3 | 25.7 | 0.1 | 27.4 | −0.1 | 20 | 0.6 |
| 50 | 27.4 | 0.4 | 26.2 | 0.6 | 27.6 | 0.1 | 20.2 | 0.8 |
| 51 | 27 | 0.0 | 25.5 | −0.1 | 27.7 | 0.2 | 19.7 | 0.3 |
| 51 | 26.9 | −0.1 | 25.9 | 0.3 | 27.5 | 0.0 | 19.8 | 0.4 |
| 52.5 | 26.8 | −0.2 | 25.4 | −0.2 | 27.6 | 0.1 | 19.6 | 0.2 |
| 52.5 | 26.9 | −0.1 | 25.7 | 0.1 | 27.6 | 0.1 | 19.4 | 0.0 |
| 54.8 | 26.5 | −0.5 | 25.2 | −0.4 | 27.6 | 0.1 | 19.1 | −0.3 |
| 54.8 | 26.9 | −0.1 | 25.4 | −0.2 | 27.3 | −0.2 | 19.2 | −0.2 |
| 58 | 26.8 | −0.2 | 25.8 | 0.2 | 27.6 | 0.1 | 18.9 | −0.5 |
| 58 | 27.3 | 0.3 | 25.1 | −0.5 | 27.3 | −0.2 | 19 | −0.4 |
| 60.3 | 27 | 0.0 | 26.1 | 0.5 | 27.2 | −0.3 | 18.8 | −0.6 |
| 60.3 | 27.4 | 0.4 | 24.7 | −0.9 | 27.4 | −0.1 | 18.9 | −0.5 |
| 61.7 | 27.6 | 0.6 | 26.4 | 0.8 | 27.2 | −0.3 | 19 | −0.4 |
| 61.7 | 27.6 | 0.6 | 24.5 | −1.1 | 27.1 | −0.4 | 18.9 | −0.5 |
| 62.5 | 27.7 | 0.7 | 25.6 | 0.0 | 27.1 | −0.4 | 18.7 | −0.7 |
| 62.5 | 27.4 | 0.4 | 24.2 | −1.4 | 27.3 | −0.2 | 19 | −0.4 |
| | Mean Ct 27.0 | | Mean Ct 25.6 | | Mean Ct 27.5 | | Mean Ct 19.4 | |

Mean Ct = mean of Ct value from reactions with Tm 50-60.0 C.; ΔCt = Ct value − Mean Ct

TABLE 4

Thermal gradient analysis of TAQMAN ® primer/probe combined statistics.

| Tm | Flu A AvΔCt | Flu B AvΔCt | H1 AvΔCt | H3 AvΔCt | AsH5a AvΔCt | NAmH7 AvΔCt | EurH7 AvΔCt | AsH9 AvΔCt | AsH5b AvΔCt |
|---|---|---|---|---|---|---|---|---|---|
| 50   | 0.10  | 0.03  | 0.32  | 0.00  | −0.14 | 0.33  | 0.39  | 0.02  | 0.72  |
| 51   | −0.05 | −0.07 | −0.18 | 0.00  | −0.14 | −0.07 | 0.14  | 0.12  | 0.37  |
| 52.5 | −0.05 | −0.12 | −0.28 | −0.10 | −0.14 | −0.17 | −0.01 | 0.12  | 0.12  |
| 54.8 | −0.15 | −0.07 | −0.08 | −0.05 | −0.14 | −0.32 | −0.26 | −0.03 | −0.23 |
| 58   | 0.05  | −0.07 | −0.08 | 0.05  | 0.11  | 0.03  | −0.11 | −0.03 | −0.43 |
| 60.3 | 0.10  | 0.38  | 0.27  | 0.10  | 0.41  | 0.18  | −0.16 | −0.18 | −0.53 |
| 61.7 | 0.15  | 0.48  | 0.62  | 0.65  | 0.91  | 0.58  | −0.11 | −0.33 | −0.43 |
| 62.5 | 0.15  | 0.73  | 0.77  | 0.95  | 1.11  | 0.53  | −0.66 | −0.28 | −0.53 |

Example 3

Real-time Reverse Transcriptase (rt RT-PCR) of Samples

This example describes the procedures used for the determination of the presence of influenza types and subtypes in a sample using rt RT-PCR in a multiwell format. Hydrolysis probe (TAQMAN®) rt RT-PCR reactions were performed using QUANTITECT™ Probe One-step RT-PCR (QIAGEN®) and TAQMAN# One-Step RT-PCR Master Mix (ABI) kits according to manufacturer's recommended procedures. Primer and probe reaction concentrations were 0.8 μM and 0.2 μM, respectively.

Individual 1.5 ml microcentrifuge tubes were prepared for each individual primer/probe set used. Individual primers and probes were vortexed and briefly centrifuged prior to dispensing. Into each microcentrifuge tube was added 20 microliter rt RT-PCR master mix, wherein the master mix was optimized for various real time PCR instruments. The mister mix was prepared as shown in Table 5.

TABLE 5

| Master Mix. | | | |
|---|---|---|---|
| | ABI | Qiagen | Invitrogen/ Biorad |
| 2X PCR Master Mix | N × 12.5 μl | N × 12.5 μl | N × 12.5 μl |
| RT Mix | N × 0.625 μl | N × 0.25 μl | N × 0.5 μl |
| Forward primer (0.8 μM final concentration) | N × 0.5 μl | N × 0.5 μl | N × 0.5 μl |
| Reverse primer (0.8 μM final concentration) | N × 0.5 μl | N × 0.5 μl | N × 0.5 μl |
| Probe (0.2 μM final concentration) | N × 0.5 μl | N × 0.5 μl | N × 0.5 μl |
| Nuclease free water | N × 5.375 μl | N × 5.75 μl | N × 5.5 μl |
| Total volume | N × 20.0 μl | N × 20.0 μl | N × 20.0 μl |

Where N is the number of samples including non template controls (NTC). For viral template controls (VTC) and positive controls for human RNAse P individual mastermixes were prepared. The reactions were mixed by pipeting up and down, without vortexing. Twenty microliters of each master mix was added into individual wells of a 96 well plate. An example of the arrayed format used is shown in Table 6 below:

TABLE 6

| Probe/Primer Setup for rt RT-PCR. | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | FluA | FluA | FluA | FluA | FluA | FluA | FluA | FluA | FluA | FluA | FluA | FluA |
| B | H1 | H1 | H1 | H1 | H1 | H1 | H1 | H1 | H1 | H1 | H1 | H1 |
| C | H3 | H3 | H3 | H3 | H3 | H3 | H3 | H3 | H3 | H3 | H3 | H3 |
| D | H5a | H5a | H5a | H5a | H5a | H5a | H5a | H5a | H5a | H5a | H5a | H5a |
| E | H5b | H5b | H5b | H5b | H5b | H5b | H5b | H5b | H5b | H5b | H5b | H5b |
| F | H9 | H9 | H9 | H9 | H9 | H9 | H9 | H9 | H9 | H9 | H9 | H9 |
| G | FluB | FluB | FluB | FluB | FluB | FluB | FluB | FluB | FluB | FluB | FluB | FluB |
| H | RNP | RNP | RNP | RNP | RNP | RNP | RNP | RNP | RNP | RNP | RNP | RNP |

FluA is a primer probe set specific for influenza A; H1 is a primer probe set specific for H1; H3 is a primer probe set specific for H3; H5a is a primer probe set specific for H5; H5b is a primer probe set specific for H5; H9 is a primer probe set specific for H9; FluB is a primer probe set specific for influenza B; and RNP is a primer probe set specific for human RNAse P.

RNA Samples of viral unknown as well as the NTC, VTC, and a mock extraction control were added to the individual wells. NTCs were added first to control for contamination in the master mix. For NTCs 5 microliters of distilled water was added. Five microliters of viral unknown was added to each well with the exception of control wells. For positive controls five microliters of viral RNA was added. The mock extraction controls were added after the samples have been added to control for cross-contamination during sample preparation or addition. VTCs were added last after all samples and NTCs were sealed to prevent contamination. An example of the array format used is shown in Table 7 below:

TABLE 7

Sample Setup.

|   | 1 | 2 | 3 | 4 | 5 | 6 | 7 | 8 | 9 | 10 | 11 | 12 |
|---|---|---|---|---|---|---|---|---|---|----|----|----|
| A | NTC | S1 | S2 | S3 | S4 | S5 | S6 | S7 | S8 | S9 | MOCK | VTC |
| B | NTC | S1 | S2 | S3 | S4 | S5 | S6 | S7 | S8 | S9 | MOCK | VTC |
| C | NTC | S1 | S2 | S3 | S4 | S5 | S6 | S7 | S8 | S9 | MOCK | VTC |
| D | NTC | S1 | S2 | S3 | S4 | S5 | S6 | S7 | S8 | S9 | MOCK | VTC |
| E | NTC | S1 | S2 | S3 | S4 | S5 | S6 | S7 | S8 | S9 | MOCK | VTC |
| F | NTC | S1 | S2 | S3 | S4 | S5 | S6 | S7 | S8 | S9 | MOCK | VTC |
| G | NTC | S1 | S2 | S3 | S4 | S5 | S6 | S7 | S8 | S9 | MOCK | VTC |
| H | NTC | S1 | S2 | S3 | S4 | S5 | S6 | S7 | S8 | S9 | MOCK | VTC |

Where NTC is the non-template control (no RNA). S1-S9 are samples obtained from a subject(s). MOCK is a mock extraction control and VTC is the viral template control.

Example 4

Real time RT-PCR of Samples

This example describes rt-RT-PCR parameters used for the determination of the presence, type and subtype of influenza in a sample.

Prior to an rt RT-PCR run, the 96 well plate was centrifuged at 500×g for 30 seconds at 4° C. The plate was loaded into a thermocycler and subjected to the PCR cycle as shown in Table 8. All reactions were performed on a Stratagene MX4000™, MX3000P™ or BioRad IQ ICYCLER™ platform. PCR conditions were optimized for each of the listed instruments. The reaction volume was 25 µl.

TABLE 8

Optimized PCR Conditions.

|  | ABI | Invitrogen/Biorad | Qiagen |
|---|---|---|---|
| Reverse Transcription | 50° C. for 30 min | 60° C. for 5 min<br>50° C. for 30 min | 60° C. for 5 min<br>50° C. for 30 min |
| Taq inhibitor inactivation | 95° C. for 10 min | 95° C. for 2 min | 95° C. for 15 min |
| PCR amplification (45 cycles) | 95° C. for 15 sec<br>55° C. for 30 sec*<br>72° C. for 30 sec | 95° C. for 15 sec<br>55° C. for 30 sec*<br>72° C. for 30 sec | 95° C. for 15 sec<br>55° C. for 30 sec*<br>72° C. for 30 sec |

*Fluorescence data was collected during the 55° C. incubation step. Primer/Probe sets performed comparably at annealing temperatures ranging from 50-60° C.

Example 5

The Determination of Influenza Viral Type and Subtype in Samples Obtained from Subjects This example describes the determination of the presence, type, and subtype of influenza viral nucleic acid in samples obtained from subjects.

Samples obtained from four subjects were tested for the presence of influenza using influenza specific probe and primer sets disclosed herein in rt RT-PCR TAQMAN® assays. In addition, the samples were tested for the presence of influenza viral types A and B and influenza subtypes H1, H2, and H5. The detection of human RNAse P was used as a control.

Figure 8A:
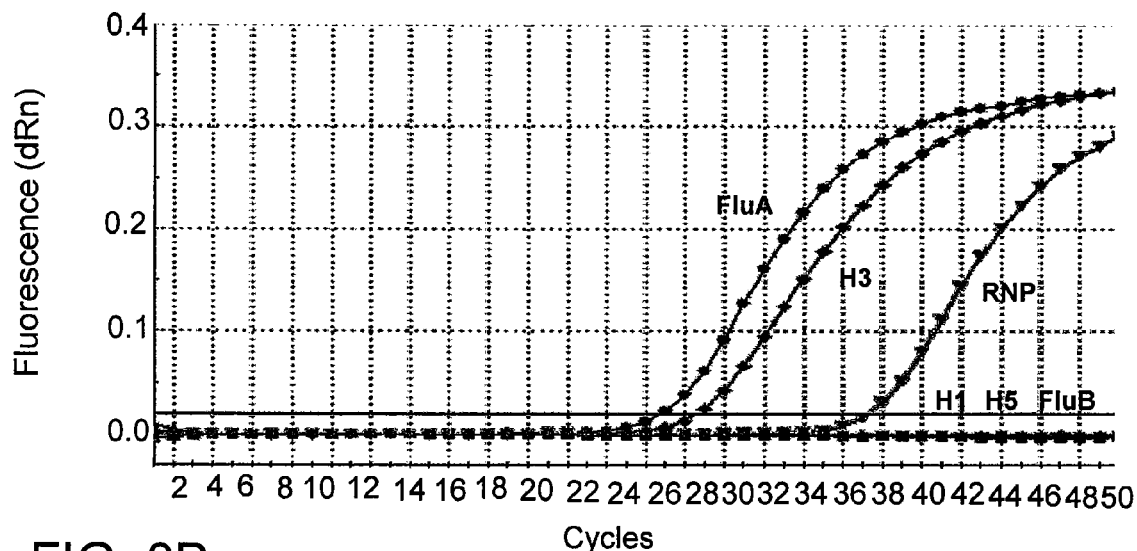
FIG. 8A is a graph of data generated from rt RT-PCRs of a sample obtained from a subject using the indicated influenza type and subtype TAQMAN® probes.
Figure 8B:
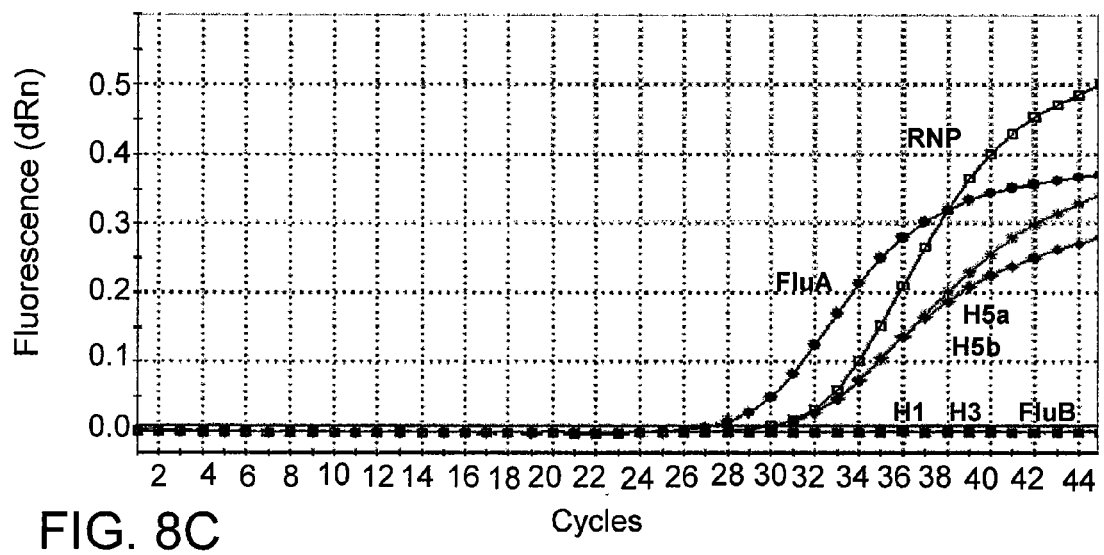
FIG. 8B is a graph of data obtained from rt RT-PCRs of a sample obtained from a subject using the indicated influenza type and subtype TAQMAN® probes.
Figure 8C:
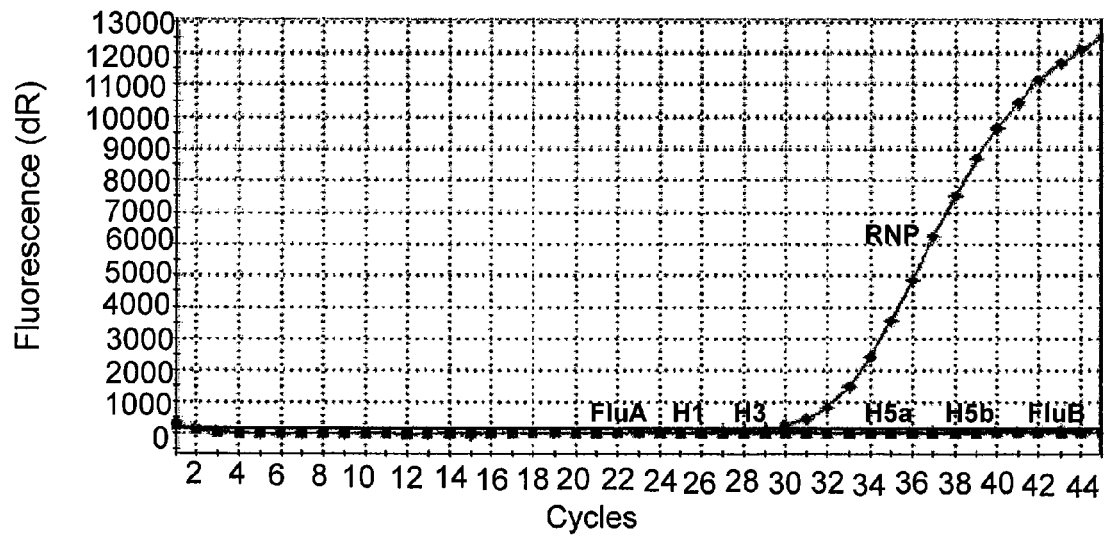
FIG. 8C is a graph of data generated from rt RT-PCRs of a sample obtained from a subject using the indicated influenza type and subtype TAQMAN® probes.
Figure 9A:
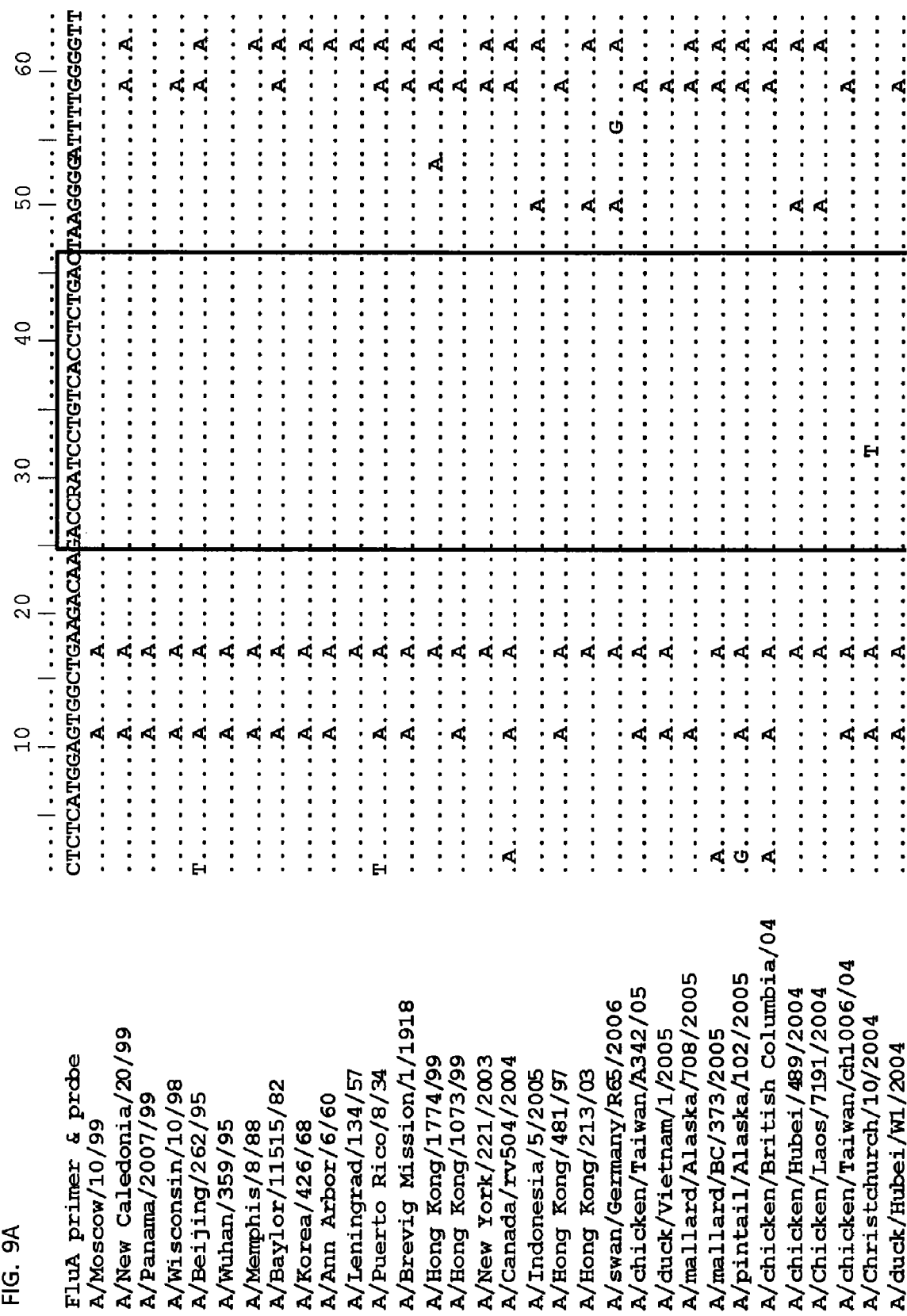
Figure 9D:
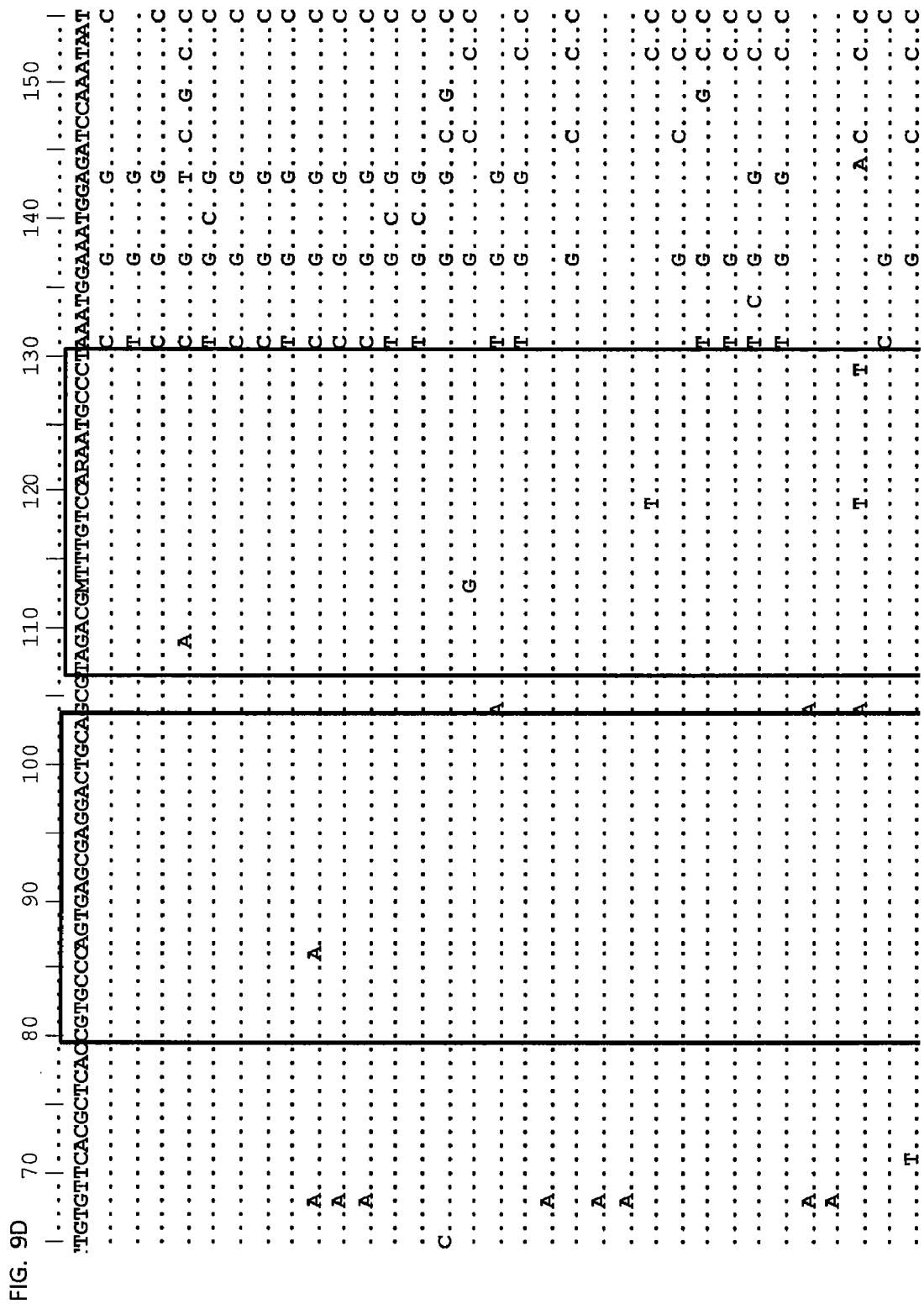
Figure 10A:
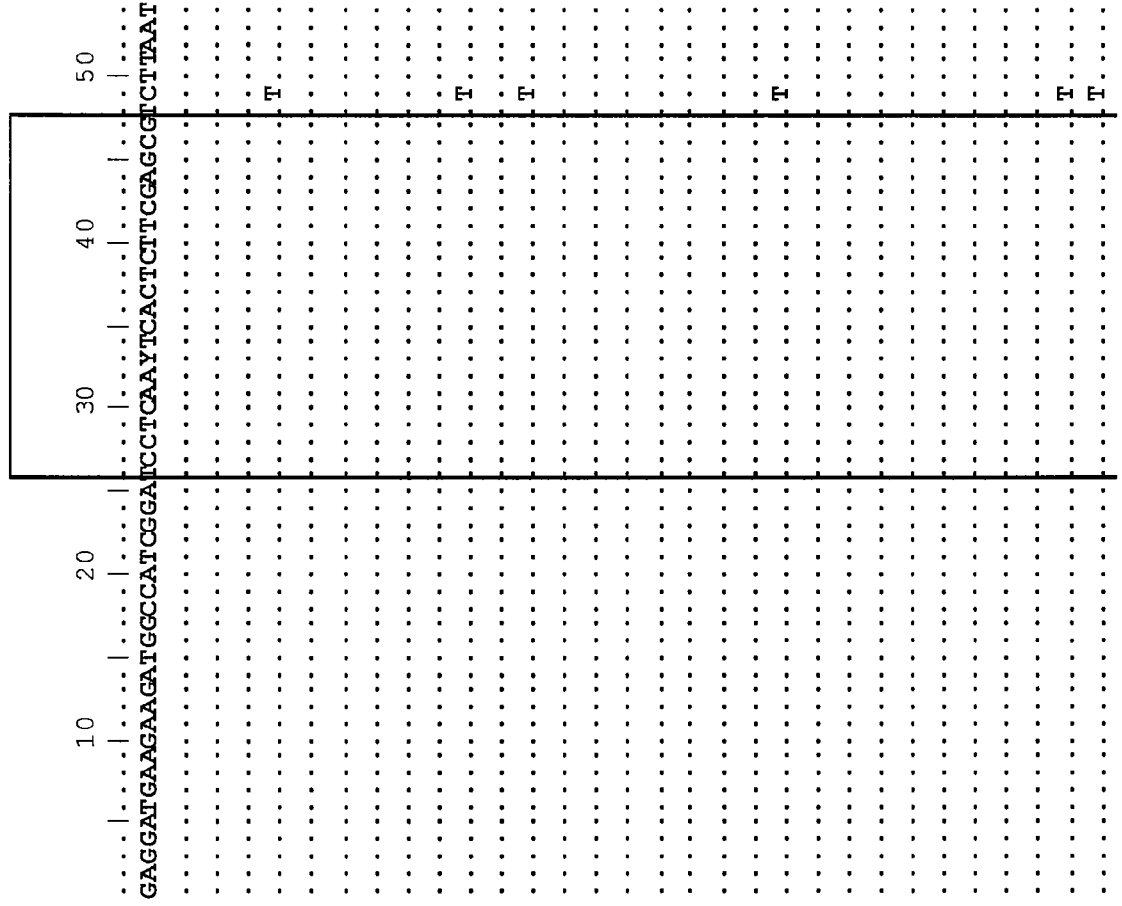
Figure 10C:
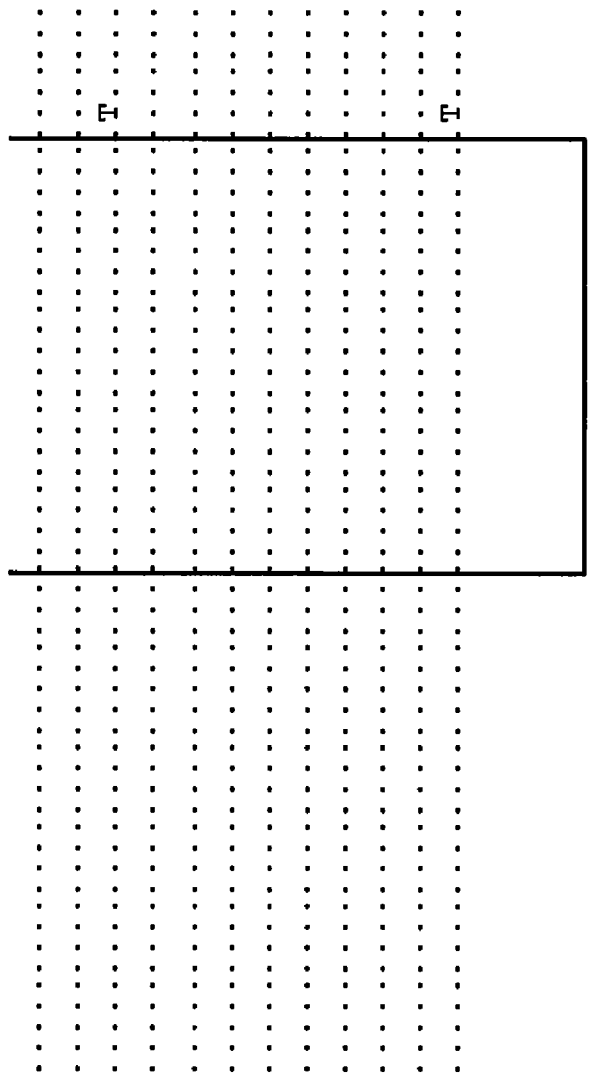
Figure 10E:
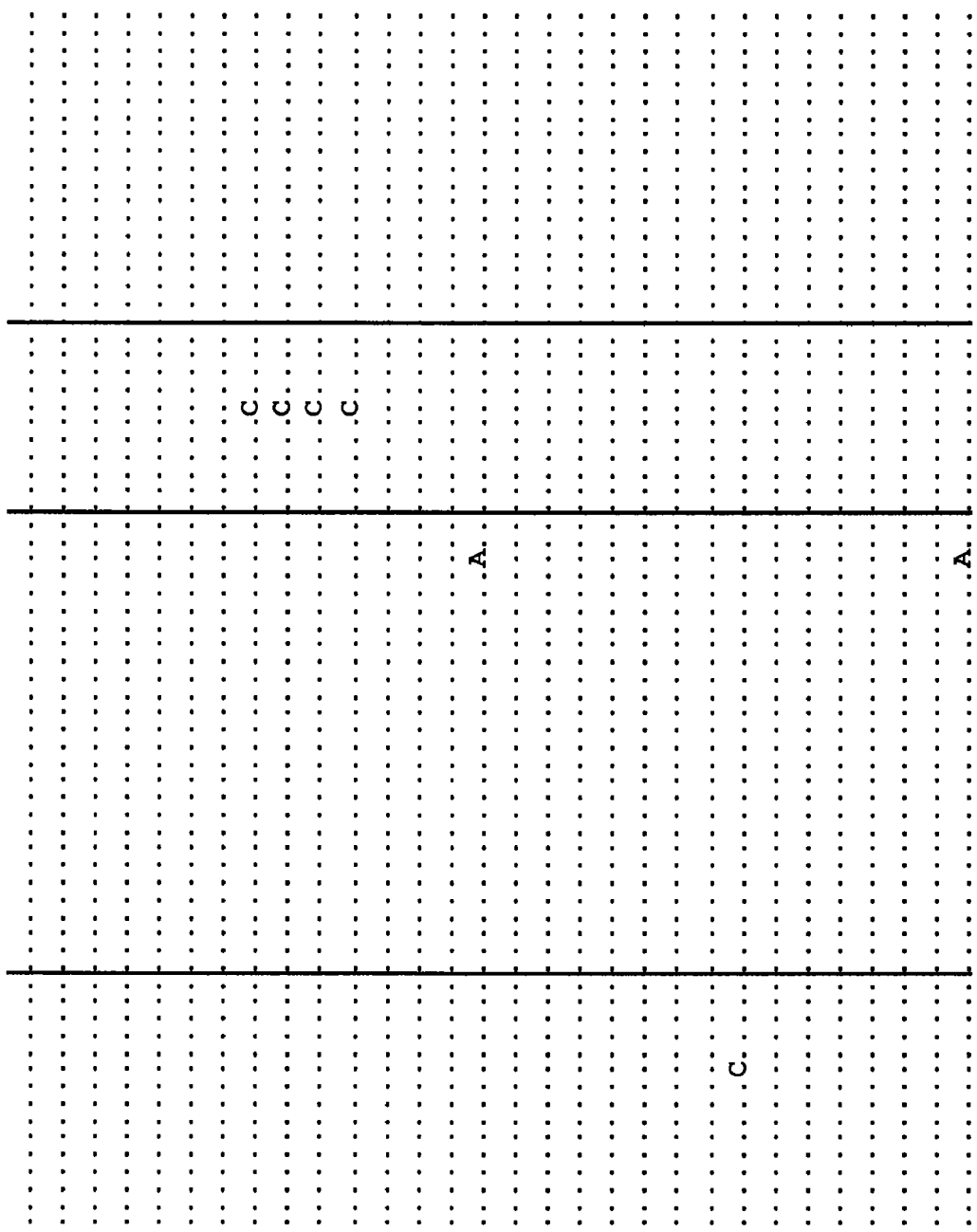
Figure 10F:
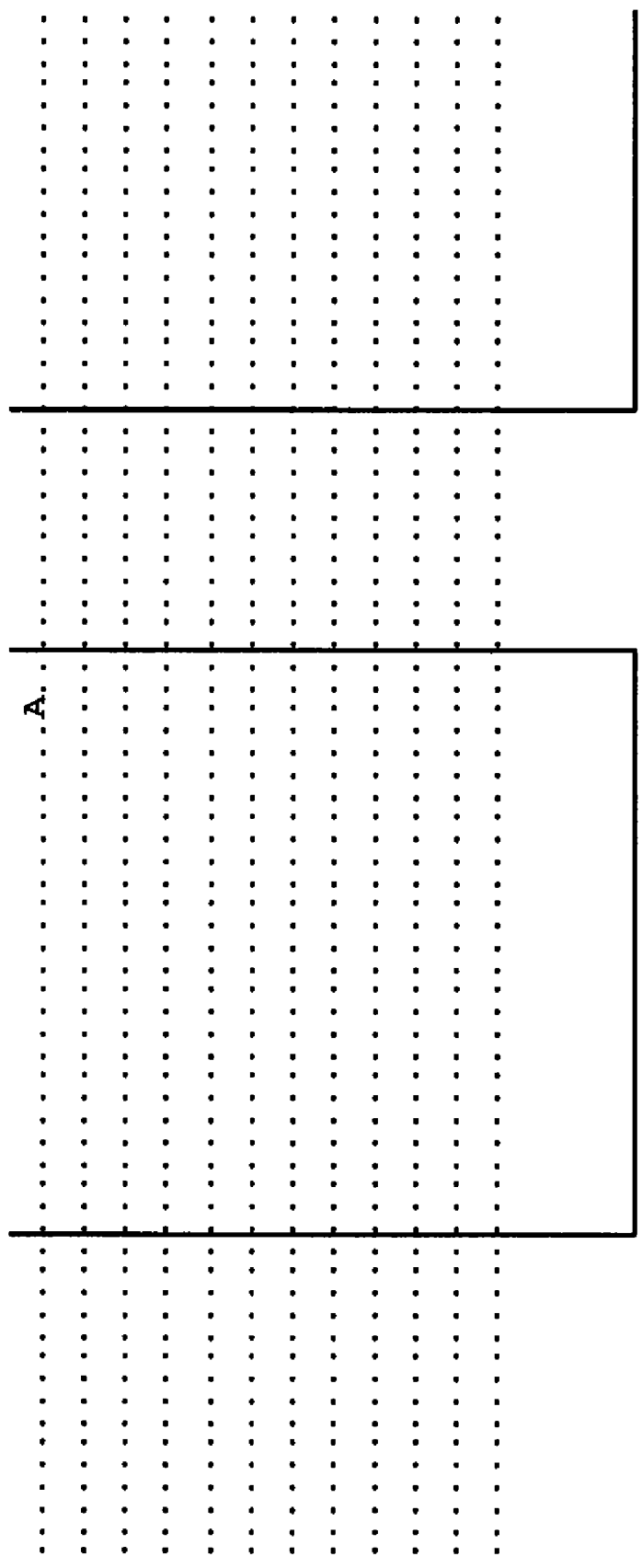
Figure 10G:
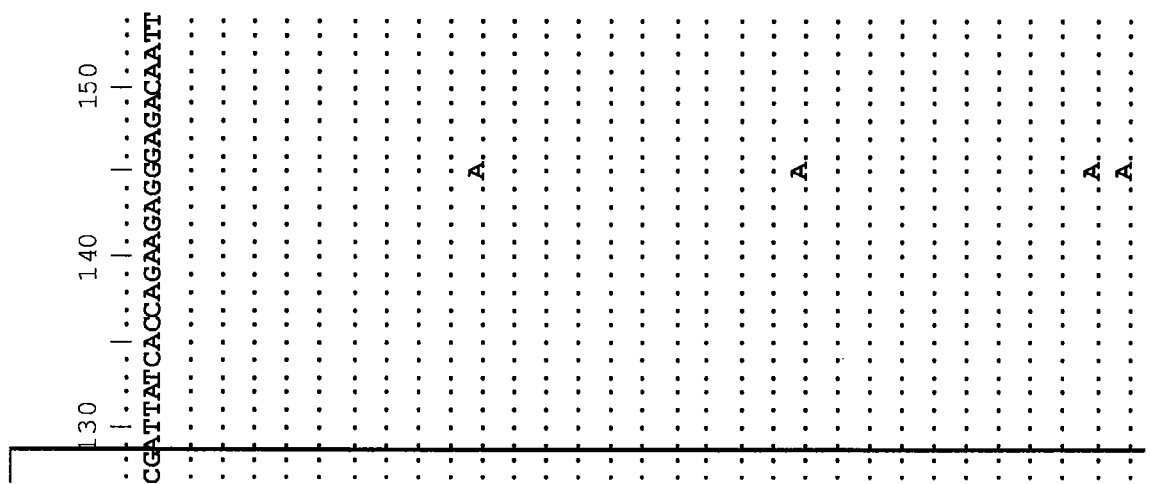
Figure 10H:
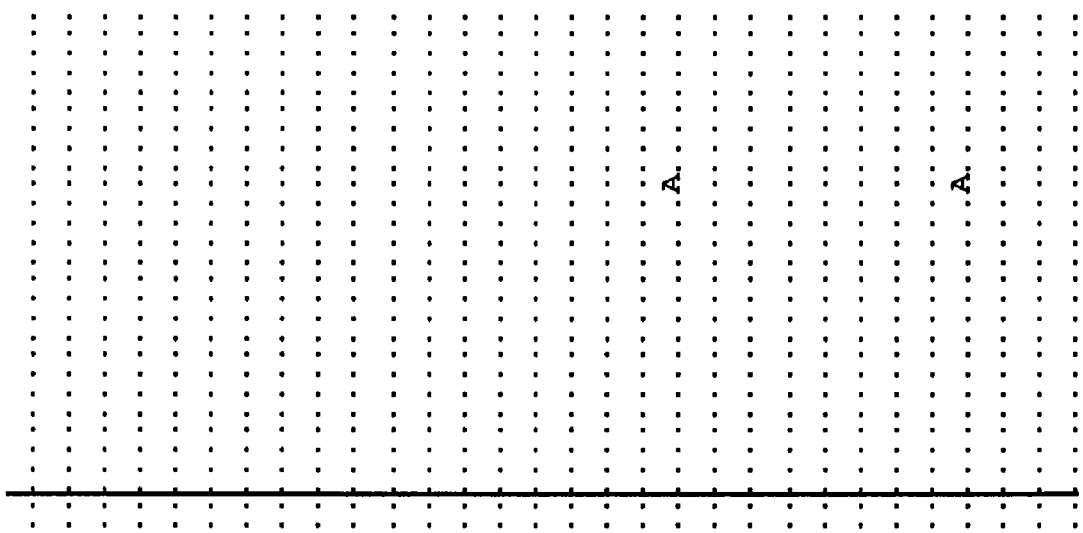
Figure 10I:
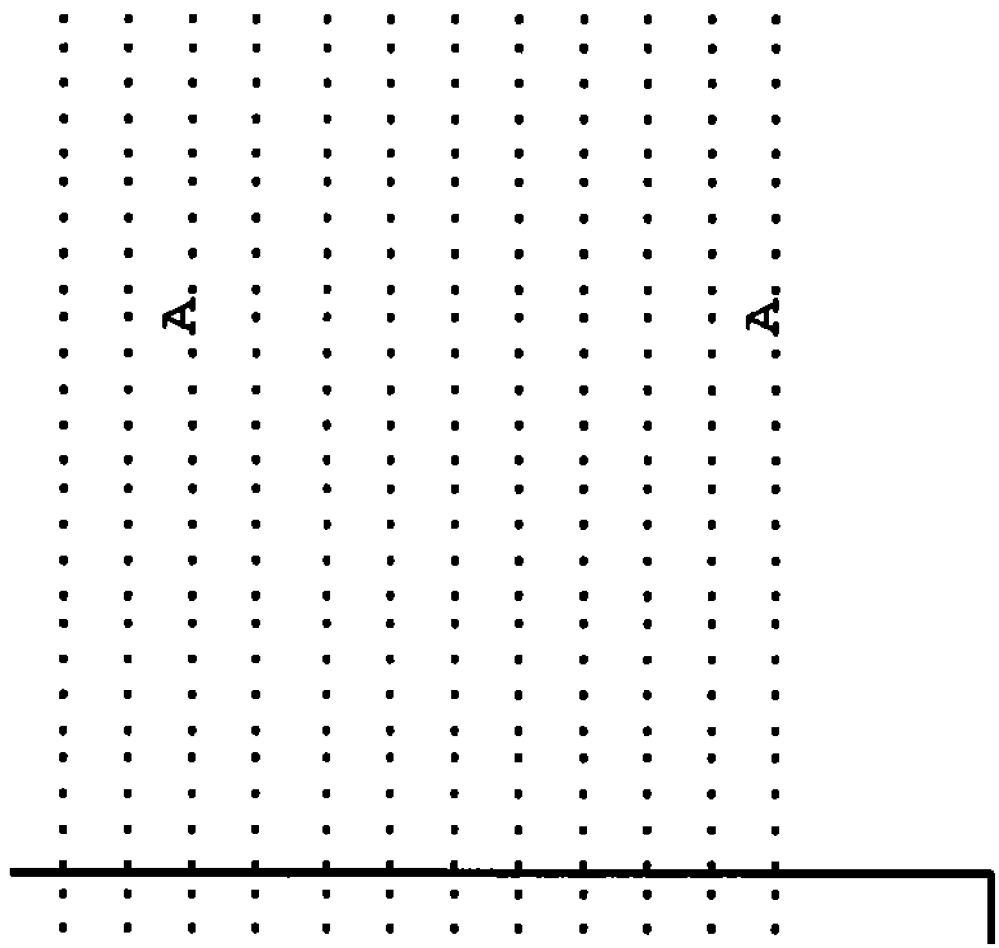
Figure 11A:
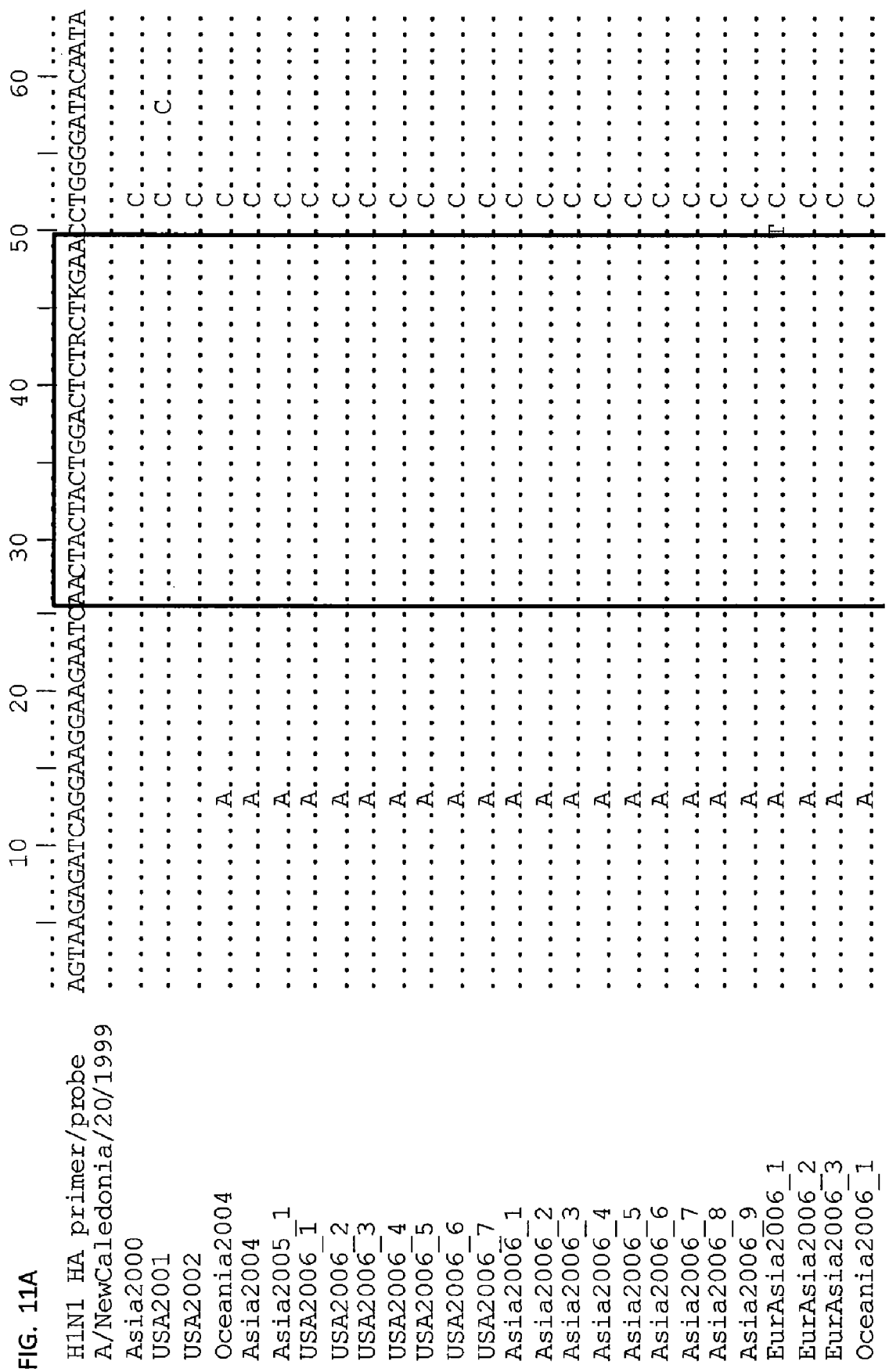
FIG. 11A-11F is a table showing the consensus sequence and variations present in the specified influenza isolates for the region of the influenza subtype H1 HA gene (SEQ ID NO: 44) used to design the disclosed influenza subtype H1 specific probes and primers.
Figure 11B:
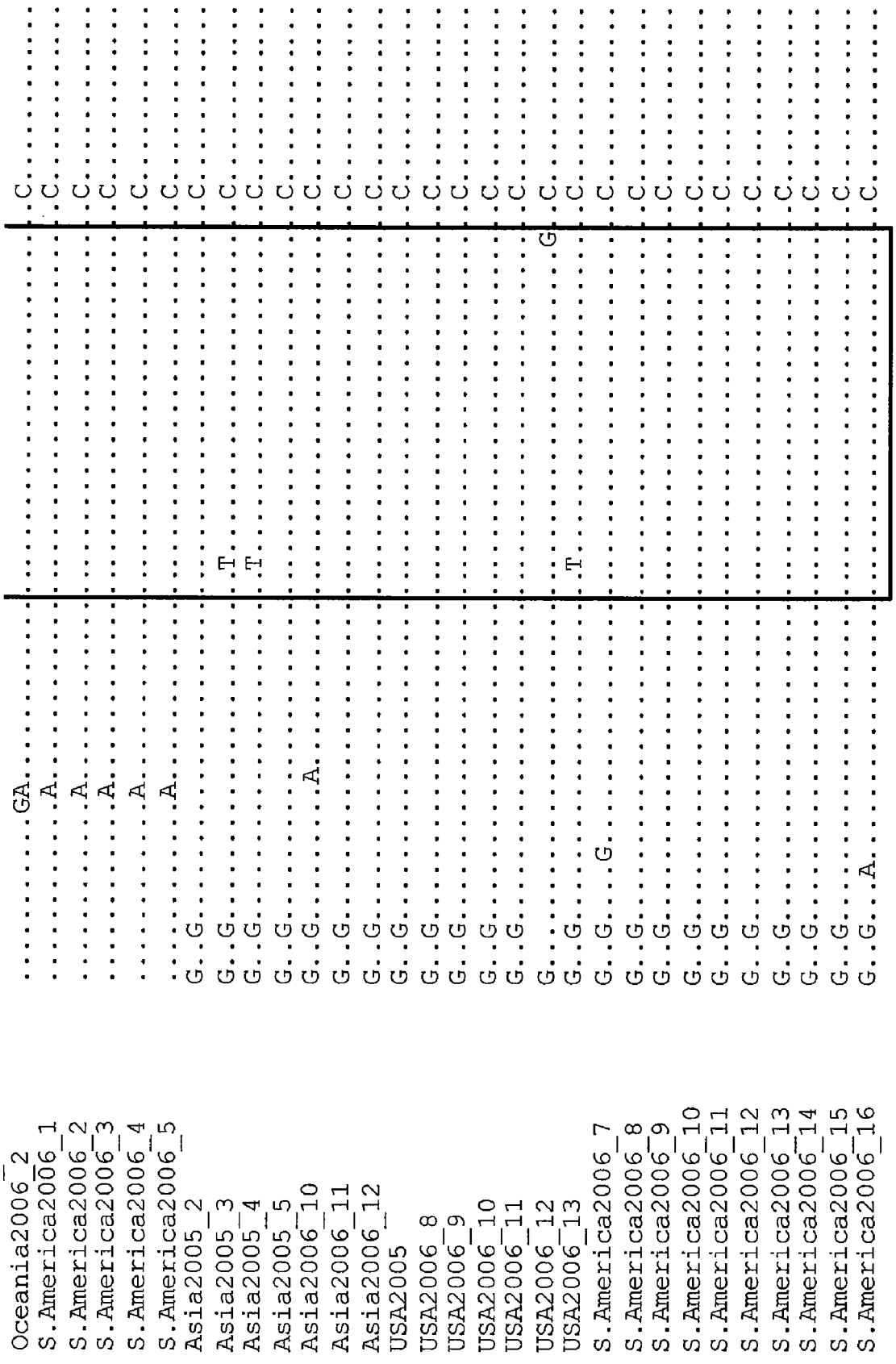
Figure 11C:
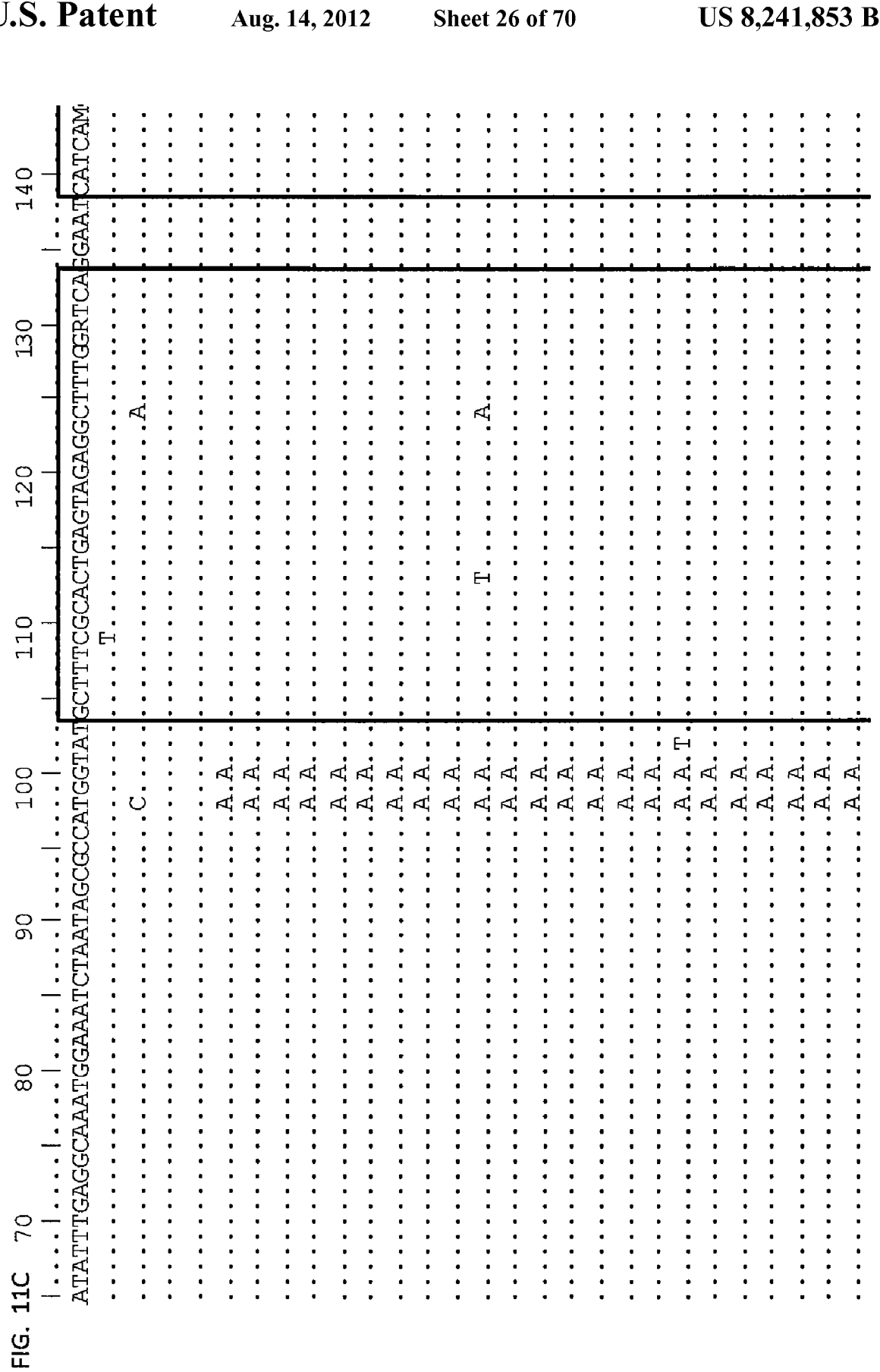
Figure 11D:
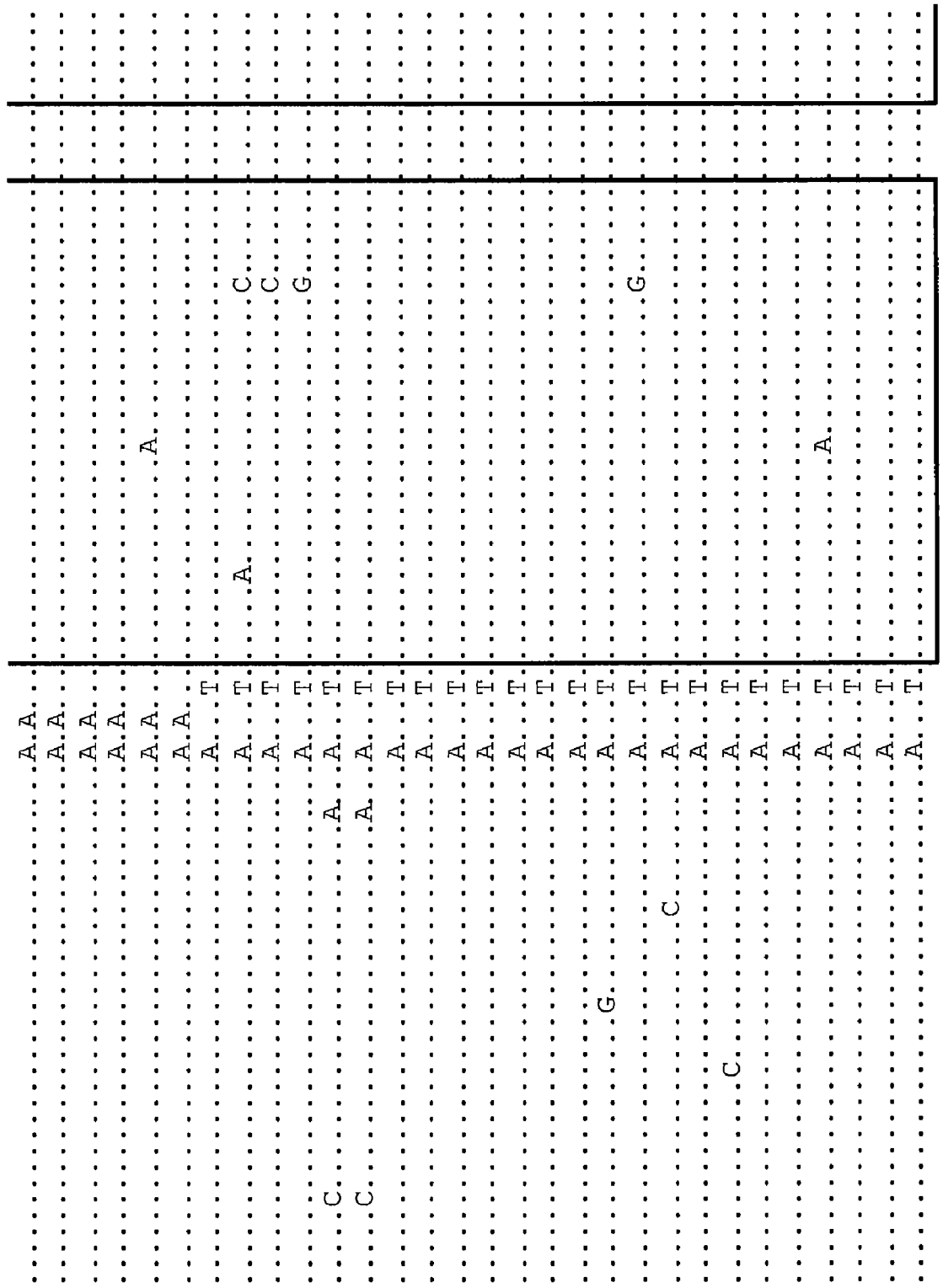
Figure 11E:
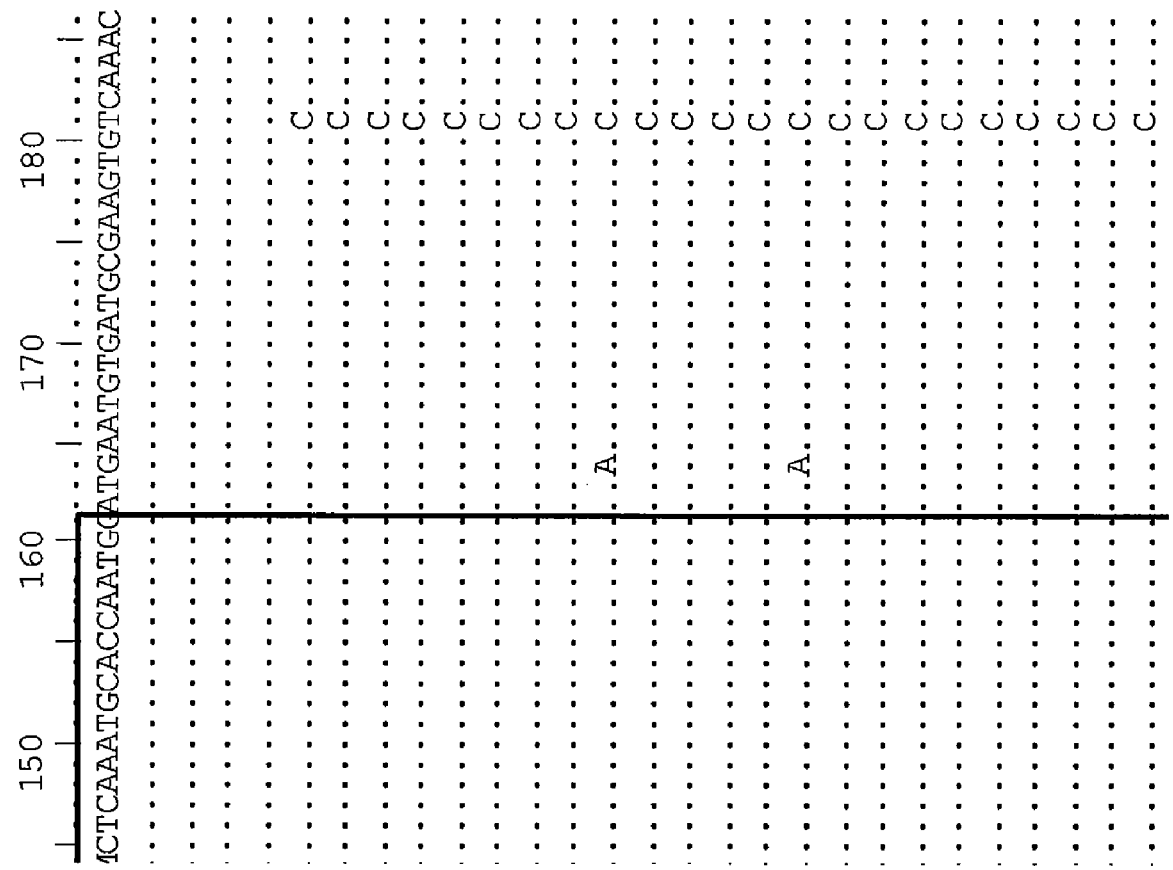
Figure 11F:
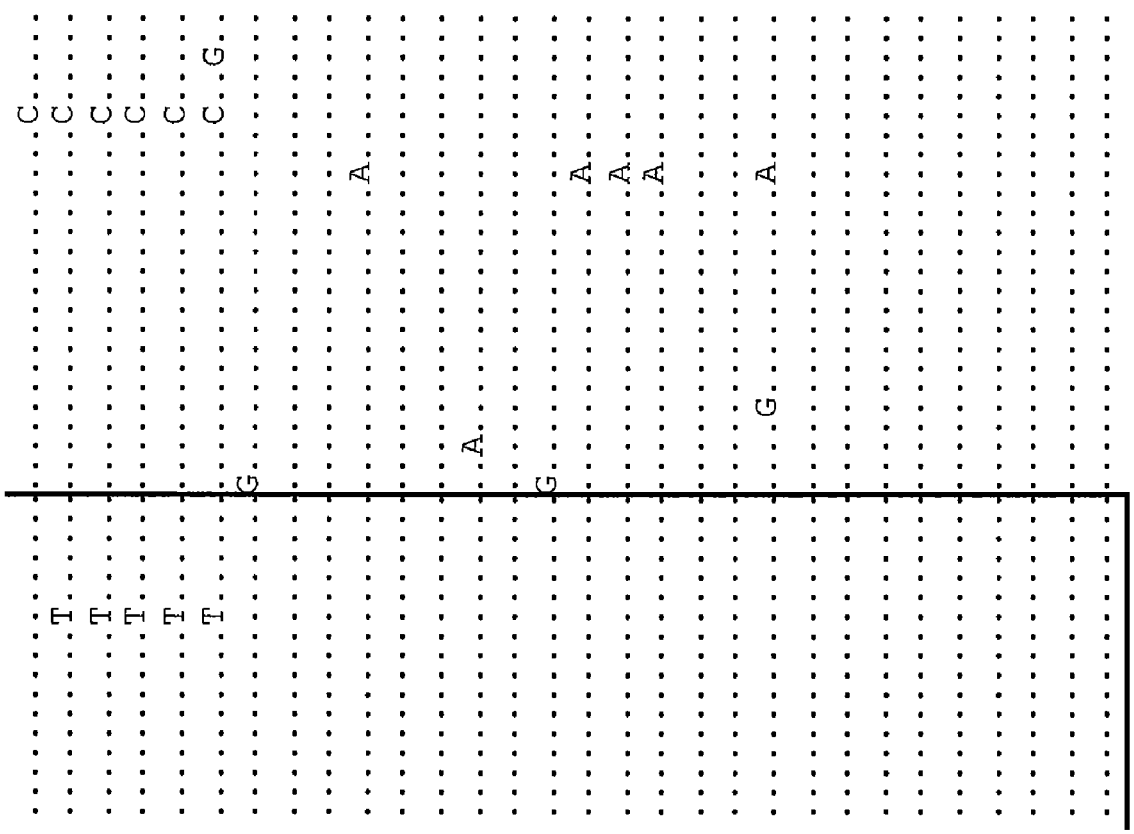
Figure 12A:
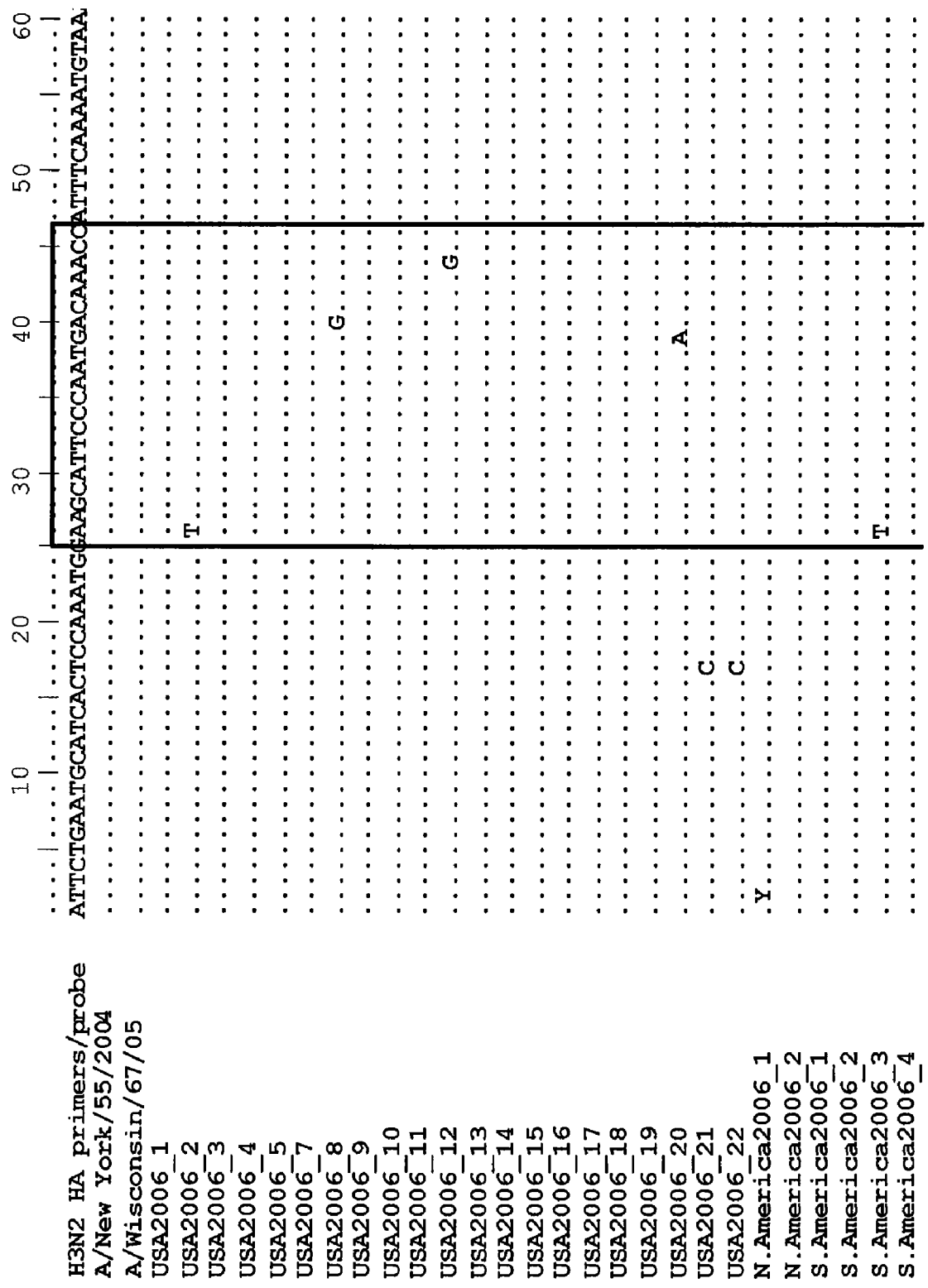
FIG. 12A-12F is a table showing the consensus sequence and variations present in the specified influenza isolates for the region of the influenza subtype H3 HA gene (SEQ ID NO: 45) used to design the disclosed influenza subtype H3 specific probes and primers.
Figure 12B:
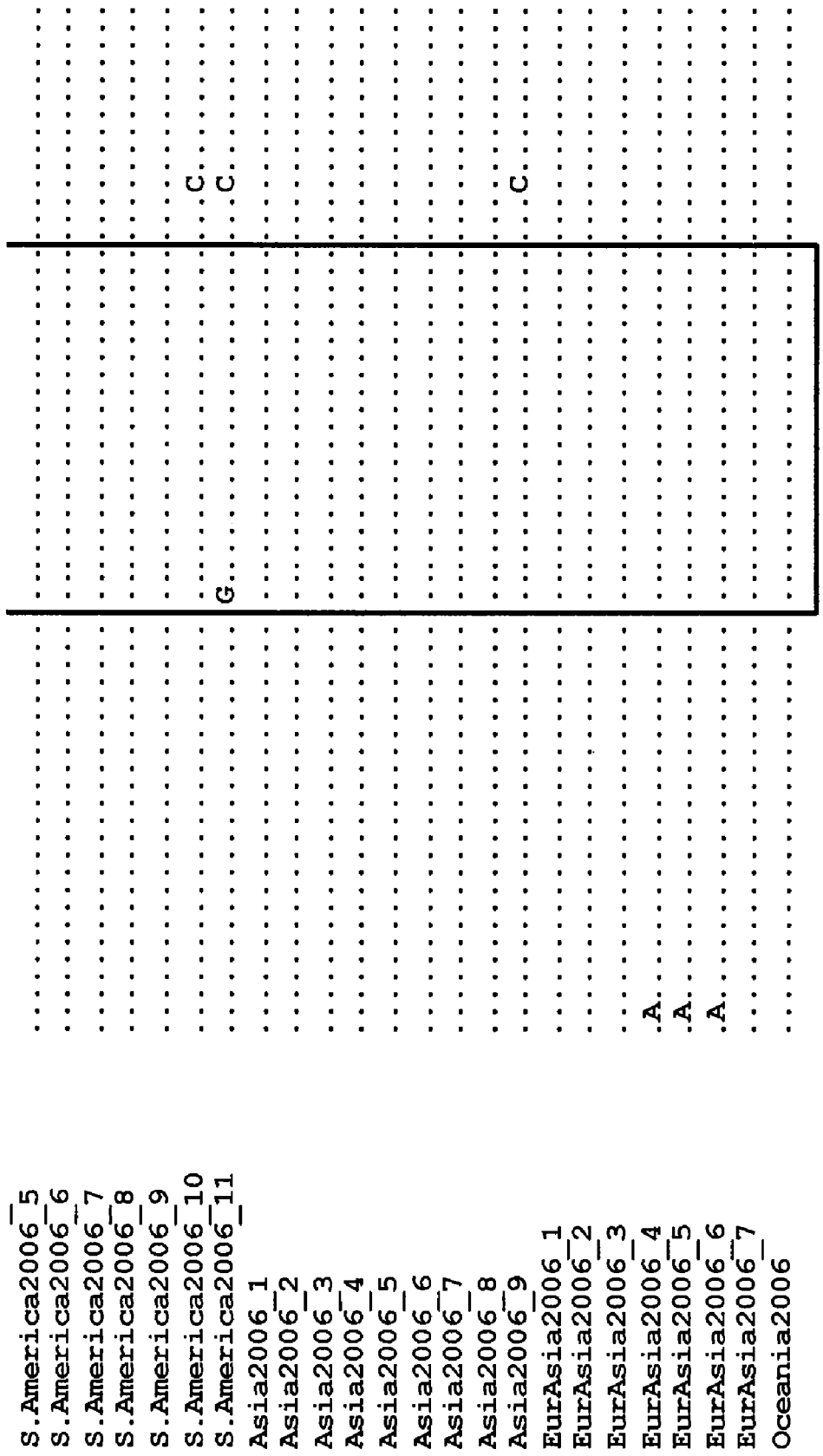
Figure 12C:
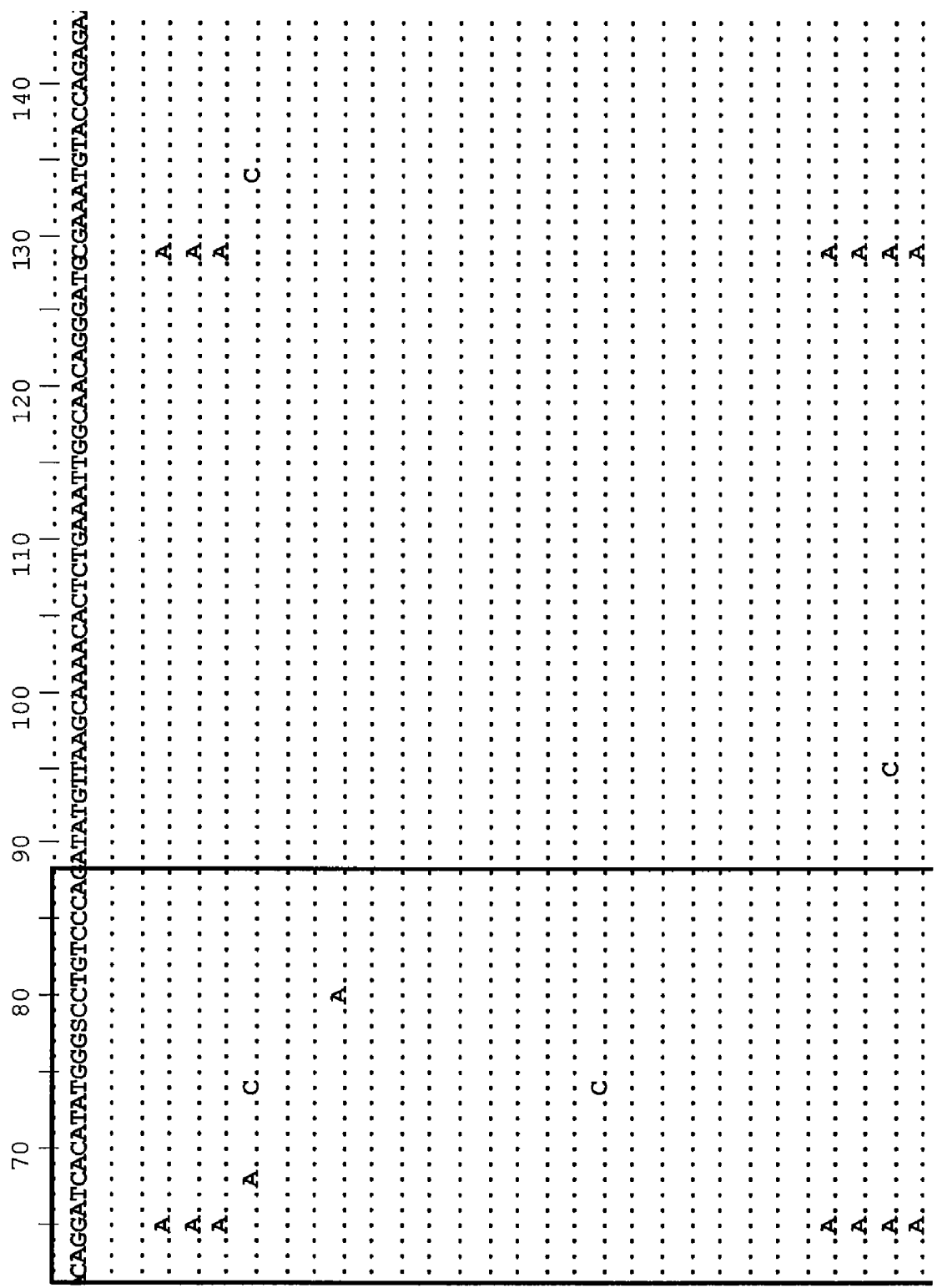
Figure 12D:
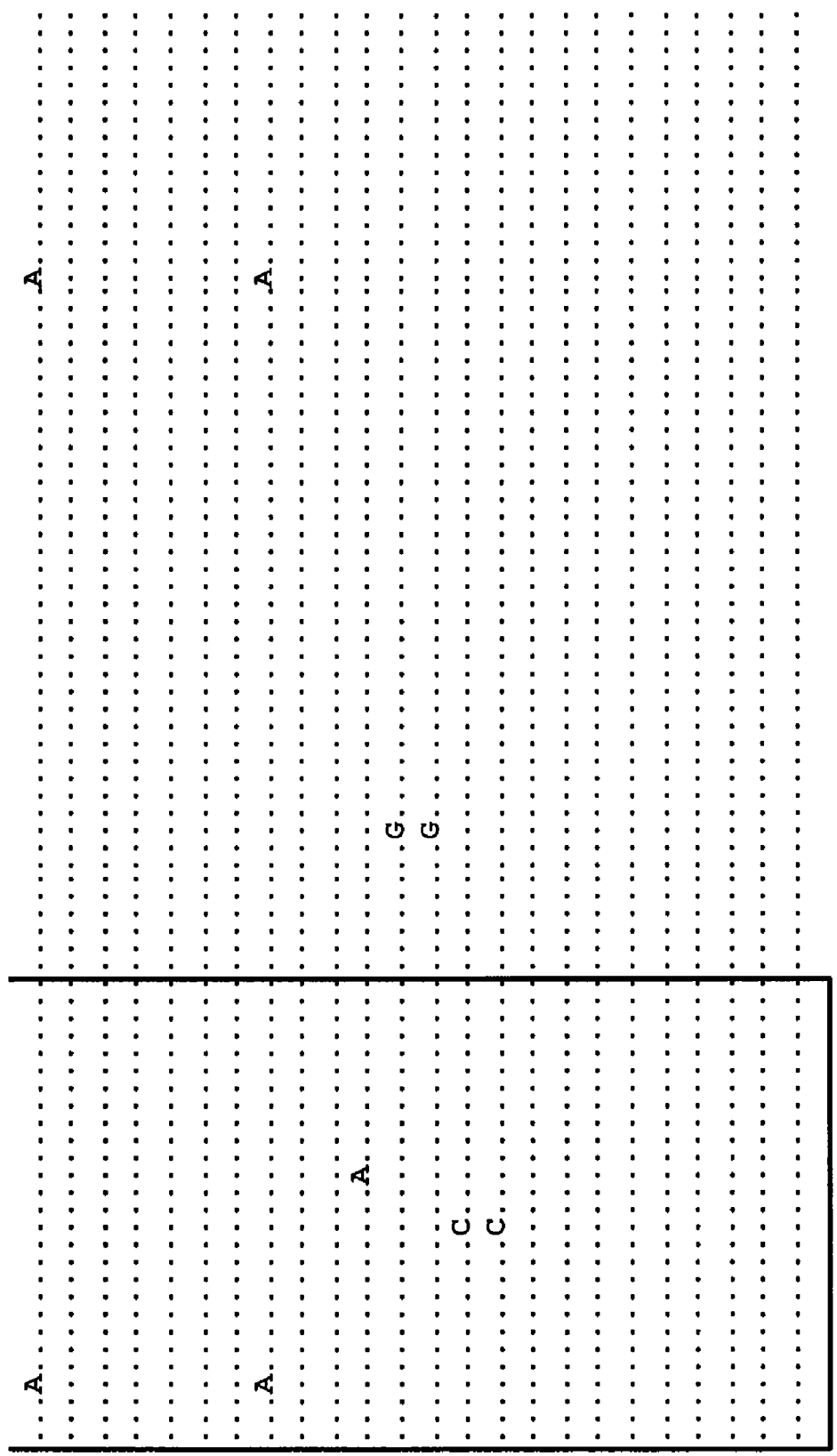
Figure 12E:
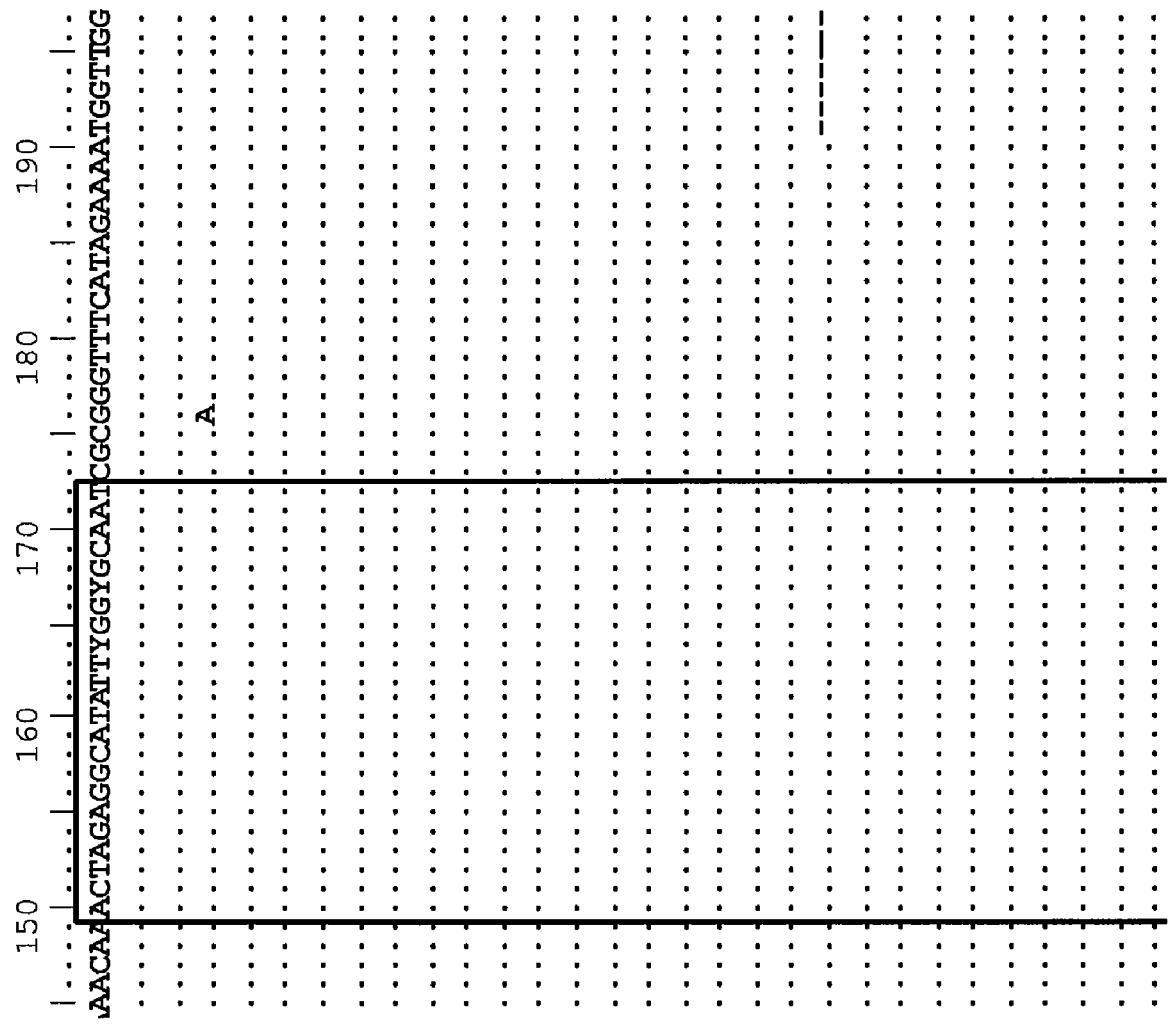
Figure 12F:
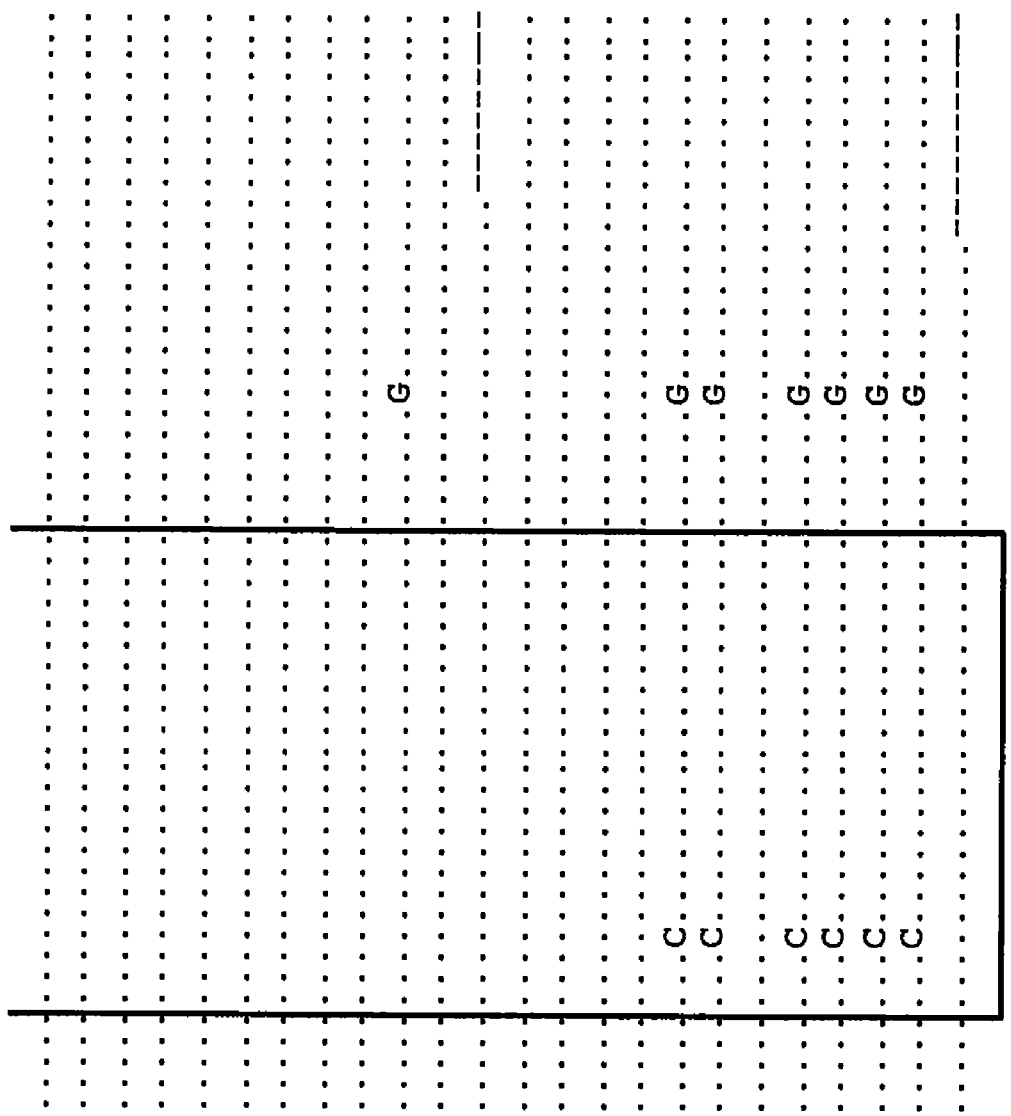
Figure 13A:
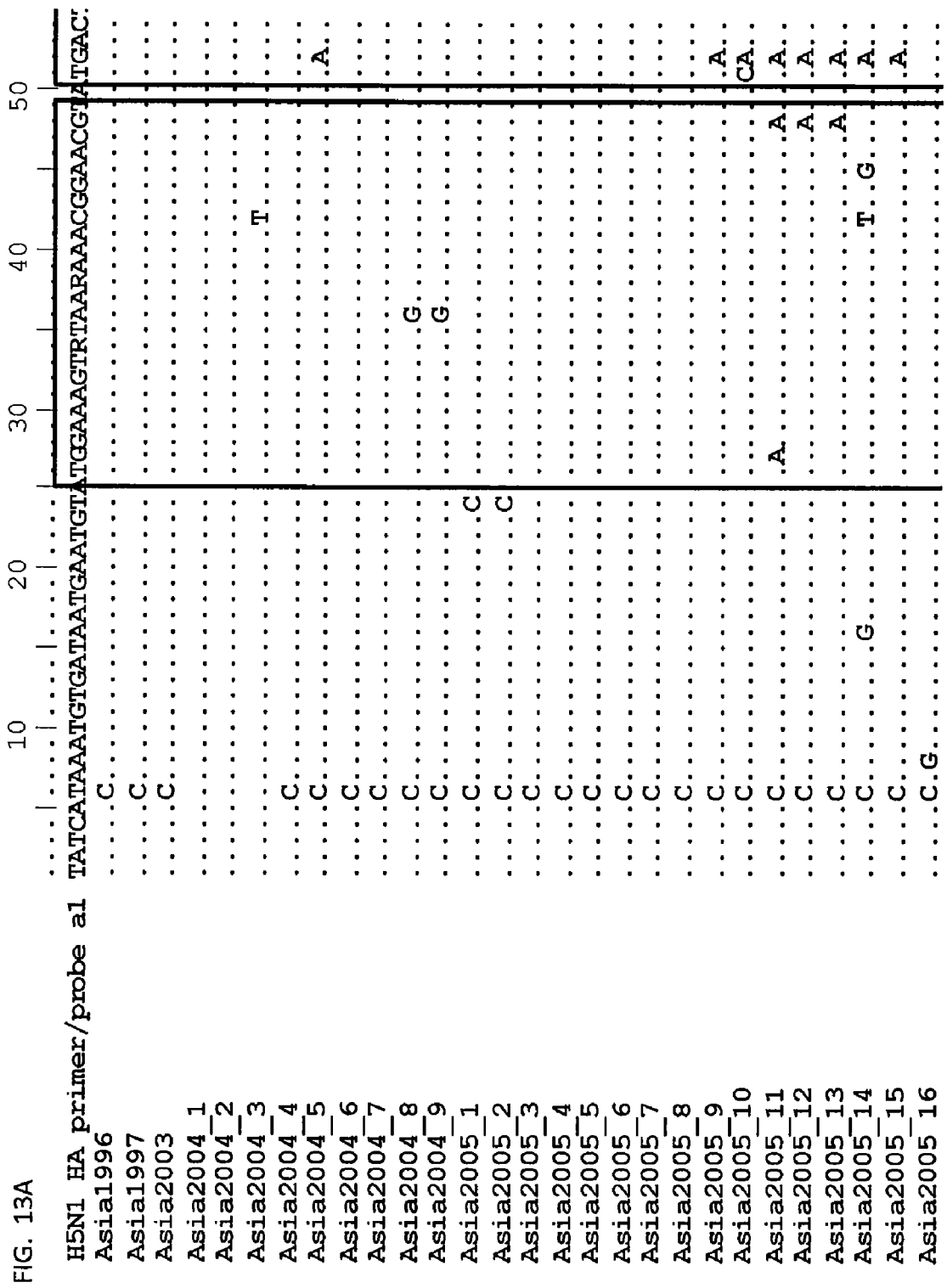
Figure 13C:
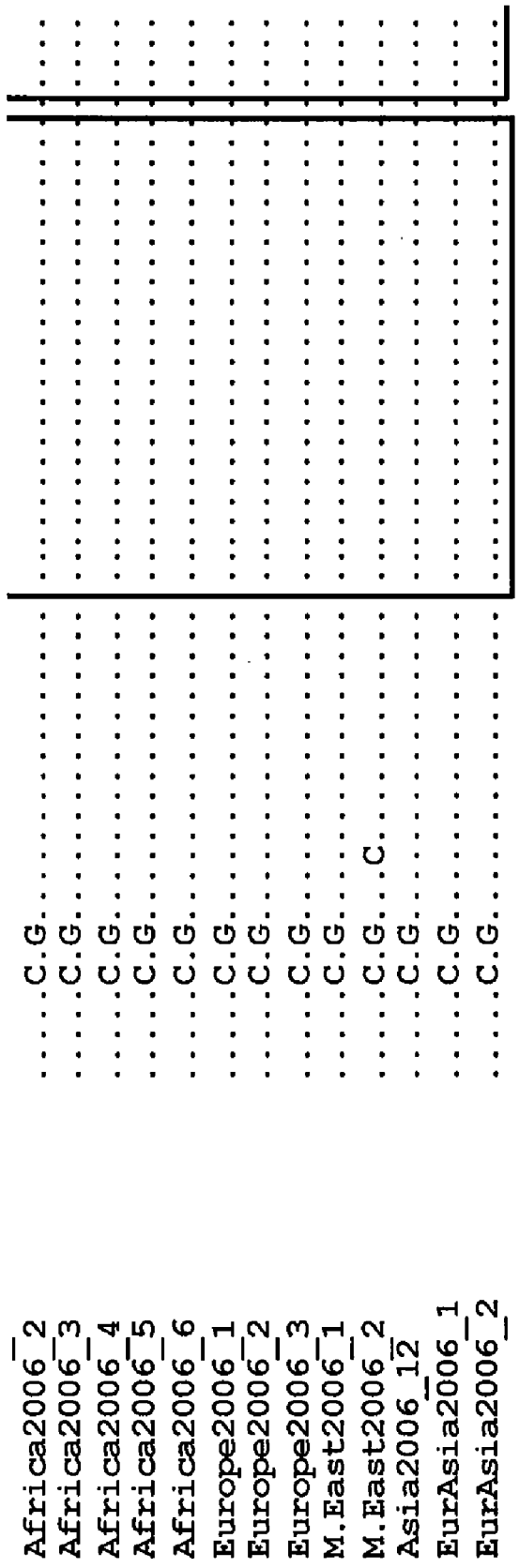
Figure 13D:
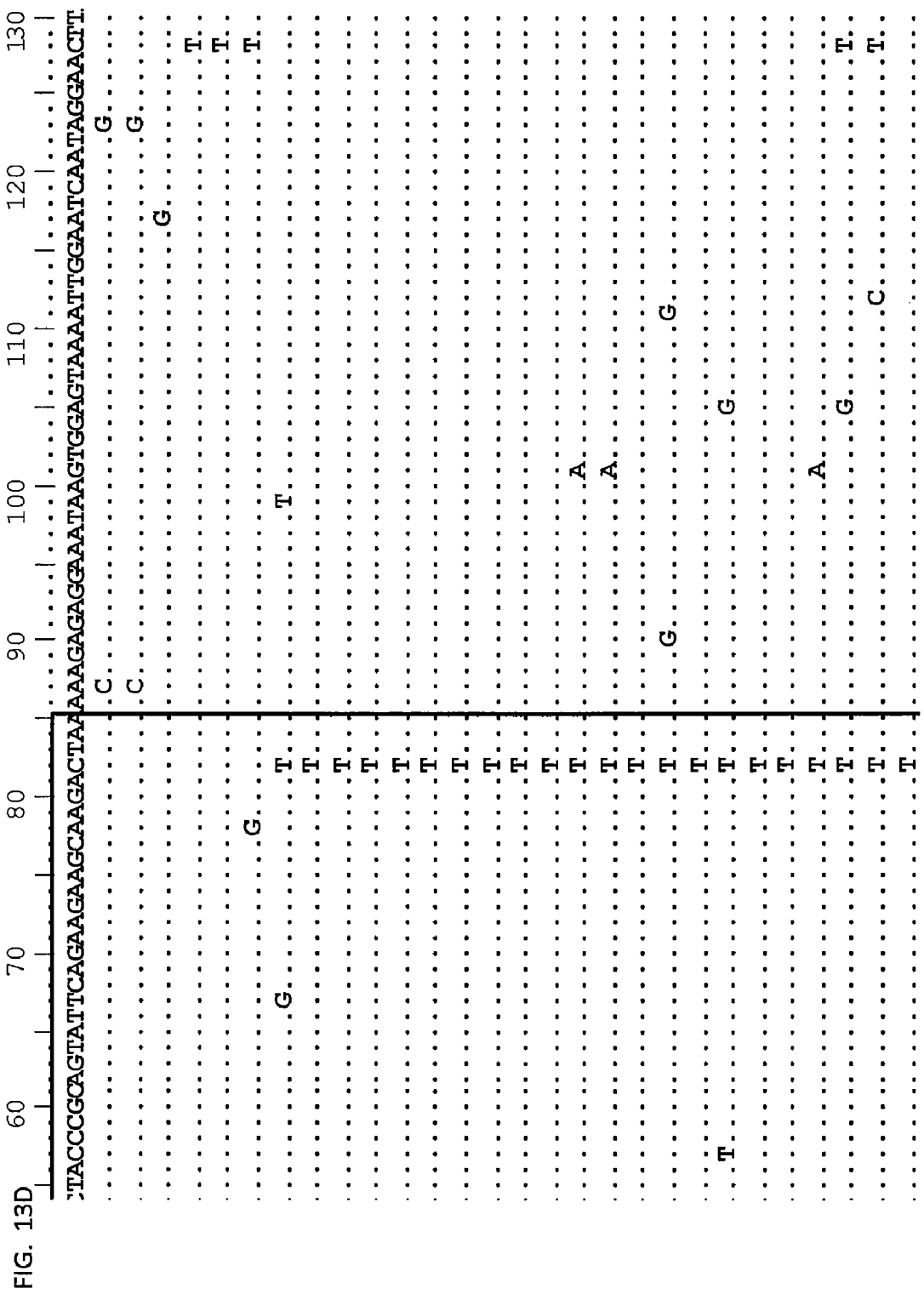
Figure 13E:
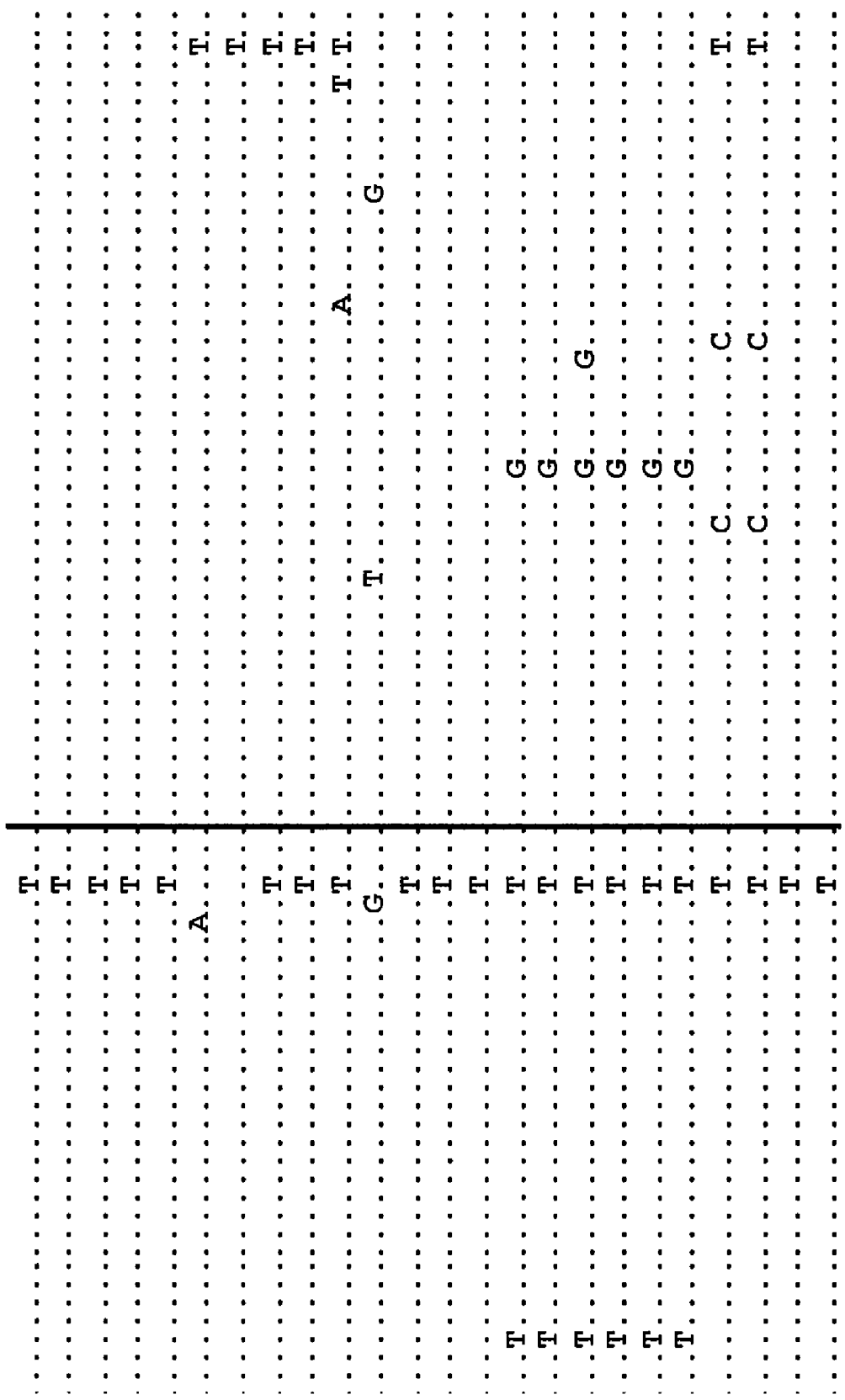
Figure 13F:
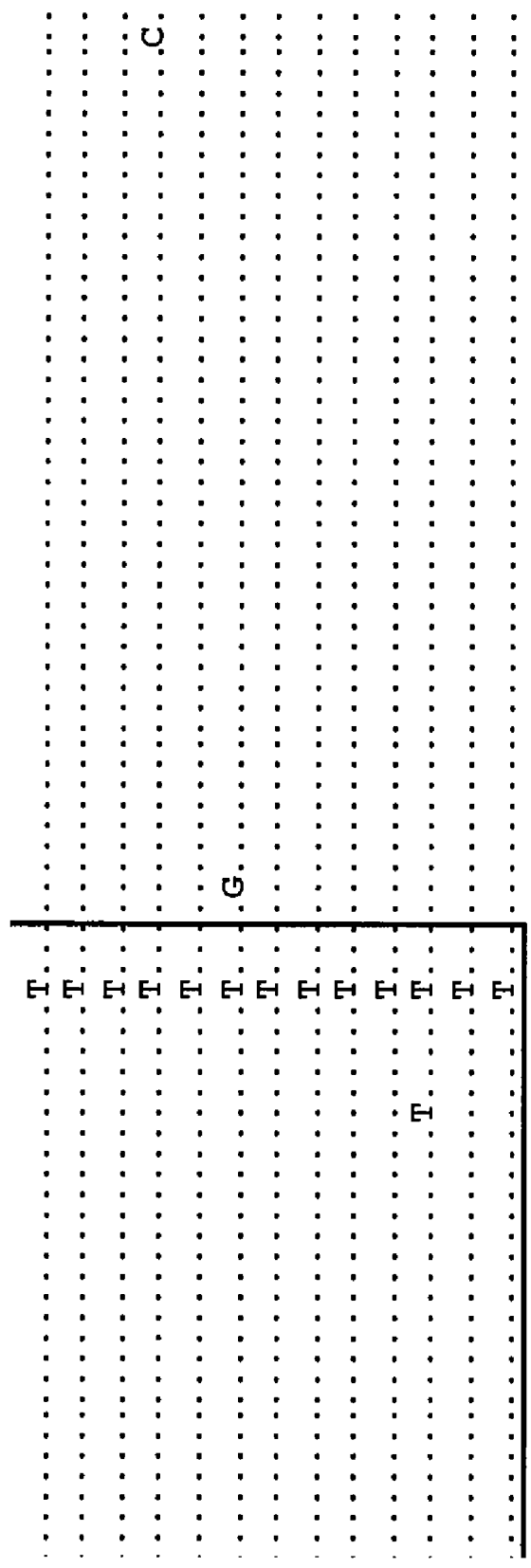
Figure 13I:
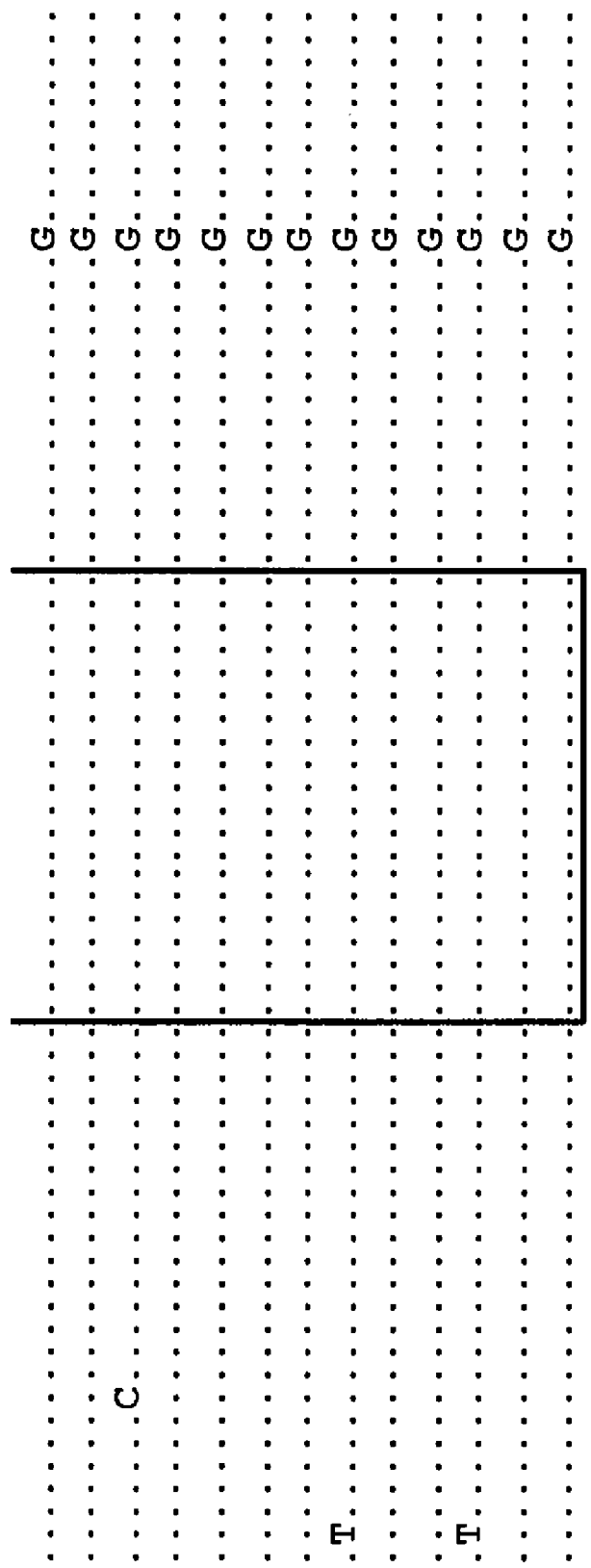
Figure 14A:
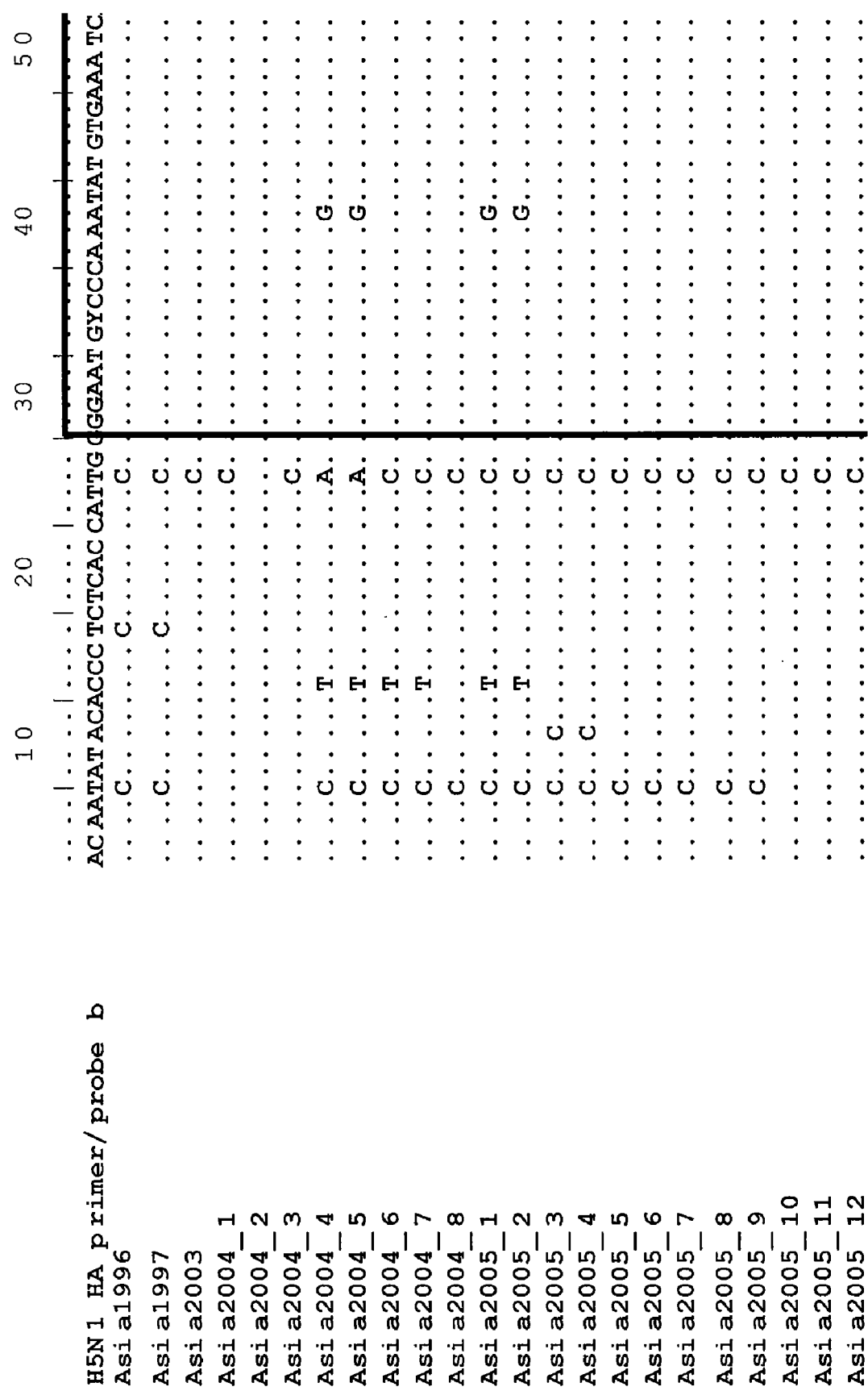
Figure 14B:
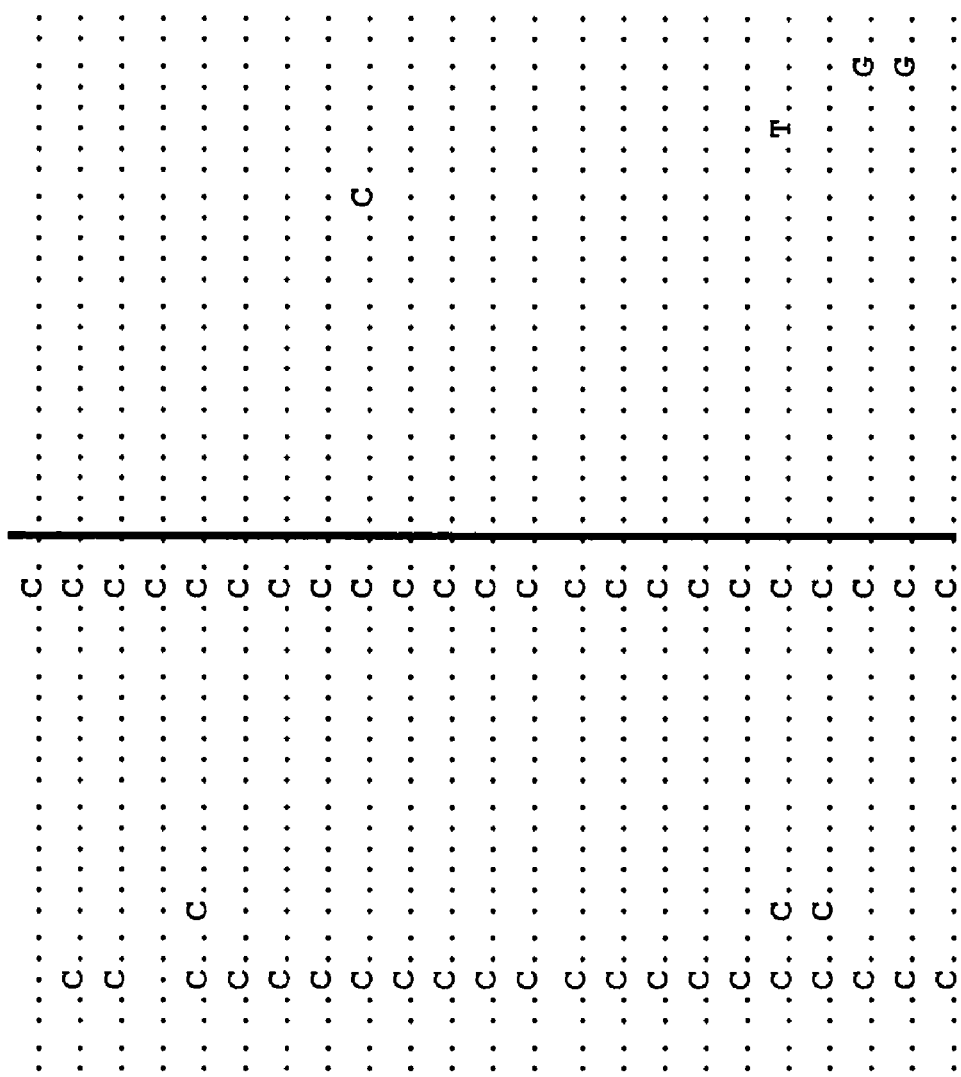
Figure 14C:
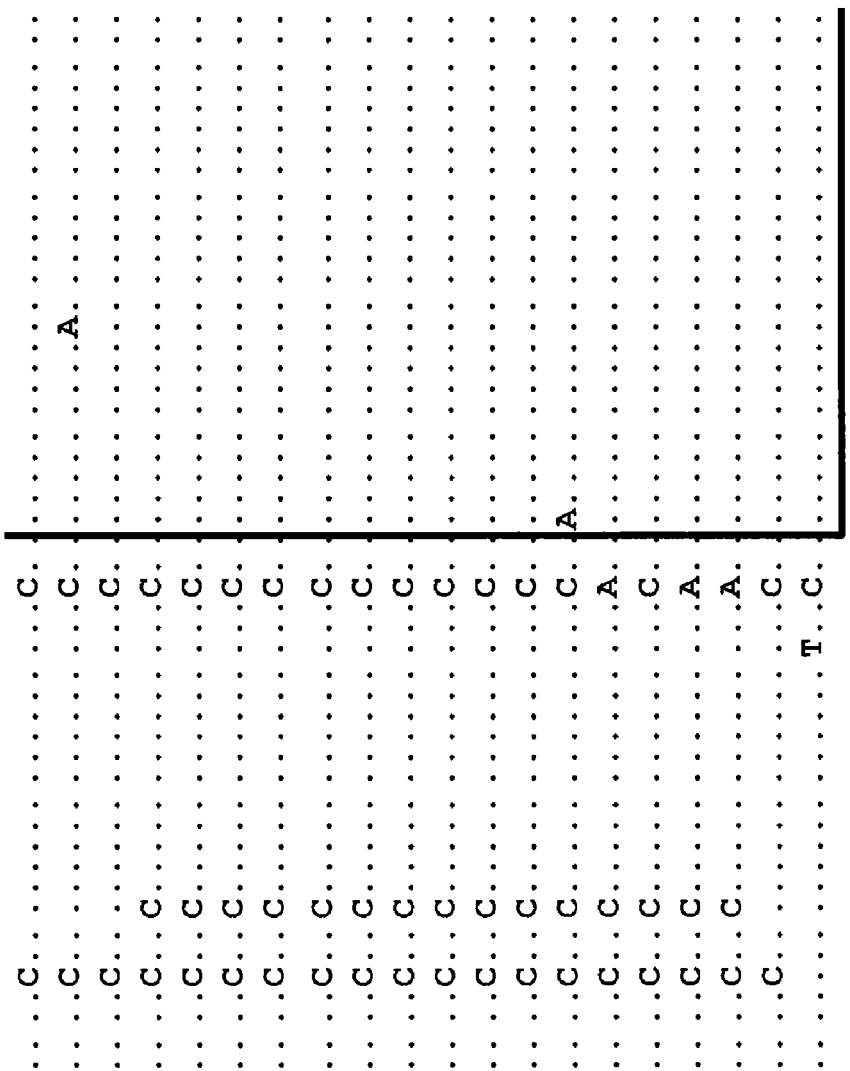
Figure 14G:
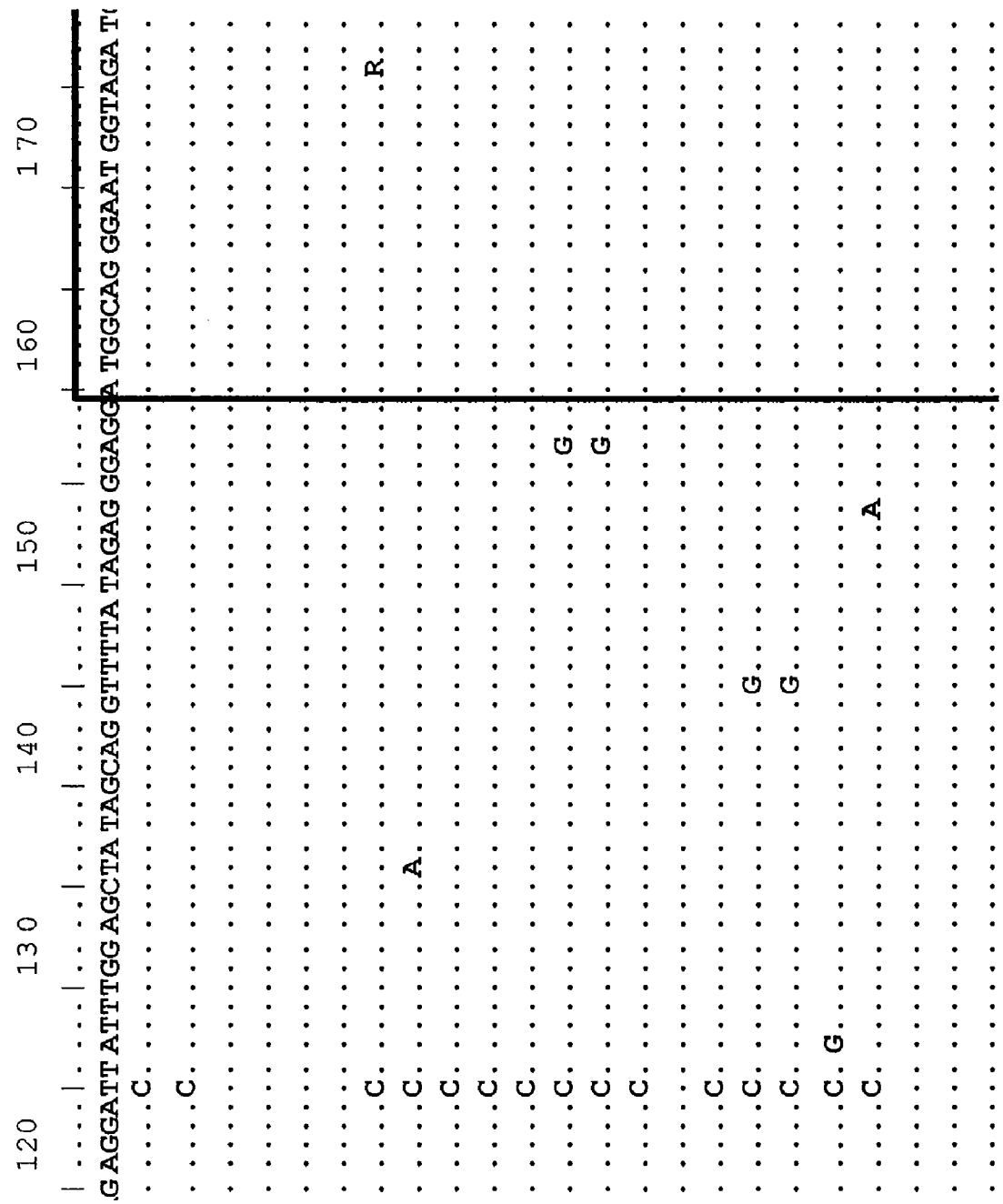
Figure 14H:
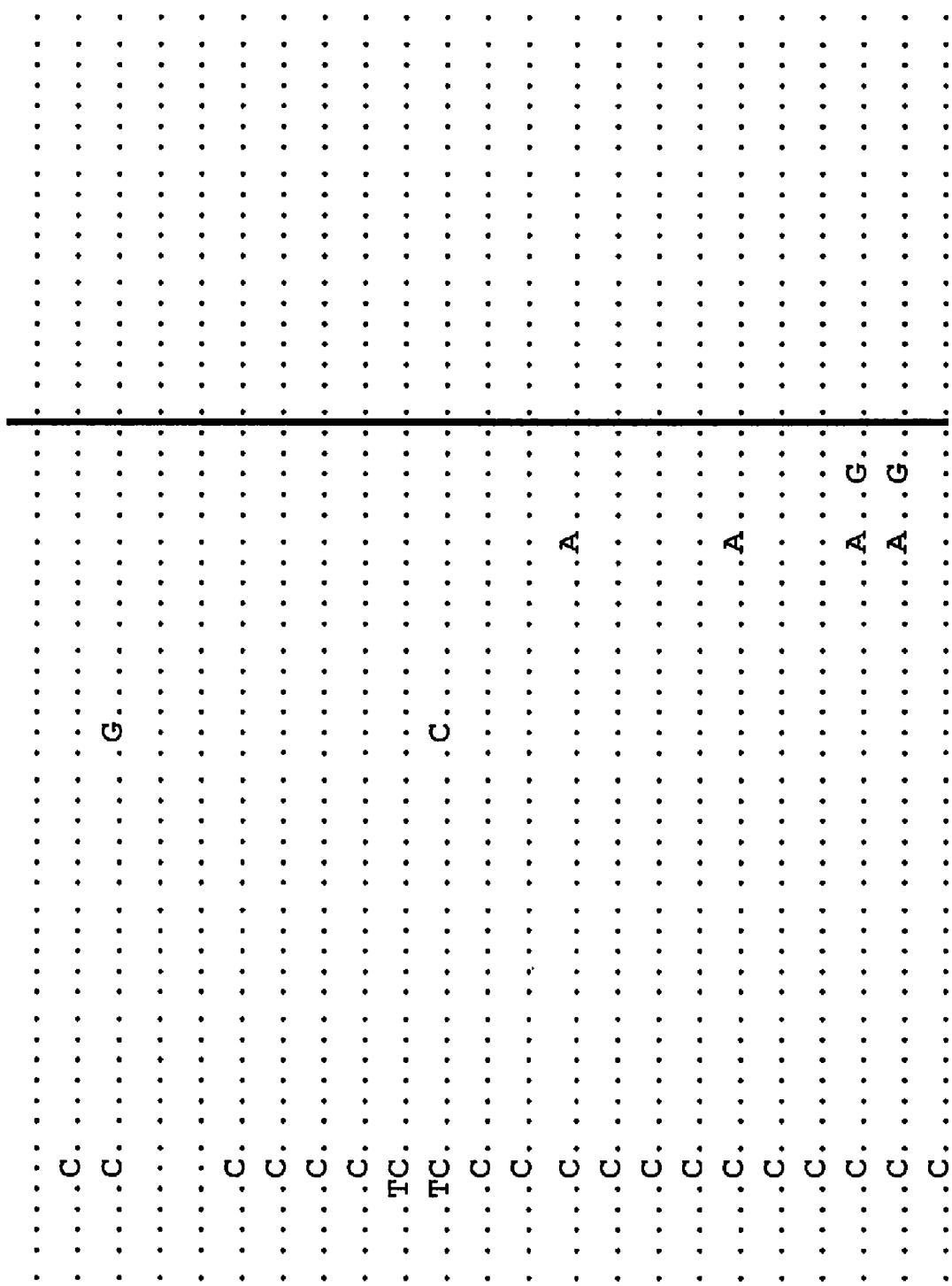
Figure 14I:
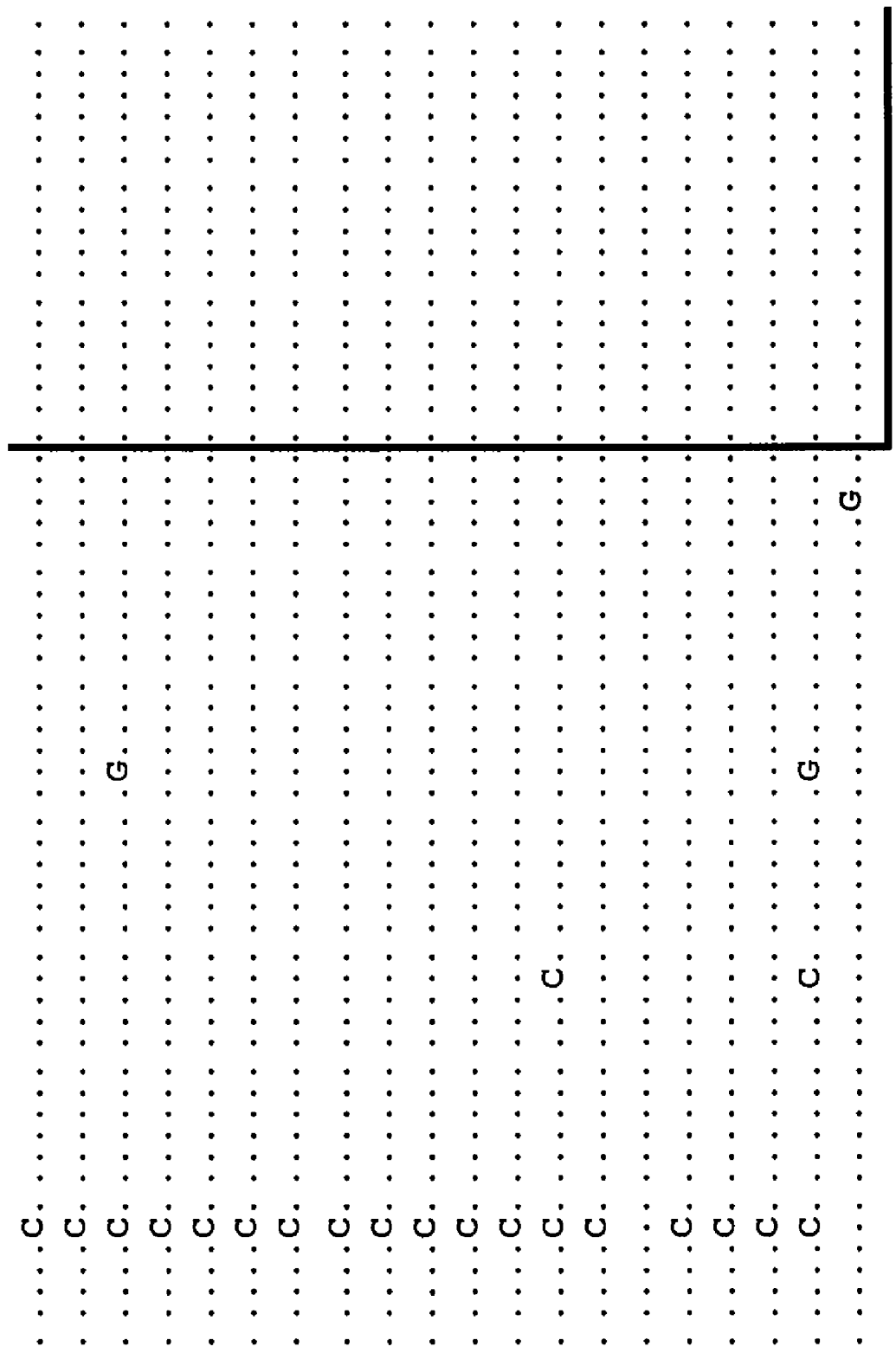
Figure 14J:
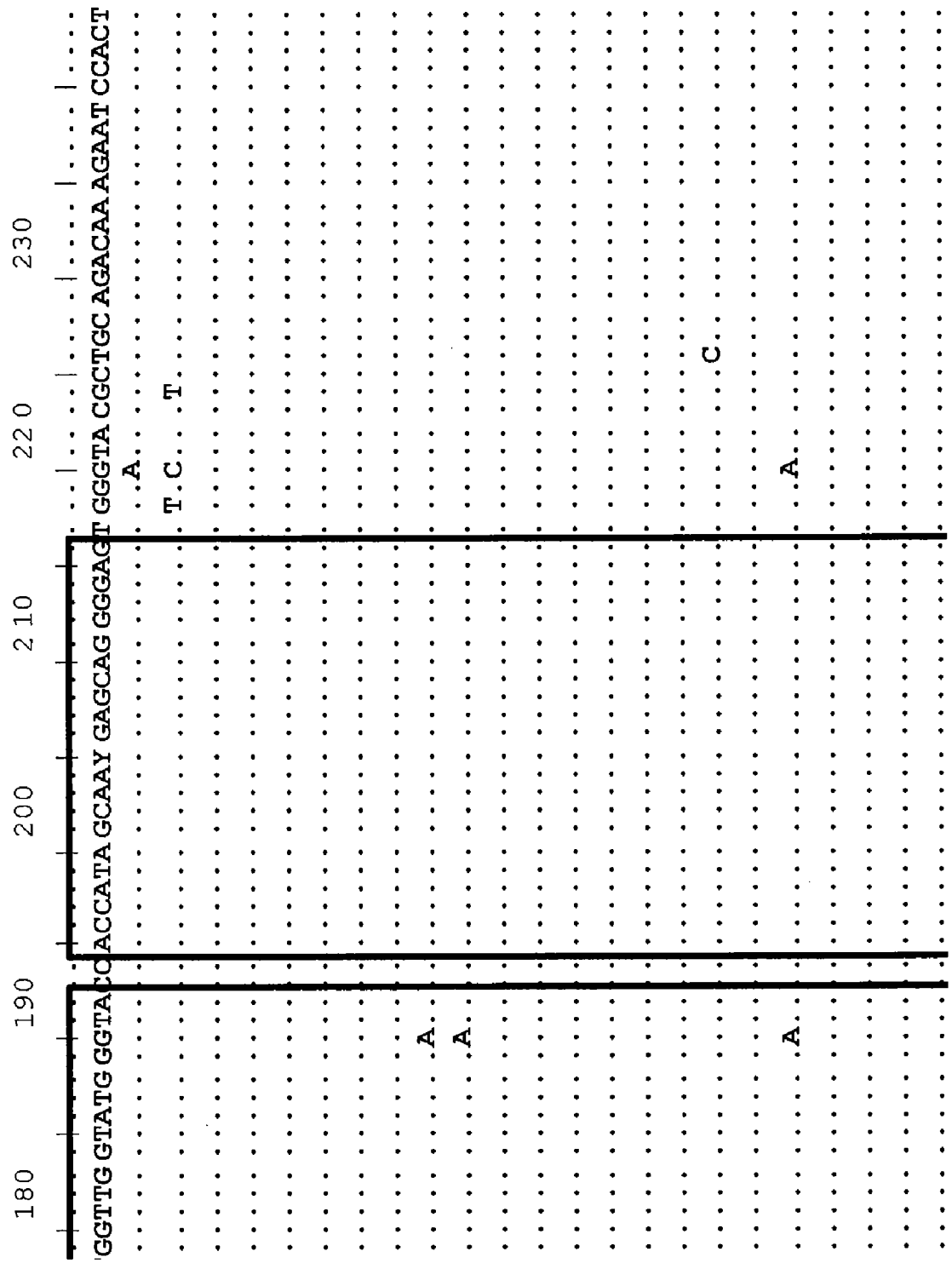
Figure 14K:
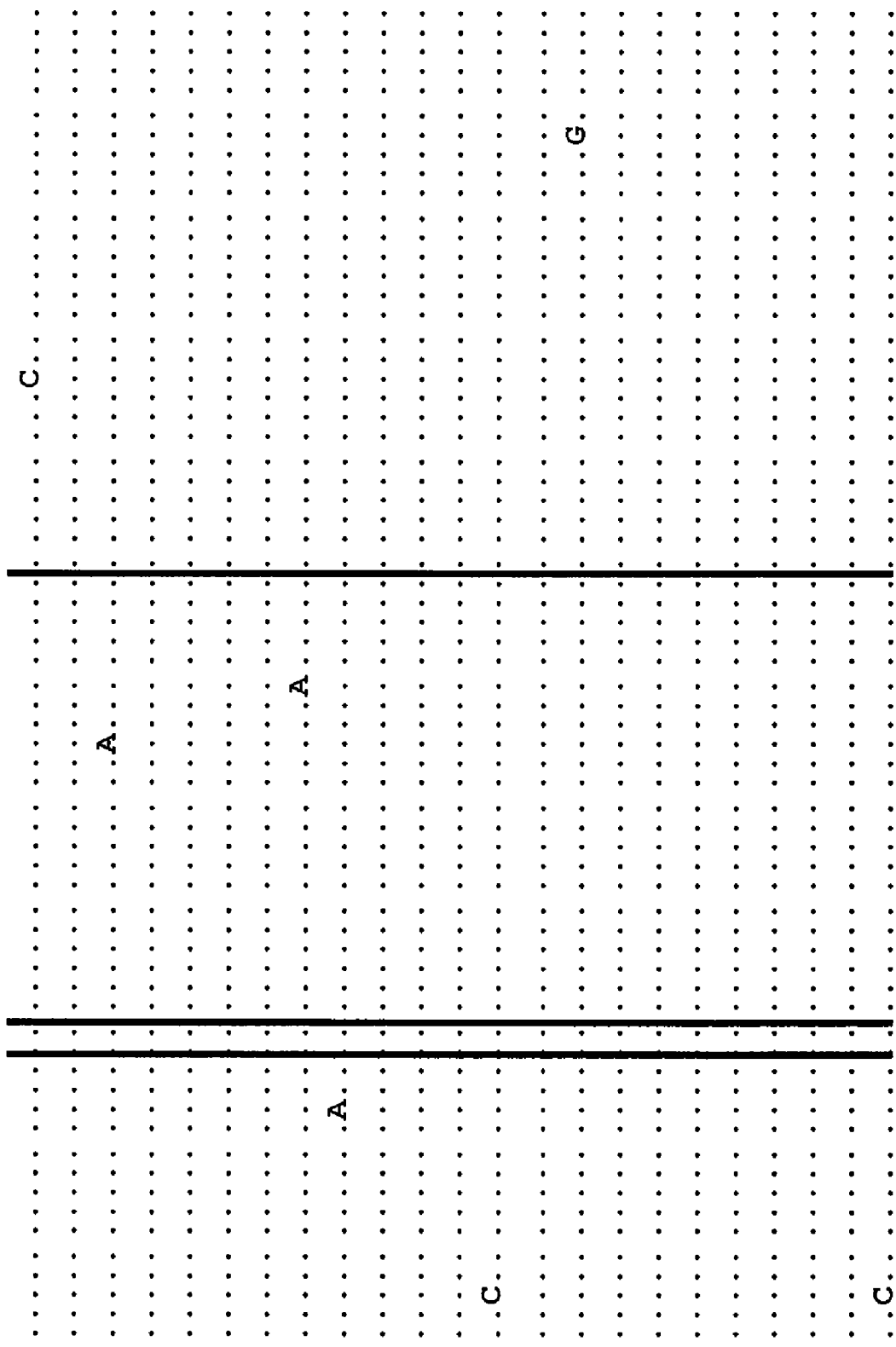
Figure 14L:
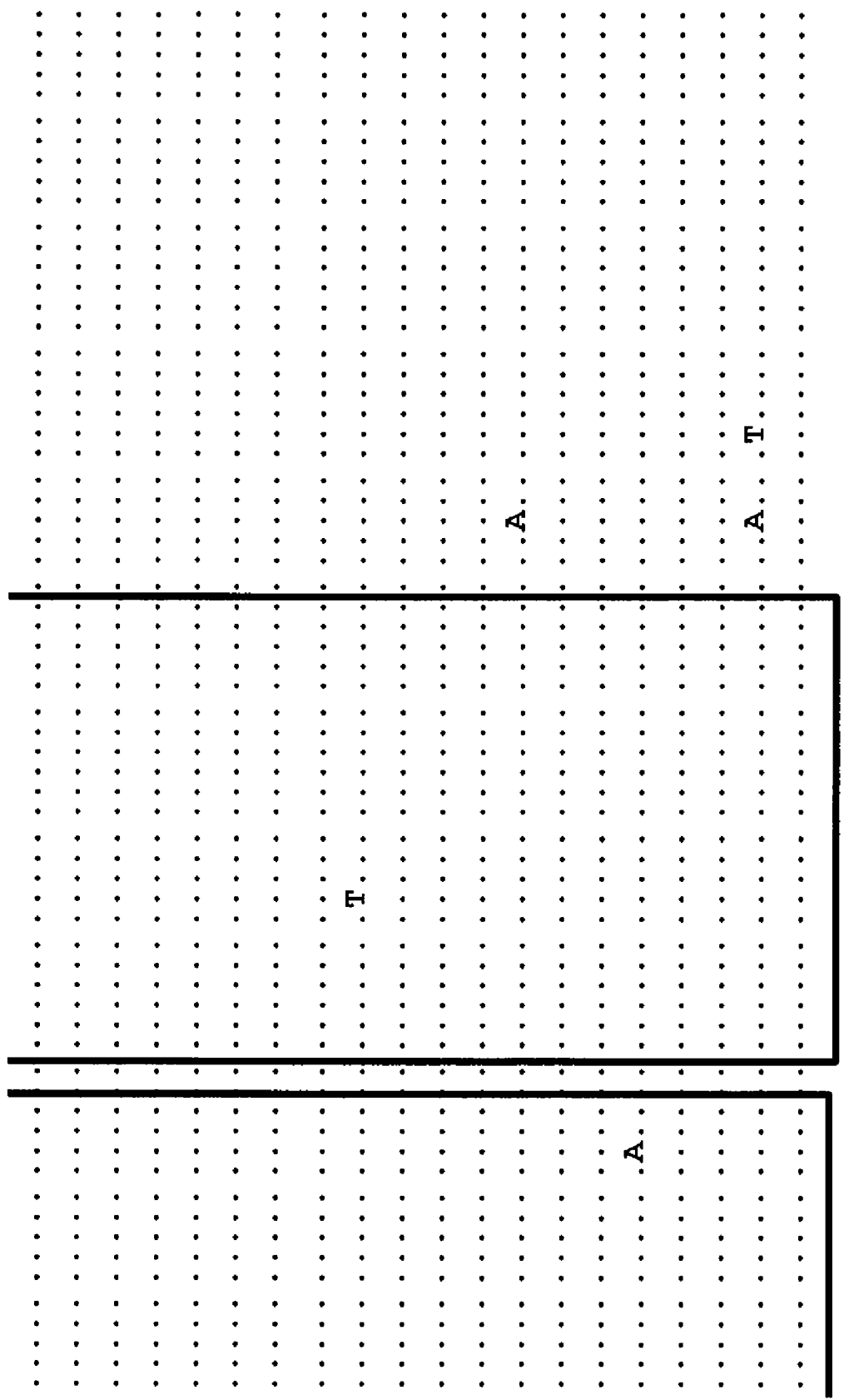
Figure 15A:
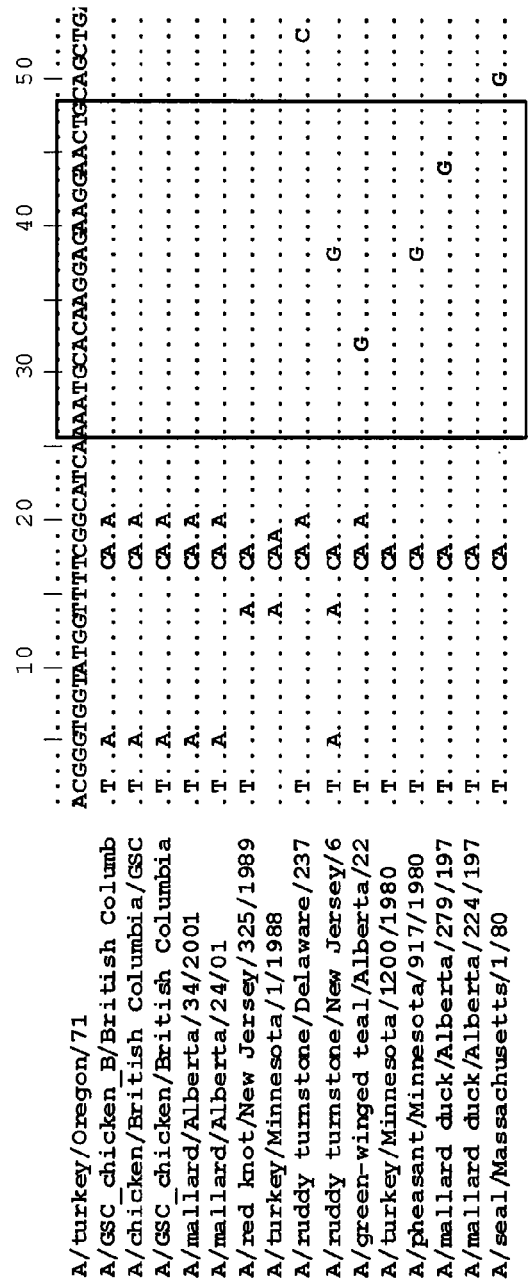
Figure 15A:
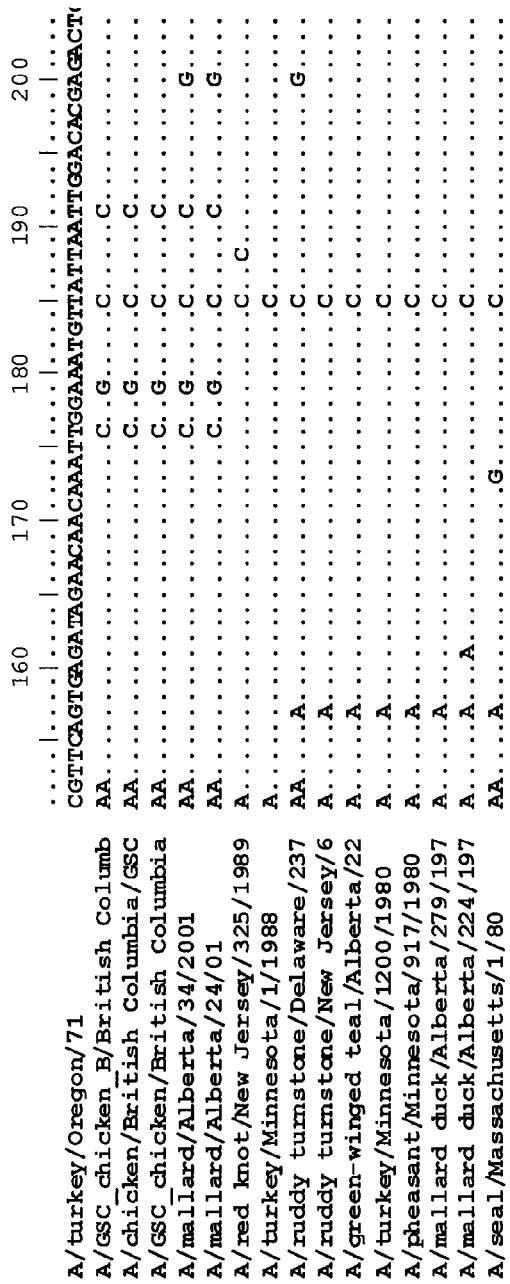
Figure 16A:
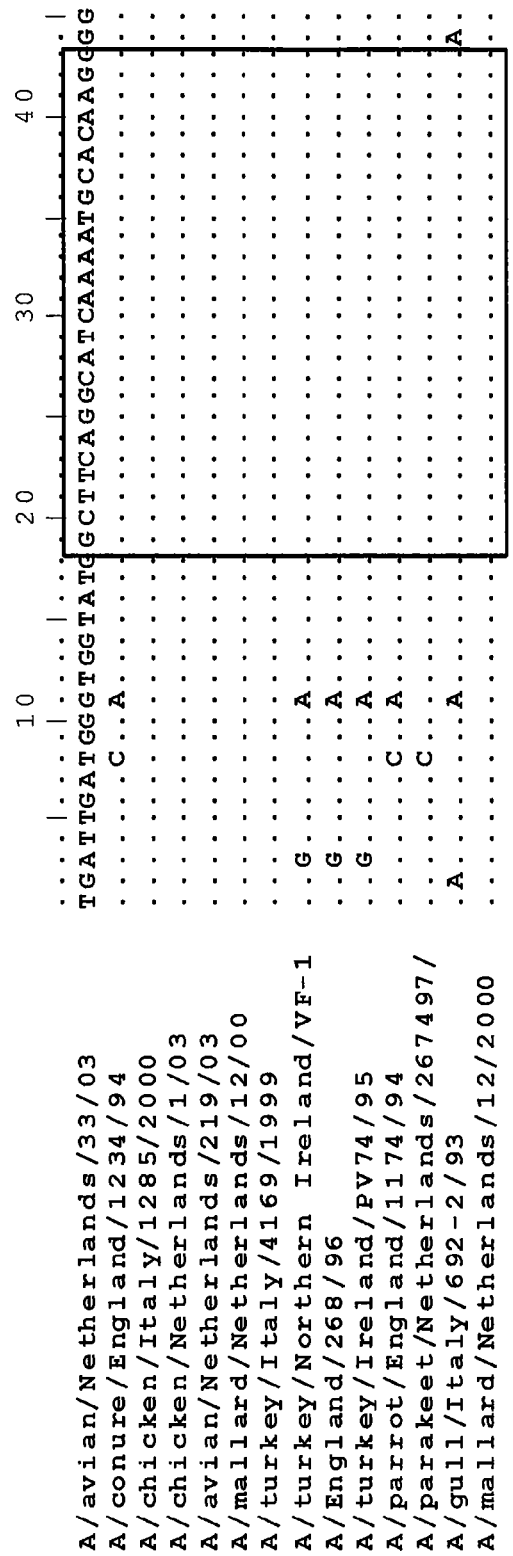
Figure 16A:
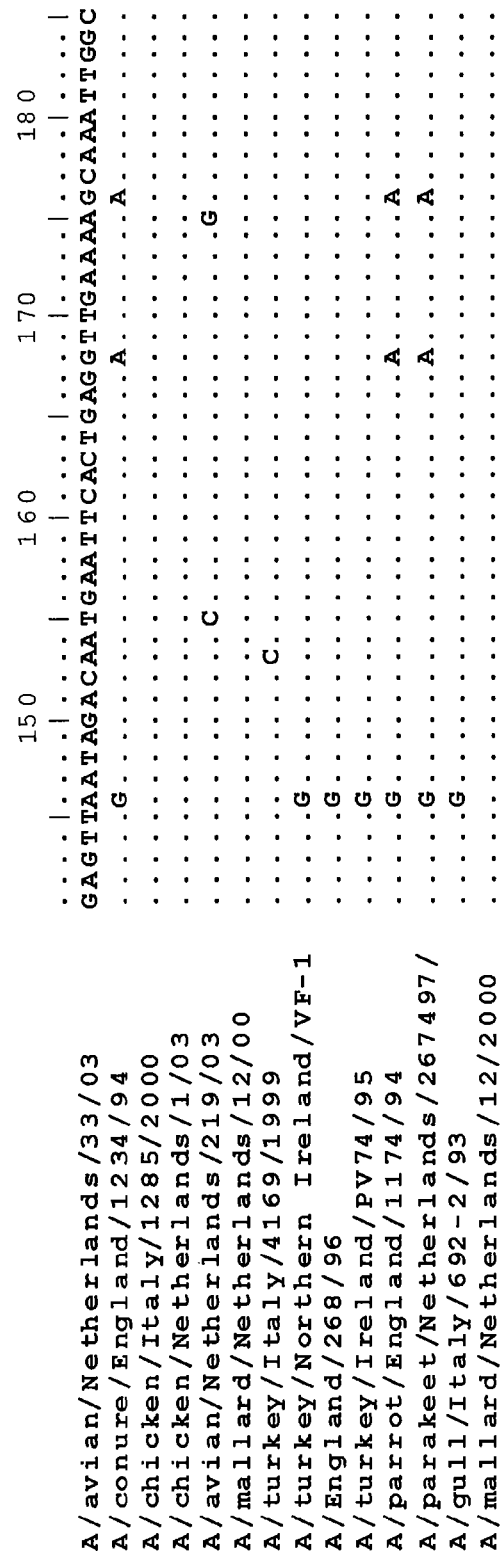
Figure 17A:
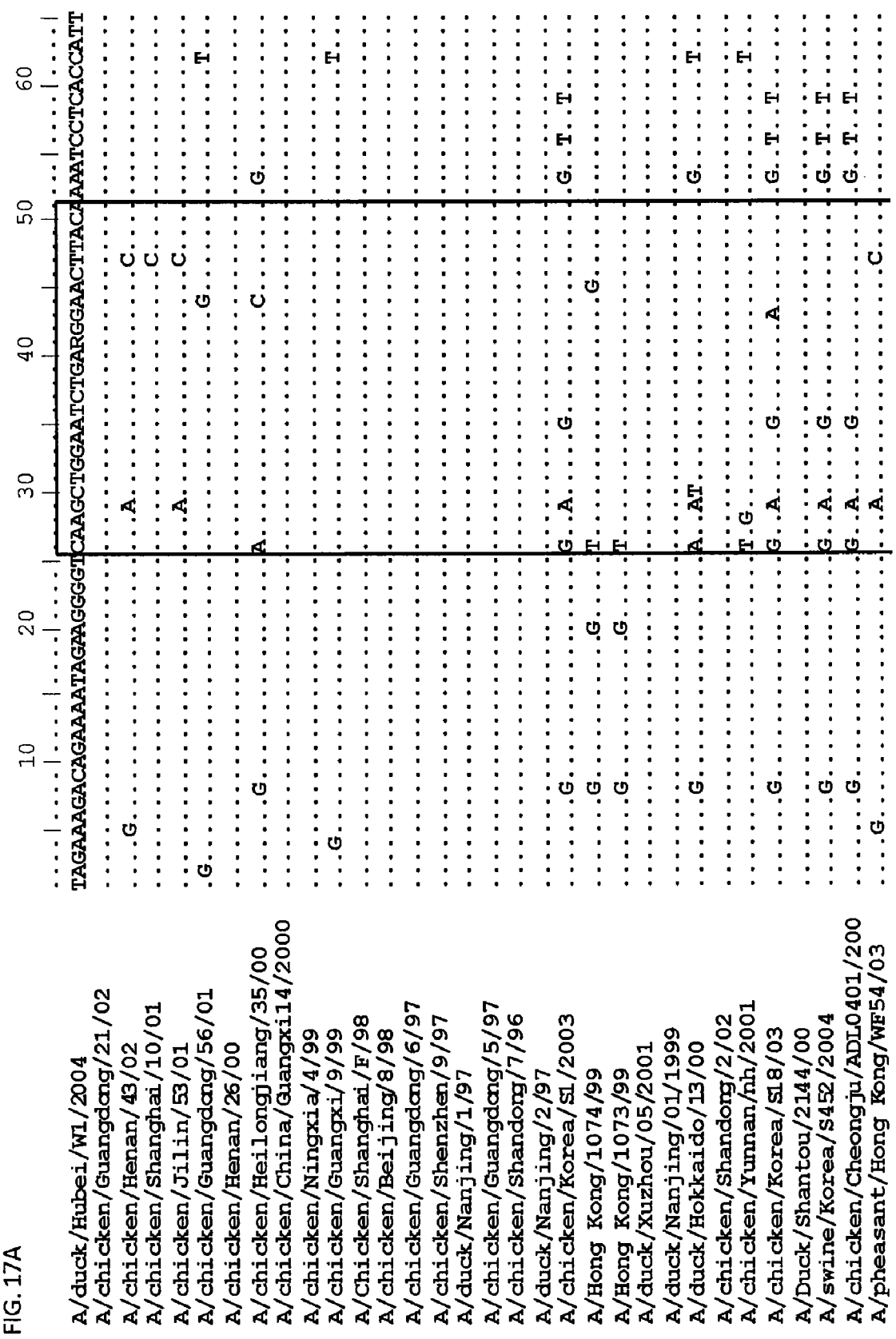
Figure 17D:
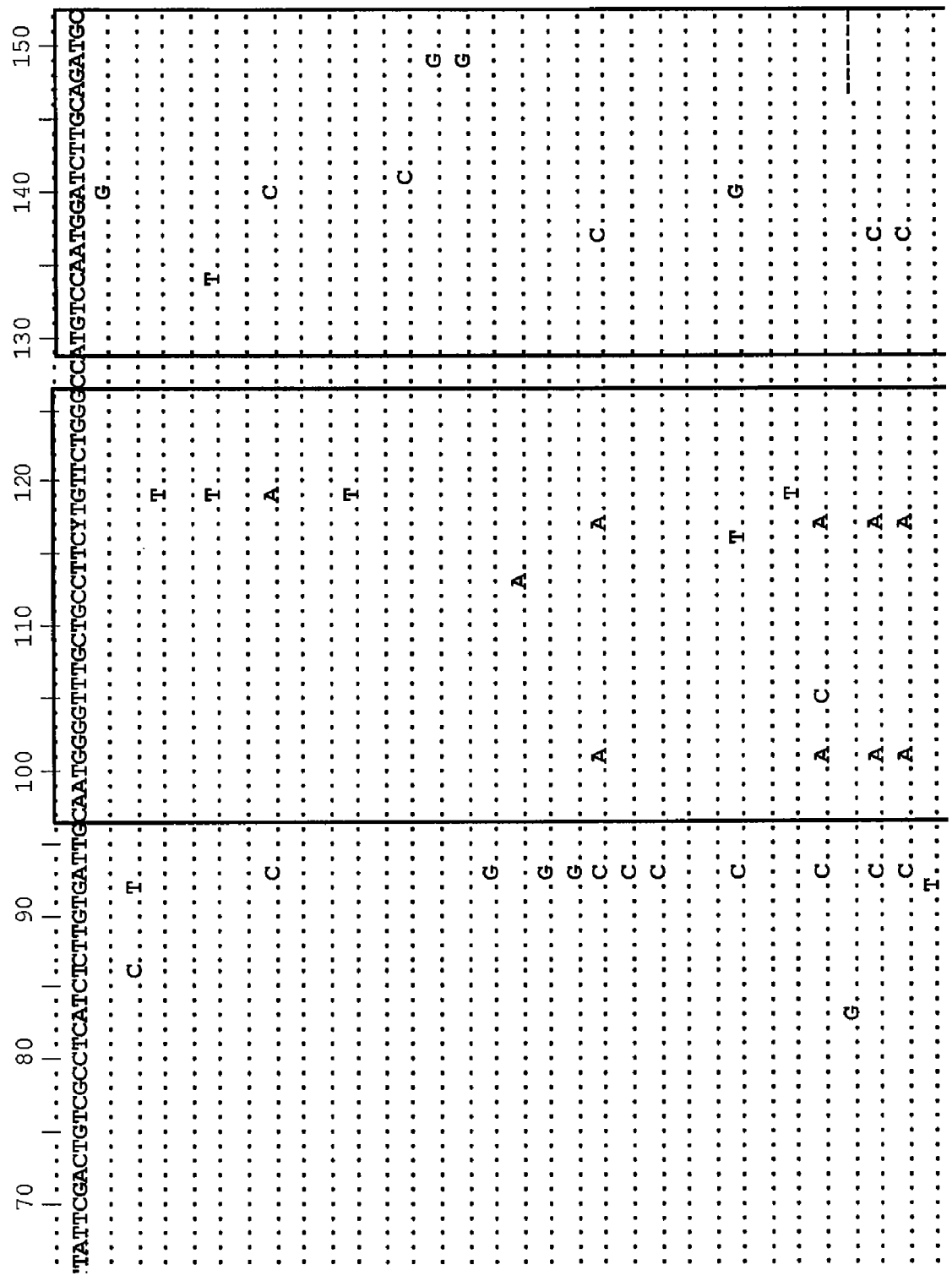
Figure 17E:
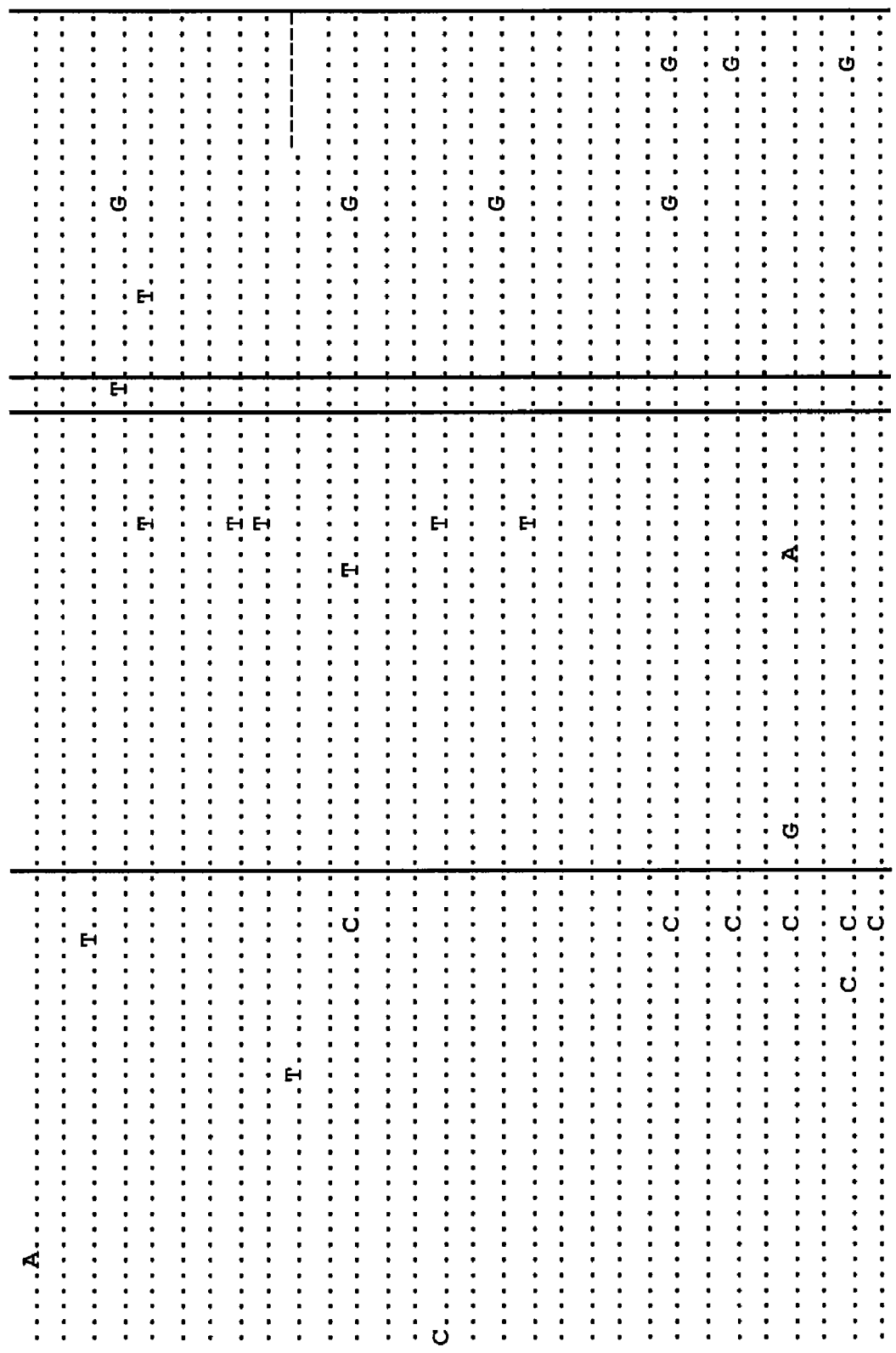
Figure 17F:
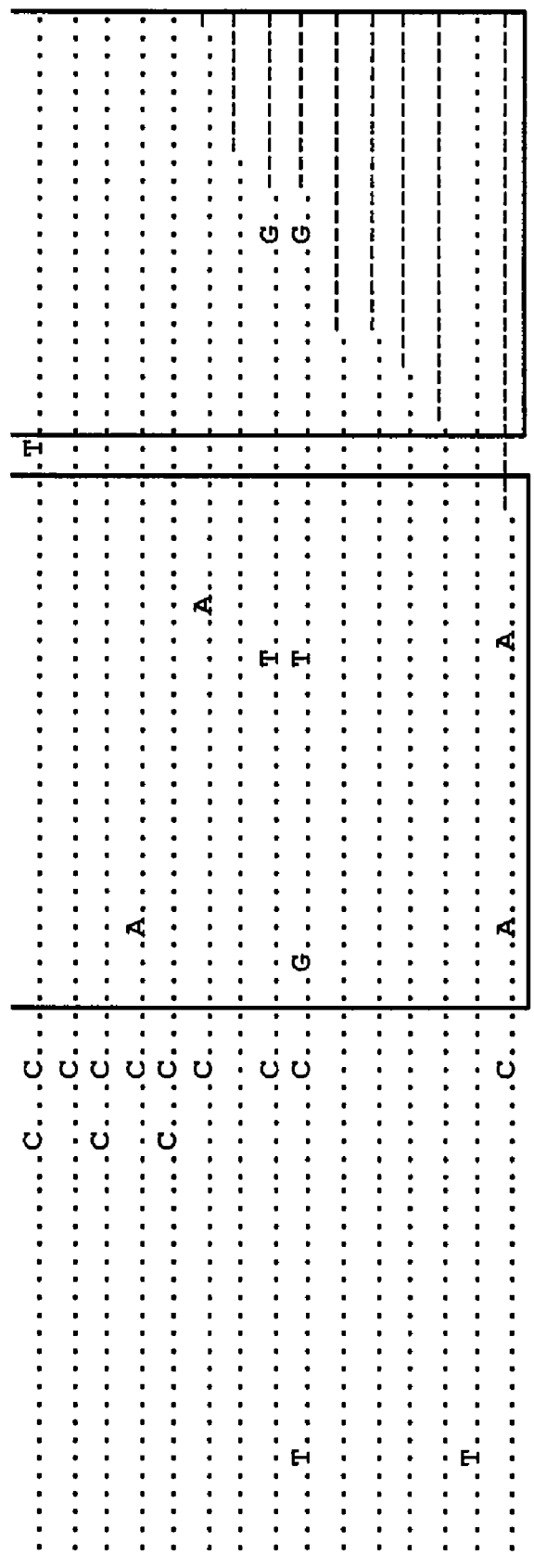
Figure 17G:
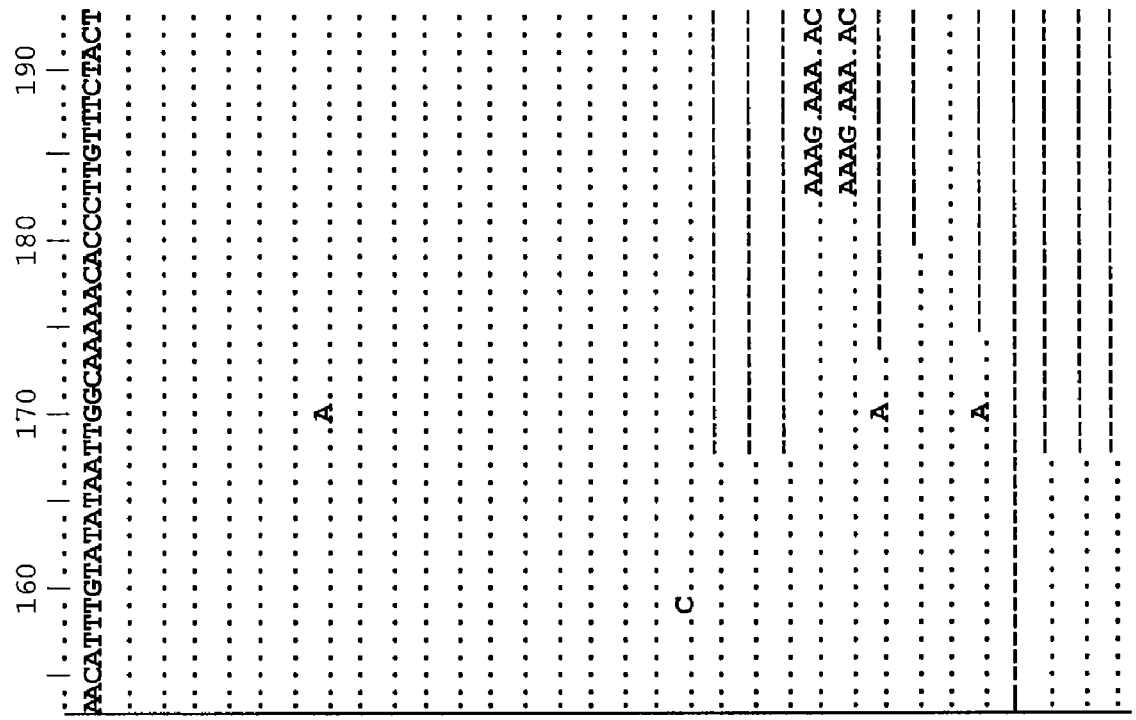
Figure 17H:
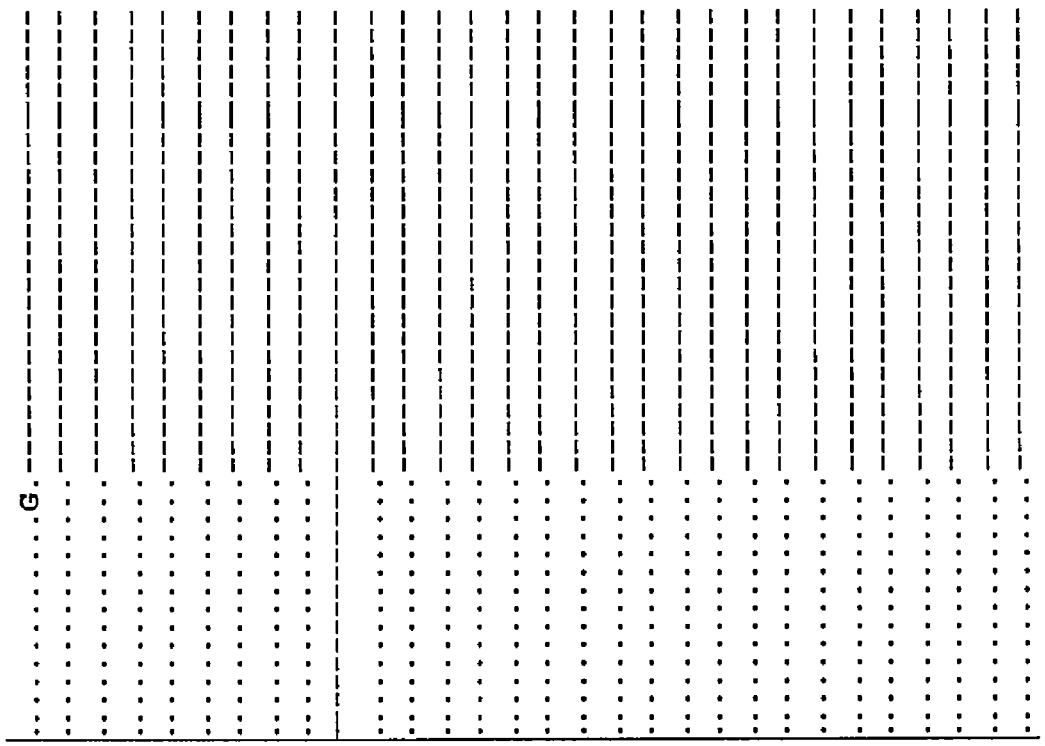
Figure 17I:
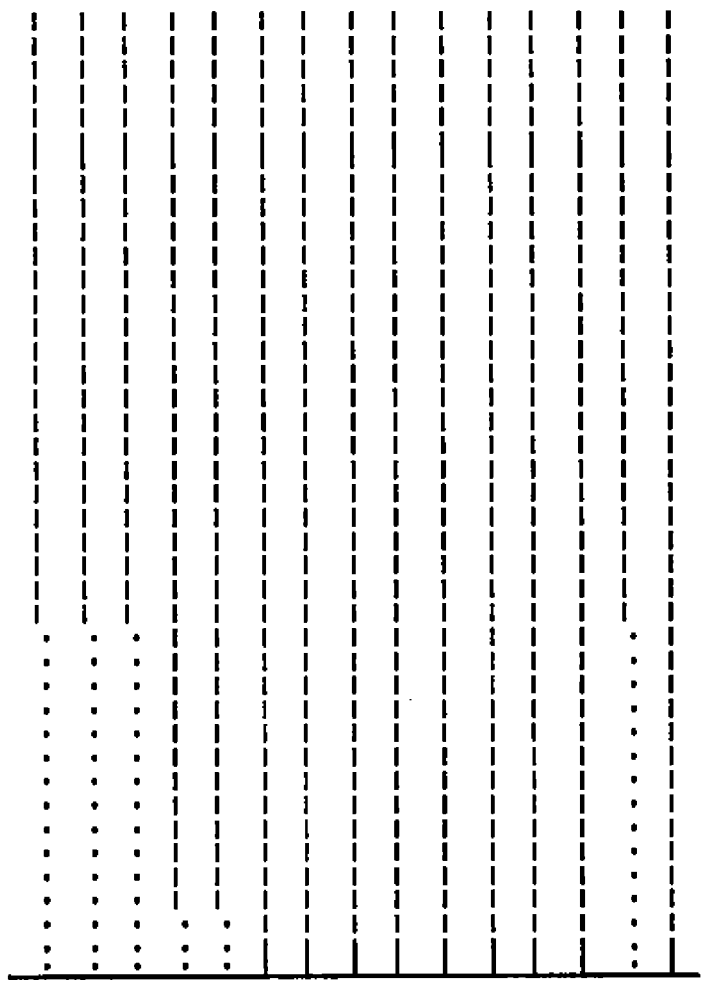

The rt RT-PCR data obtained for samples 1, 2, and 3 is shown in FIGS. 8A, 8B, and 8C respectively. FIG. 8A shows the rt RT-PCR runs for sample 1, which was determined to be positive for influenza type A subtype H5. FIG. 8B shows the rt RT-PCR runs for sample 2, which was determined to be positive for influenza type A subtype H3. FIG. 8C shows the rt RT-PCR runs for sample 3s, which was determined to not contain influenza. The tabulated results are shown in Table 9 below.

TABLE 9

Influenza type and subtype in samples obtained from subjects.

|  | Flu A | H1 | H3 | H5 | Flu B | RNP | Results |
|---|---|---|---|---|---|---|---|
| Sample 1 | + | − | − | + | − | + | A/H5 |
| Sample 2 | + | − | + | − | − | + | A/H3 |
| Sample 3 | − | − | − | − | − | + | Not detected |
| Sample 4 | − | − | − | − | − | − | Invalid |

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. A probe for the detection of an influenza nucleic acid, wherein the probe consists of the nucleotide sequence set forth as SEQ ID NO:24, and optionally a label.

2. A method for detecting an influenza virus nucleic acid in a sample, comprising:
    contacting the sample with the probe of claim 1; and
    detecting hybridization between the influenza virus nucleic acid and the probe, wherein the detection of hybridization indicates the presence of the influenza nucleic acid in the sample.

3. The method according to claim 2, wherein detection of hybridization of the probe to the influenza virus nucleic acid sequence set forth as SEQ ID NO:46 indicates the presence of influenza subtype H5 in the sample.

4. The method according to claim 2, wherein the probe is labeled.

5. The method of claim 4, wherein the probe is radiolabeled, fluorescently-labeled, biotin-labeled, enzymatically-labeled, or chemically-labeled.

6. The method according to claim 4, wherein detecting hybridization comprises detecting a change in signal from the labeled probe during or after hybridization relative to signal from the label before hybridization.

7. The method according to claim 4, wherein the probe is labeled with a fluorophore.

8. The method according to claim 4, wherein the probe is labeled with a fluorescence quencher.

9. The method according to claim 2, further comprising amplifying the influenza virus nucleic acid by polymerase chain reaction (PCR), real-time PCR, reverse transcriptase-polymerase chain reaction (RT-PCR), real-time reverse transcriptase-polymerase chain reaction (rt RT-PCR), ligase chain reaction, or transcription-mediated amplification (TMA).

10. The method according to claim 9, wherein the influenza virus nucleic acid is amplified by rt RT-PCR.

11. The method according to claim 10, wherein the amplifying employs a primer that consists of the nucleotide sequence set forth as SEQ ID NO:17, SEQ ID NO: 18, SEQ ID NO: 22, or SEQ ID NO:23.

12. The method according to claim 11, wherein amplifying the influenza virus nucleic acid comprises contacting the sample with at least one forward primer consisting of the nucleotide sequence set forth as SEQ ID NO:17 or SEQ ID NO: 22, and at least one reverse primer consisting of the nucleotide sequence set forth as SEQ ID NO: 18 or SEQ ID NO:23, wherein the forward and reverse primers are capable of hybridizing to and amplifying the influenza virus nucleic acid sequence.

13. The method according to claim 12, wherein the at least one forward and reverse primer are specific for influenza subtype H5, and consist of the nucleotide sequences set forth as SEQ ID NO:17 and SEQ ID NO:18, or consist of the nucleotide sequences set forth as SEQ ID NO:22 and SEQ ID NO:23.

14. The method according to claim 13, wherein the at least one forward and reverse primer are a set of primers, wherein the set of primers is specific for the amplification of influenza subtype H5 and consists of the nucleotide sequences set forth as SEQ ID NO:17 and SEQ ID NO:18, or is specific for influenza subtype H5 and consists of the nucleotide sequences set forth as SEQ ID NO:22 and SEQ ID NO:23.

15. The method according to claim 2, wherein the sample is a biological sample obtained from a subject.

16. The method of claim 15, wherein the presence of an influenza virus nucleic acid in the biological sample indicates the presence of an influenza infection in the biological sample obtained from a subject.

17. The method according to claim 15, wherein the biological sample is obtained from bronchoalveolar lavage, tracheal aspirates, sputum, nasopharyngeal aspirates, oropharyngeal aspirates, or saliva.

18. The method of claim 2, wherein the probe is arrayed in a predetermined array with an addressable location.

19. The probe according to claim 1, wherein the probe is labeled.

20. The probe according to claim 19, wherein the probe is radiolabeled, fluorescently-labeled, biotin-labeled, enzymatically-labeled, or chemically-labeled.

21. The probe according to claim 19, wherein the probe is labeled with a fluorophore.

22. The probe according to claim 19, wherein the probe is labeled with a fluorescence quencher.

23. A set of probes comprising the probe according to claim 1.

24. A kit for detecting an influenza nucleic acid in a sample, comprising:
the probe of claim 1; and
instructions for hybridizing the probe to the influenza nucleic acid within the sample.

25. The kit according to claim 24, further comprising a primer.

26. A device for detecting an influenza nucleic acid in a sample, comprising a nucleic acid array comprising the probe of claim 1.

27. A method for diagnosing an influenza infection in a subject suspected of having an influenza infection comprising:
obtaining a sample comprising nucleic acids from the subject;
contacting the sample with the nucleic acid probe according to claim 1;
detecting hybridization between an influenza virus nucleic acid sequence present in the sample and the probe, wherein the detection of hybridization indicates that the subject is infected with influenza virus.

28. The method according to claim 27, further comprising amplifying the influenza virus nucleic acid.

29. A primer for the amplification of an influenza nucleic acid sequence, wherein
the primer consists of a nucleic acid sequence set forth as SEQ ID NO:17, SEQ ID NO: 18, SEQ ID NO: 22, or SEQ ID NO: 23.

30. A set of primers for the amplification of an influenza nucleic acid comprising at least one primer according to claim 29.

31. The set of primers according to claim 30, wherein the set of primers comprises:
one or more forward primers consisting of the nucleic acid sequence set forth as SEQ ID NO:17 or SEQ ID NO: 22; and
one or more reverse primers consisting of the nucleic acid sequence set forth as SEQ ID NO: 18 or SEQ ID NO:23, wherein the set of primers is capable of hybridizing to and directing the amplification of the influenza nucleic acid.

32. The set of primers according to claim 31, wherein the forward and reverse primers are a pair of primers, wherein the pair of primers is specific for the amplification of influenza subtype H5 and consists of the nucleic acid sequences set forth in SEQ ID NO:17 and SEQ ID NO:18, or consists of the nucleic acid sequences set forth in SEQ ID NO:22 and SEQ ID NO:23.

33. A kit for detecting an influenza nucleic acid in a sample, comprising:
a probe consisting of the nucleic acid sequence shown in SEQ ID NO: 24; and
one or more pairs of primers selected from the group consisting of:
SEQ ID NO: 17 and SEQ ID NO: 18, and
SEQ ID NO: 22 and SEQ ID NO: 23.

34. The kit of claim 33, wherein the
one or more pairs of primers comprise:
SEQ ID NO: 17 and SEQ ID NO: 18, and
SEQ ID NO: 22 and SEQ ID NO: 23.

* * * * *

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 1
atggtggacc cggtgggctt                                                  20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 2 acggggggatc cggcgggcct                                                 20
```

```
<160> NUMBER OF SEQ ID NOS: 50

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 1
atggtggacc cggtgggctt                                                  20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 2
acgggggatc cggcgggcct                                                  20

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 3
gaccratcct gtcacctctg ac                                               22

<210> SEQ ID NO 4
<211> LENGTH: 26
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<222> LOCATION: (4)..(4)
<223> OTHER INFORMATION: n is g or no nucleotide
<220> FEATURE:
<221> NAME/KEY: misc_feature
<222> LOCATION: (25)..(25)
<223> OTHER INFORMATION: n is c or no nucleotide
<220> FEATURE:
<221> NAME/KEY: misc_feature
<222> LOCATION: (26)..(26)
<223> OTHER INFORMATION: n is g or no nucleotide

<400> SEQUENCE: 4
aggncattyt ggacaaakcg tctann                                           26

<210> SEQ ID NO 5
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 5
agggcattyt ggacaaakcg tcta                                             24
```

```
<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 6
aggcattytg gacaaakcgt ctacg                                              25

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 7
gggcattytg gacaaakcgt ctacg                                              25

<210> SEQ ID NO 8
<211> LENGTH: 24
<212> TYPE: DNA
<213> ORGANISM: Artificial sequence
<220> FEATURE:
<223> OTHER INFORMATION: Synthetic oligonucleotide probe

<400> SEQUENCE: 8
tgcagtcctc gctcactggg cacg                                               24

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 9
aactactact ggactctrct kgaa                                               24

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 10
ccattggtgc atttgagktg atg                                                23

<210> SEQ ID NO 11
<211> LENGTH: 30
<212> TYPE: DNA
<213> ORGANISM: Artificial sequence
<220> FEATURE:
<223> OTHER INFORMATION: Synthetic oligonucleotide probe

<400> SEQUENCE: 11
tgayccaaag cctctactca gtgcgaaagc                                         30

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide primer
```

```
<400> SEQUENCE: 12
aagcattccy aatgacaaac c                                              21

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 13
attgcrccra atatgcctct agt                                            23

<210> SEQ ID NO 14
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 14
cagsatcaca tatgggscct gtcccag                                        27

<210> SEQ ID NO 15
<211> LENGTH: 27
<212> TYPE: DNA
<213> ORGANISM: Artificial sequence
<220> FEATURE:
<223> OTHER INFORMATION: Synthetic oligonucleotide probe

<400> SEQUENCE: 15
caggatcaca tatgggscct gtcccag                                        27

<210> SEQ ID NO 16
<211> LENGTH: 27
<212> TYPE: DNA
<213> ORGANISM: Artificial sequence
<220> FEATURE:
<223> OTHER INFORMATION: Synthetic oligonucleotide probe

<400> SEQUENCE: 16
cagcatcaca tatgggscct gtcccag                                        27

<210> SEQ ID NO 17
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 17
tggaaagtrt aaraaacgga acgt                                           24

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 18
ygctagggar ctcgccactg                                                20
```

```
<210> SEQ ID NO 19
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 19
yractayccg cagtattcag aagaagcaag aytaa                          35

<210> SEQ ID NO 20
<211> LENGTH: 35
<212> TYPE: DNA
<213> ORGANISM: Artificial sequence
<220> FEATURE:
<223> OTHER INFORMATION: Synthetic oligonucleotide probe

<400> SEQUENCE: 20
tgactacccg cagtattcag aagaagcaag actaa                          35

<210> SEQ ID NO 21
<211> LENGTH: 35
<212> TYPE: DNA
<213> ORGANISM: Artificial sequence
<220> FEATURE:
<223> OTHER INFORMATION: Synthetic oligonucleotide probe

<400> SEQUENCE: 21
caactatccg cagtattcag aagaagcaag attaa                          35

<210> SEQ ID NO 22
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 22
ggaatgyccc aaataygtga artcaa                                    26

<210> SEQ ID NO 23
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 23
ctcccctgct crttgctatg gt                                        22

<210> SEQ ID NO 24
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 24
tayccatacc aaccatctac cattccctgc cat                            33

<210> SEQ ID NO 25
<211> LENGTH: 33
<212> TYPE: DNA
<213> ORGANISM: Artificial sequence
<220> FEATURE:
<223> OTHER INFORMATION: Synthetic oligonucleotide probe
```

-continued

```
<400> SEQUENCE: 25
tacccatacc aaccatctac cattccctgc cat                          33

<210> SEQ ID NO 26
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 26
tcctcaaytc actcttcgag cg                                      22

<210> SEQ ID NO 27
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 27
tcctcaactc actcttcgag cg                                      22

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 28
cggtgctctt gaccaaattg g                                       21

<210> SEQ ID NO 29
<211> LENGTH: 27
<212> TYPE: DNA
<213> ORGANISM: Artificial sequence
<220> FEATURE:
<223> OTHER INFORMATION: Synthetic oligonucleotide probe

<400> SEQUENCE: 29
ccaattcgag cagctgaaac tgcggtg                                 27

<210> SEQ ID NO 30
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 30
aaatgcacaa ggagagggaa ctg                                     23

<210> SEQ ID NO 31
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 31
cattgcyacy aasagytcag crt                                     23
```

```
<210> SEQ ID NO 32
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 32
aaagcaccca rtctgcaata gatcagatca caggc                              35

<210> SEQ ID NO 33
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 33
gcttcaggca tcaaaatgca caagg                                         25

<210> SEQ ID NO 34
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 34
cattgctacy aagagttcag crt                                           23

<210> SEQ ID NO 35
<211> LENGTH: 31
<212> TYPE: DNA
<213> ORGANISM: Artificial sequence
<220> FEATURE:
<223> OTHER INFORMATION: Synthetic oligonucleotide probe

<400> SEQUENCE: 35
accacacttc tgtcatggaa tctctggtcc a                                  31

<210> SEQ ID NO 36
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 36
caagctggaa tctgarggaa cttaca                                        26

<210> SEQ ID NO 37
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 37
gcatctgcaa gatccattgg acat                                          24

<210> SEQ ID NO 38
<211> LENGTH: 30
<212> TYPE: DNA
<213> ORGANISM: Artificial sequence
<220> FEATURE:
<223> OTHER INFORMATION: Synthetic oligonucleotide probe
```

-continued

```
<400> SEQUENCE: 38
cccagaacar gaaggcagca aaccccattg                                       30

<210> SEQ ID NO 39
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 39
agatttggac ctgcgagcg                                                   19

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 40
gagcggctgt ctccacaagt                                                  20

<210> SEQ ID NO 41
<211> LENGTH: 23
<212> TYPE: DNA
<213> ORGANISM: Artificial sequence
<220> FEATURE:
<223> OTHER INFORMATION: Synthetic oligonucleotide probe

<400> SEQUENCE: 41
ttctgacctg aaggctctgc gcg                                              23

<210> SEQ ID NO 42
<211> LENGTH: 155
<212> TYPE: DNA
<213> ORGANISM: Influenza virus

<400> SEQUENCE: 42
ctctcatgga gtggctgaag acaagaccra tcctgtcacc tctgactaag gggatttttgg     60 ggtttgtgtt cacgctcacc gtgcccagtg agcgaggact gcagcgtaga cgmtttgtcc    120
araatgccct aaatggaaat ggagatccaa ataat                                155

<210> SEQ ID NO 43
<211> LENGTH: 154
<212> TYPE: DNA
<213> ORGANISM: Influenza virus

<400> SEQUENCE: 43
gaggatgaag aagatggcca tcggatcctc aaytcactct tcgagcgtct taatgaagga     60
cattcaaagc caattcgagc agctgaaact gcggtgggag tcttatccca atttggtcaa    120
gagcaccgat tatcaccaga agagggagac aatt                                154

<210> SEQ ID NO 44
<211> LENGTH: 186
<212> TYPE: DNA
<213> ORGANISM: Influenza virus

<400> SEQUENCE: 44
agtaagagat caggaaggaa gaatcaacta ctactggact ctrctkgaac ctggggatac     60
aataatattt gaggcaaatg gaaatctaat agcgccatgg tatgctttcg cactgagtag    120
```

```
aggctttggr tcaggaatca tcamctcaaa tgcaccaatg gatgaatgtg atgcgaagtg      180
tcaaac                                                                186

<210> SEQ ID NO 45
<211> LENGTH: 197
<212> TYPE: DNA
<213> ORGANISM: Influenza virus

<400> SEQUENCE: 45
attctgaatg catcactcca aatggaagca ttcccaatga caaccatt   caaaatgtaa      60 acaggatcac atatgggscc tgtcccagat atgttaagca aaacactctg aaattggcaa     120
cagggatgcg aaatgtacca gagaaacaaa ctagaggcat attyggygca atcgcgggtt     180
tcatagaaaa tggttgg                                                    197

<210> SEQ ID NO 46
<211> LENGTH: 199
<212> TYPE: DNA
<213> ORGANISM: Influenza virus

<400> SEQUENCE: 46
tatcataaat gtgataatga atgtatggaa agtrtaaraa acggaacgta tgactacccg      60
cagtattcag aagaagcaag actaaaaaga gaggaaataa gtggagtaaa attggaatca     120
ataggaactt accaaatact gtcaatttat tcaacagtgg cgagytccct agcrctggca     180
atcatggtag ctggtctat                                                  199

<210> SEQ ID NO 47
<211> LENGTH: 239
<212> TYPE: DNA
<213> ORGANISM: Influenza virus

<400> SEQUENCE: 47
acaatataca ccctctcacc attggggaat gycccaaata tgtgaaatca acagattag       60 tccttgcgac tgggctcaga aatagccctc aaagagagag aagaagaaaa aagagaggat     120
tatttggagc atagcaggt  tttatagagg gaggatggca gggaatggta gatggttggt     180
atgggtacca ccatagcaay gagcagggga gtgggtacgc tgcagacaaa gaatccact     239

<210> SEQ ID NO 48
<211> LENGTH: 286
<212> TYPE: DNA
<213> ORGANISM: Influenza virus

<400> SEQUENCE: 48
acgggtggta tggttttcgg catcaaaatg cacaaggaga aggaactgca gctgactata      60
aaagcaccca atctgcaata gatcagatca caggcaaatt gaatcgcctg atcgacaaga     120
caaatcagca gtttgagctg atagacaacg cgttcagtga gatagaacaa caaattggaa     180
atgttattaa ttggacacga gactcaatga ccgaagtatg gtcatataat gctgagctgt     240
tggtggcaat ggaaaaccag cacacaatag atcttgcgga ttcaga                    286

<210> SEQ ID NO 49
<211> LENGTH: 271
<212> TYPE: DNA
<213> ORGANISM: Influenza virus
```

```
<400> SEQUENCE: 49
tgattgatgg gtggtatggc ttcaggcatc aaaatgcaca aggggaggga actgctgcag        60
attacaaaag cacccaatca gcaattgatc aaataacagg gaaattaaat cggcttatag       120
aaaaaactaa ccaacagttt gagttaatag acaatgaatt cactgaggtt gaaaagcaaa       180
ttggcaatgt gataaactgg accagagatt ccatgacaga agtgtggtcc tataaygctg       240
aactcttrgt agcaatggag aatcagcaca c                                      271

<210> SEQ ID NO 50
<211> LENGTH: 193
<212> TYPE: DNA
<213> ORGANISM: Influenza virus

<400> SEQUENCE: 50
tagaaagaca gaaaatagaa ggggtcaagc tggaatctga rggaacttac aaaatcctca        60
ccatttattc gactgtcgcc tcatctcttg tgattgcaat ggggtttgct gccttcytgt       120
tctgggccat gtccaatgga tcttgcagat gcaacatttg tatataattg gcaaaaacac       180
ccttgtttct act                                                         193
```